US008846388B2

(12) United States Patent
Nitzel et al.

(10) Patent No.: US 8,846,388 B2
(45) Date of Patent: Sep. 30, 2014

(54) INFECTIOUS CLONES OF TORQUE TENO VIRUS

(75) Inventors: Gregory Paul Nitzel, Mattawan, MI (US); Robert Gerard Ankenbauer, Portage, MI (US); Jay Gregory Calvert, Otsego, MI (US); Donna Steuerwald Dunyak, Richland, MI (US); Jacqueline Gayle Marx, Portage, MI (US); Nancee Lois Oien, Kalamazoo, MI (US); Douglas Steven Pearce, Kalamazoo, MI (US); Mira Ivanova Stoeva, Kalamazoo, MI (US); James Richard Thompson, Portage, MI (US)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 13/501,371

(22) PCT Filed: Apr. 16, 2010

(86) PCT No.: PCT/US2010/031373
§ 371 (c)(1),
(2), (4) Date: Jun. 19, 2012

(87) PCT Pub. No.: WO2011/046634
PCT Pub. Date: Apr. 21, 2011

(65) Prior Publication Data
US 2012/0321654 A1    Dec. 20, 2012

Related U.S. Application Data

(63) Continuation-in-part of application No. PCT/US2009/005662, filed on Oct. 16, 2009.

(51) Int. Cl.
*C12N 15/00* (2006.01)
*A01N 63/00* (2006.01)
*C07K 16/08* (2006.01)
*C12N 7/00* (2006.01)
*A61K 39/12* (2006.01)
*C07K 14/005* (2006.01)

(52) U.S. Cl.
CPC .............. *A61K 39/12* (2013.01); *C07K 16/081* (2013.01); *C12N 7/00* (2013.01); *C07K 2317/33* (2013.01); *C12N 2750/00034* (2013.01); *C12N 2750/00021* (2013.01); *C12N 2750/10021* (2013.01); *C12N 2750/00022* (2013.01); *C12N 2750/10034* (2013.01); *C07K 14/005* (2013.01)
USPC ....... 435/320.1; 435/455; 424/93.2; 424/93.6

(58) Field of Classification Search
None
See application file for complete search history.

(56) References Cited

U.S. PATENT DOCUMENTS

| 3,137,631 | A | 6/1964 | Soloway |
| 3,959,457 | A | 5/1976 | Speaker et al. |

(Continued)

FOREIGN PATENT DOCUMENTS

| WO | WO 95/28227 A1 | 10/1995 |
| WO | WO 00/66621 A1 | 11/2000 |

(Continued)

OTHER PUBLICATIONS

Niel et al., "Rolling-circle amplification of Torque teno virus (TTV) complete genomes from human and swine sera and identification of a novel swine TTV genogroup," Journal of General Virology 86, pp. 1343-1347 (2005).*

(Continued)

*Primary Examiner* — Zachariah Lucas
*Assistant Examiner* — M. Franco Salvoza
(74) *Attorney, Agent, or Firm* — Barbara L. Renda; E. Victor Donahue

(57) ABSTRACT

The present invention is directed to novel nucleotide and amino acid sequences of Torque teno virus ("TTV"), including novel genotypes thereof, all of which are useful in the preparation of vaccines for treating and preventing diseases in swine and other animals. Vaccines provided according to the practice of the invention are effective against multiple swine TTV genotypes and isolates. Diagnostic and therapeutic polyclonal and monoclonal antibodies are also a feature of the present invention, as are infectious clones useful in the propagation of the virus and in the preparation of vaccines. Particularly important aspects of the invention include vaccines that provide TTV ORF1 protein, or peptide fragments thereof, as antigen.

2 Claims, 10 Drawing Sheets

(56) References Cited

U.S. PATENT DOCUMENTS

| | | | |
|---|---|---|---|
| 4,016,100 A | 4/1977 | Suzuki et al. | |
| 4,205,060 A | 5/1980 | Monsimer et al. | |
| 4,452,747 A | 6/1984 | Gersonde et al. | |
| 4,606,940 A | 8/1986 | Frank et al. | |
| 4,744,933 A | 5/1988 | Rha et al. | |
| 4,921,706 A | 5/1990 | Roberts et al. | |
| 4,927,637 A | 5/1990 | Morano et al. | |
| 4,944,948 A | 7/1990 | Uster et al. | |
| 5,008,050 A | 4/1991 | Cullis et al. | |
| 5,009,956 A | 4/1991 | Baumann | |
| 5,132,117 A | 7/1992 | Speaker et al. | |
| 6,395,472 B1 * | 5/2002 | Leary et al. | 435/5 |
| 7,544,362 B1 | 6/2009 | Yoo et al. | |
| 2007/0041989 A1 | 2/2007 | Jestin et al. | |
| 2011/0064758 A1 | 3/2011 | Nitzel et al. | |

FOREIGN PATENT DOCUMENTS

| | | |
|---|---|---|
| WO | WO 2004/014956 A1 | 2/2004 |
| WO | WO 2004/014957 A1 | 2/2004 |
| WO | WO 2006/084319 A1 | 8/2006 |
| WO | WO 2008106803 A1 * | 9/2008 |
| WO | WO 2008/127279 A2 | 10/2008 |
| WO | WO 2008127279 A2 * | 10/2008 |
| WO | WO 2008/150275 A2 | 12/2008 |
| WO | WO 2010/044889 A2 | 4/2010 |

OTHER PUBLICATIONS

Okamoto et al., "Genomic characterization of TT viruses (TTVs) in pigs, cats and dogs and their relatedness with species-specific TTVs in primates and tupaias," J. Gen. Virol. 83: pp. 1291-12297 (2002).*
Kekarainen et al., "Torque teno virus infection in the pig and its potential role as a model of human infection," The Veterinary Journal 180: pp. 163-168 (2009).*
Nishizawa, T. et al., 1997 "A Novel DNA Virus (TTV) Associated with Elevated Transaminase Levels in Posttransfusion Hepatitis of Unknown Etiology", Biochemical and Biophysical Research Communications, vol. 241, pp. 92-97.
McKeown, N.E. et al., 2004, "Molecular characterization of porcine TT virus, an orphan virus, in pigs from six different countries", Veterinary Microbiology, vol. 104, pp. 113-117.
Biagini, P., 2004, "Human circoviruses", Veterinary Microbiology, vol. 98, pp. 95-101.
Krakowka, S. et al., 2008, "Evaluation of induction of porcine dermatitis and nephropathy syndrome in gnotobiotic pigs with negative results for porcine circovirus type 2", American Journal of Veterinary Research, vol. 69(12), pp. 1615-1622.
Kakkola, L. et al., 2008, "Expression of all six human Torque teno virus (TTV) proteins in bacteria and in insect cells, and analysis of their IgG responses", Virology, vol. 382, pp. 182-189.
Mushahwar, I. et al., 1999, "Molecular and biophysical characterization of TT virus: Evidence for a new virus family infecting humans", Proceedings of the National Academy of Science, USA, vol. 96, pp. 3177-3182.
Kekarainen, T. and Segales, J., 2009, "Torque teno virus infection in the pig and its potential role as a model of human infection", The Veterinary Journal, vol. 180, pp. 163-168.
Tatusova, T.A. and Madden, T.L., 1999, "BLAST 2 sequences, a new tool for comparing protein and nucleotide sequences", FEMS Microbiology Letters, vol. 174, pp. 247-250.
Henikoff, S. and Henikoff, J., 1992, "Amino acid substitution matrices from protein blocks", Proceedings of the National Academy of Science USA, vol. 89, pp. 10915-10919.
Domb, A. et al., 1992, "Degradable Polymers for Site-specific Drug Delivery", Polymers for Advanced Technologies, vol. 3, pp. 279-292.
Krakowka, S. et al., 2008, "Evaluation of the effects of porcine genogroup 1 torque teno virus in gnotobiotic swine", American Journal of Veterinary Research, vol. 69, pp. 1623-1629.
International Search Report, Application No. PCT/US2009/005662, International filing date Oct. 16, 2009.
Written Opinion of the International Search Authority, Application No. PCT/US2009/005662, International filing date Oct. 16, 2009.
Database EMBL, Feb. 11, 2005, Niel, C. et al.: "Torque teno sus virus 2 isolate 1p. complete genome", XP002580428, Database accession No. AY823990 (D3).
Database EMBL, Feb. 11, 2005, Niel, C. et al.: "Toeque teno virus isolate 2p. complete genome", XP002580429, Database accession No. AY823991 (D4).
Database EMBL, Feb. 11, 2006, Kekarainen, T. et al.: "Torque teno virus isolate Sd-TTV629/04 noncoding region, partial sequence", XP002580430, Database accession No. DQ229863 (D5).
Database EMBL, Jun. 22, 2008, Yin, H. et al.: "Torque teno virus isolate GD2-2 ORF3 gene, complete cds; and ORF1 and ORF2 genes, partial cds", XP002580431, Database accession No. EU753361 (D6).
International Search Report and Written Opinion of the International Searching Authority, Application No. PCT/US 10/31373, International filing date Apr. 16, 2010.
Niel, C. et al., 2005, "Rolling-circle amplification of Torque teno virus (TTV) complete genomes from human and swine sera identification of a novel swine TTV genogroup", Journal of General Virology, vol. 86, pp. 1343-1347.
GenBank, Apr. 19, 2005, Niel, C. et al., "ORF1 [Torque teno virus]", Database accession No. AAW79284.

* cited by examiner

Lane Number
12 11 10 9 8 7 6 5 4 3 2 1

Primary bands of interest

Secondary bands of interest

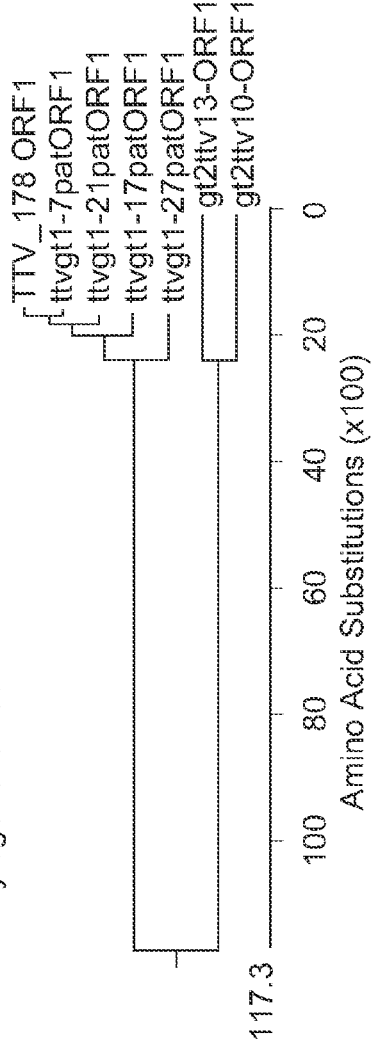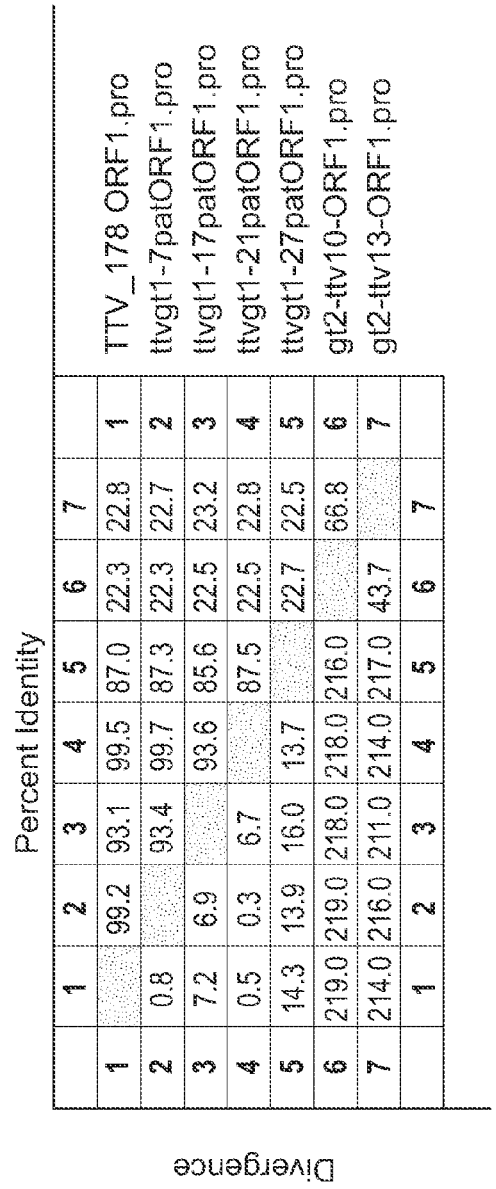
FIG. 4

FIG. 5A

```
Majority          MAPARRWRRFGRRRRRYRKRRYGWRRRYVRYRPRYYRPRYYRRRWLVRRRRRSVTRRGGRRAPYRISAFNPKVMRRVVIRGWW 10        20        30        40        50        60        70        80
                  +---------+---------+---------+---------+---------+---------+---------+---------+

TTV_178 ORF1.pro  MAFARRWRRFGRRRRRYRKRRYGWRRRYVRYRPRYYRPRYYRRRWLVRRRRRSVTRRGGRRAPYRISAFNPKVMRRVVIRGWW   80
ttvgt1-7patORF1.pro   MAFARKWRRRFGRRRRRYRKRRYGWRRRYVRYRPRYYRPRYYRRRWLVRRRRRSVTRRGGRRAPYRISAFNPKVMRRVVIRGWW   80
ttvgt1-17patORF1.pro  MAPARRWRRGFGRRRRRYRKRRYGWRRRWRYFPRYYRPRYYRRRWLVRRRRRSVTRRGGRRAPYRISAFNPKIMRRVVIRGWW   80
ttvgt1-21patORF1.pro  MAFARRWRRRFGRRRRRYRKRRYGWRRRYVRYRPRYYRPRYYRRRWLVRRRRRSVTRRGGRRAPYRISAFNPKVMRRVVIRGWW   80
ttvgt1-27patORF1.pro  MAPTRRWRRRFGRRRRRYRKRRYGWRRRYVRYRPRYYRPRYYRRRWLVRRRRRSVTRRGGRRAPYRVSAFNPKVMRRVVIRGWW   80
gt2-ttv10-ORF1.pro    -MPFHRYRRRRRRPTRRWRRRF---Q-RVFRYR--Y-RR--APRRRRRYKVRR---RVVKKAPVIQWFPPTVRNCFIKGIW     69
gt2-ttv13-ORF1.pro    -MPYRRYRRRRRRRPTRRWWHRRW--R-RVFRYR--R-RR--APRRRR-TKVRR--RR-RKAPVIQWNPPSRRTCLIEGFW     67

Majority          PILQCLKGQESLRYRPLQWDVEKSWRINTTLEDNYGYLVQYGGGWGSGEVTLEGLYQEHLLWRNSWSKGNDGMDL--VRY 90       100       110       120       130       140       150       160
                  +---------+---------+---------+---------+---------+---------+---------+---------+

TTV_178 ORF1.pro  PILQCLKGQESLRYRPLQWDVEKSWRINTTLEDNYGYLVQYGGGWGSGEVTLEGLYQEHLLWRNSWSKGNDGMDL--VRY   158
ttvgt1-7patORF1.pro   PILQCLKGQESLRYRPLQWDVEKSWRINTTLEDNYGYLVQYGGGWGSGEVTLEGLYQEHLLWRNSWSKGNDGMDL--VRY   158
ttvgt1-17patORF1.pro  PILQCLRGQESLRYRPLQWDVEKSWRIKTDLEDNYGYLVQYGGGWGSGEVTLEGLYQEHLLWRNSWSKGNDGMDL--VRY   158
ttvgt1-21patORF1.pro  PILQCLKGQESLRYRPLQWDVEKSWRINTDLEDNYGYLVQYGGGWGSGEVTLEGLYQEHLLWRNSWSKGNDGMDL--VRY   158
ttvgt1-27patORF1.pro  PILQCLKGQESLRYRPLQWDTERQWRVQDFEDQYGYLVQYGGWGSGDVTLEGLYQEHLLWRNSWSKGNDGMDL--VRY    158
gt2-ttv10-ORF1.pro    PLSYGHWLRTCLPMR--------------KE--NGLIFLGGGIDWTVWSLQNLYHEKLNWRNVWTSSNDGWEF--ARF   129
gt2-ttv13-ORF1.pro    PLSYGHWFRTCLPFR--------------RK--NGLIFTGGGCDWTQWSLQNLYHEKLNWRNIWTASNVGMEFEFARF   129

Majority          FGCIVVLYPLKDQYWFWDTDFKELYAESIKEYSQPSVMMAKRTKIVIARSRAPHRRKVR--RIFIPPPSRDTTQWQF 170       180       190       200       210       220       230       240
                  +---------+---------+---------+---------+---------+---------+---------+---------+

TTV_178 ORF1.pro  FGCIVVLYPLKDQYWFWDTDFKELYAESIKEYSQPSVMMAKRTKIVIARSRAPHRRKVR--RIFIPPPSRDTTQWQF   236
ttvgt1-7patORF1.pro   FGCIVVLYPLKDQYWFWDTDFKELYAESIKEYSQPSVMMAKRTKIVIARSRAPHRRKVR--RIFIPPPSRDTTQWQF   236
ttvgt1-17patORF1.pro  FGCIVVLYPLKDQYWFWDTDFKELYAESIKEYSQPSVMMAKRTKIVIARSRAPHRRKVR--RIFIPPPSRDTTQWQF   236
ttvgt1-21patORF1.pro  FGCIVVLYPLKDQYWFWDTDFKELYAESIKEYSQPSVMMAKRTKIVIARSRAPHRRKVR--RIFIPPPSRDTTQWQF   236
ttvgt1-27patORF1.pro  FGCVVVLYPLKDQYWFWDTDFKELYAENIKEYSQPSVMMAKTRIVIARDRAPHRRKVR--RIFIPPPSRDTTQWQF    236
gt2-ttv10-ORF1.pro    RYAKFKFRHTTRSYVVTWDQDIPCKPLP--YTNLHPFVMLLKKHHKVVLSKQDCNPRKMDKPVTLKIKPPPKLTSQWRL   207
gt2-ttv13-ORF1.pro    LKGKFYFFRHPWRNYIVTWDQDIPCKPLF--YQNLHPLLMLLKQHEKLVLSQQNCNPNTRKQKPVTLKFRPPKLTSQWRL   207
```

FIG. 5B

```
Majority       QTDFCNRPLFTWAAGLIDLQKPFDANGAFRNAWWLEQRNEA----------GEMKYIELWGRVPPQGDTELPLQTEFQKP
                        |         |         |         |         |         |         |         |
                       250       260       270       280       290       300       310       320

TTV_178_ORF1.pro       QTDFCNKPLFTWAAGLIDLQKPFDANGAFRNAWWLEQRNEA----------GEMKYIELWGRVPPQGDTELPLQTEFQKP      306
ttvgt1-7patORF1.pro    QTDFCNKPLFTWAAGLIDLQKPFDANGAFRNAWWLEQRNEA----------GEMKYIELWGRVPPQGDTELPVQEFQKP      306
ttvgt1-17patORF1.pro   QTEFCNKPLFTWAAGLIDLQKPFDANGAFRNAWWLEQRNEA----------GEMKYIELWGRVPPQGDTELPAQEFQKP      306
ttvgt1-21patORF1.pro   QTDFCNRPLFTWAAGLIDLQKPFDANGAFRNAWWLEQRNEA----------GEMKYIELWGRVPPQGDTELPLQTEFQKP      306
ttvgt1-27patORF1.pro   QTDFCNRPLFTWAAGLIDMQKPFDANGAFRNAWWLEQRTEQ----------GEMKYIELWGRVPPQGDSELPKKSEFTTA      306
gt2-ttv10-ORF1.pro     SRELSKIPLLRLGVSLLDFREPWVEG-FGNAFFSTLGVEADKSNLKTSAWCQCKYFWIYDTGVNNHVYVVMLNEJAGDN      285
gt2-ttv13-ORF1.pro     SRELAKMPLIRLGVSFIDLTEPWLEG-WGNAFYSVLGVEAIKEQGHWSNWSQIKYYWIYDTGVNAVYVVMLKQDVDDN      285

Majority       SGY-------NPKYYVNPGEEKPIYPVIIYVDMKDQKPRKKYCVCYNKTLNRWRSAQASTLKIGDLQGLVLRQLMN
                        |         |         |         |         |         |         |         |
                       330       340       350       360       370       380       390       400

TTV_178_ORF1.pro       SGY-------NPKYYVNPGEEKPIYPVIIYVDMKDQKPRKKYCVCYNKTLNRWRSAQASTLKIGDLQGLVLRQLMN      375
ttvgt1-7patORF1.pro    SGY-------NPKYYVNPGEEKPIYPVIIYVDMKDQKPRKKYCVCYNKTLNRWRSAQASTLKIGDLQGLVLRQLMN      375
ttvgt1-17patORF1.pro   DGY-------NPKYYVQAGEEKPIYPIIIYVDKKDQKARKKYCVCYNKTLNRWRAAQASTLKIGDLQGLVLRQLMN      375
ttvgt1-21patORF1.pro   SGY-------NPKYYVNPGEEKPIYPVIIYVDMKDQKPRKKYCVCYNKTLNRWRSAQASTLKIGNLKGLVLRQLMN      375
ttvgt1-27patORF1.pro   TD--------NKNYNVNDGEEKPIYPIIIYVDQKDQKPRKKYCVCYNKTLNRWRLGQASTLKIGNLKGLVLRQLMN      374
gt2-ttv10-ORF1.pro     AG------DLITNQ----NSIAHIEQIGEGYPWLYFFGRSEEDLKALATSNTNIRNEFNTNPNSKKLKIAVIGWASSNWTA      357
gt2-ttv13-ORF1.pro     PGKMASTFKTTQQGHFNAIDHIELINEGWPYWLYKFFGKSEQDIKKEAHS-AEIAREYATNPKSKKLKIGIVGWASSNFTT      364

Majority       QEMTYYTWKEG-EFTNVFLQRWRGFRLAVIDARKADTENPTVQTWKVDGXWNTQGTVLKEVFNINLNNEQMRQADFGKLNL
                        |         |         |         |         |         |         |         |
                       410       420       430       440       450       460       470       480

TTV_178_ORF1.pro       QEMTYYTWKEG-EFTNVFLQRWRGFRLAVIDARKADTENPTVQTWKVDGQWNTQGTVLKEVFNINLNNEQMRQADFGKLNL      454
ttvgt1-7patORF1.pro    QEMTYYTWKEG-EFTNVFLQRWRGFRLAVIDARKADTENPTVQTWKVDGQWNTQGTVLKEVFNINLNNEQMRQADFGKLNL      454
ttvgt1-17patORF1.pro   QEMTYYTWKEG-EFTNVFLQRWKGFRLAVIDARKGDTENPTVQTWKVDGNWNTSGTVLQEVFGINLTQQQMRASDFAKLTL      454
ttvgt1-21patORF1.pro   QEMTYYTWKEG-EFTNVFLQRWRGFRLAVIDARKADTENPTVQTWKVDGQWNTQGTVLKEVFNINLNNEQMRQADFGKLNL      454
ttvgt1-27patORF1.pro   QEMTYIWKEG--EYSSPFVQRWKGSRFVIDARKADQENPKVSTWPIEGVWNTQGTVLKDVFQIDINSTNFRAADFGKITL      453
gt2-ttv10-ORF1.pro     QDSTQGAN----TPIEGTYLISHVLQTSGHTAGAAQINNLFASGWPNSQNYPPLN---LDKNNFDWGKRALCILRN-NMKI      430
gt2-ttv13-ORF1.pro     PGSSQNSGGNIAAIQGGYVAWAGGGQGK-LMLGAGSIGNLYQQGWPSNQMWPNTN----RDETNFDWGLRSLCILRD-NMQL      439
```

FIG. 5C

```
Majority          PKSPHDIDFGHHSRFGPFCVKNE------PLEFQLTAPEPTNLWFQYKFLFQFG--GEYQPPTGIRDPCADNPAYPVPQS
                          490       500       510       520       530       540       550       560
                  ----+----+----+----+----+----+----+----+----+----+----+----+----+----+----+----+
TTV_178_ORF1.pro  PKSPHDIDFGHHSRFGPFCVKNE------PLEFQLTAPEPTNLWFQYKFLFQFG--GEYQPPTGIRDPCADNPAYPVPQS  526
ttvgt1-7patORF1.pro  PKSPHDIDFGHHSRFGPFCVKNE------PLEFQLTAPEPTNLWFQYKFLFQFG--GEYQPPTGIRDPCADNPAYPVPQS  526
ttvgt1-17patORF1.pro PKSPHDIDFGHHSRFGPFCVKNE------PLEFQLTAPEPINLWFQYKFLFQFG--GEYQPPTGIRDPCADNQPYPVPQS  526
ttvgt1-21patORF1.pro PKSPHDIDFGHHSRFGPFCVKNE------PLEFQLTAPEPTNLWFQYKFLFQFG--GEYQPPTGIRDPCADNPAYPVPQS  526
ttvgt1-27patORF1.pro PKSPHDLDFGHHSRFGPFCVKNE------PLEFQVYPPEPTNLWFQYRFFFQFG--GEYQPPTGIRDPCVDTPAYPVPQS  525
gt2-ttv10-ORF1.pro GNQNLDDETTMPALFGPLVEKAN-WEGLEKIPELKPELKDYNILMRYNRFQWGGHGTETFKTSIGDPSQIPCPYGPGEA   509
gt2-ttv13-ORF1.pro GNQELDDECTMLSLFGPFVEKANPIFATTDPKYFKPELKDYNLIMKYAPKFQWEGHGTERFKTTIGDPSTIPCPFEPGDR  519

Majority          GSITHPKFAGKGGMLTETDRWGITAASSRALSADTPTEATQSALLRGDSEKKGEETEETSSSSSITSAESSTEGDGSSDD
                          570       580       590       600       610       620       630       640
                  ----+----+----+----+----+----+----+----+----+----+----+----+----+----+----+----+
TTV_178_ORF1.pro  GSITHPKFAGKGGMLTETDRWGITAASSRALSADTPTEATQSALLRGDSEKKGEETEETSSSSSITSAESSTEGDGSSDD  606
ttvgt1-7patORF1.pro  GSITHPKFAGKGGMLTETDRWGITAASSRTLSADTPTEATQSALLRGDSEKKGEETEETSSSSITSAESSTEGDGSSDD  606
ttvgt1-17patORF1.pro GSITHPKFAGKGGMLTETDRWGITAASSRALSADTPTEAAQSALLRGDSEKKGEETEETSSSSITSAESSTEGDGSSDD  606
ttvgt1-21patORF1.pro GSITHPKFAGKGGMLTETDRWGITAASSRALSADTPTEATQSALLRGDSEKKGEETEETSSSSITSAESSTEGDGSSDD  606
ttvgt1-27patORF1.pro GSITHPKFAGKGGMLTETDRWGITPASTRALCADTPTEATQSALLRGDSEKKGEETEETSSSSITSAESSTEGDGSSDD  605
gt2-ttv10-ORF1.pro PQHLVRNPSKVHEGVLNAWDYDYDGIVRKDTLKRLLAIPTDSEEE-KAYPLAGPKTEKLPSSDEEGESDISSSDSTQE   588
gt2-ttv13-ORF1.pro FHSGIQDPSKVQNTVLNPWDYDCDGIVRKDTLKRLLELPTETEEEKAYPLLGQKTEKEPLSDSEESVISSTSSGSDQE   599

Majority          EETIRRRRRTWKRLRRMVREQLDRRMDHKRQRLH-
                          650       660       670
                  ----+----+----+----+----+----+----+
TTV_178_ORF1.pro  EETIRRRRRTWKRLRRMVREQLDRRMDHKRQRLH.  641
ttvgt1-7patORF1.pro  EETIRRRRRTWKRLRRMVREQLDRRMDHKRQRLH.  641
ttvgt1-17patORF1.pro EETIRRRRRTWKRLRRMVREQLDRRMDHKRQRLH.  641
ttvgt1-21patORF1.pro EETIRRRRRTWKRLRRMVREQLDRRMDHKRQRLH.  641
ttvgt1-27patORF1.pro EETVRRRRRTWKRLRRMVREQLDRRMDHKRQRLH.  640
gt2-ttv10-ORF1.pro SEEEKRYRRRHKPSKRRLLQEVQRLIVKRFETL.   621
gt2-ttv13-ORF1.pro --EETQRRKHKPSKRRLLKHLQRVVKRMKTL.     630
```

INFECTIOUS CLONES OF TORQUE TENO VIRUS

The present application is the U.S. national stage (37 USC 371) of international application PCT/US2010/031373, filed Apr. 16, 2010, and claims the benefit, under 35 USC 120, 363, of international application PCT/US20091005662, filed Oct. 16, 2009, and which designates the United States.

FIELD OF THE INVENTION

The present invention is directed to novel nucleotide and amino acid sequences of Torque teno virus ("TTV"), including novel genotypes thereof, all of which are useful in the preparation of vaccines for treating and preventing diseases in swine and other animals. Vaccines provided according to the practice of the invention are effective against multiple swine TTV genotypes and isolates. Diagnostic and therapeutic polyclonal and monoclonal antibodies are also a feature of the present invention, as are infectious clones useful in the propagation of the virus and in the preparation of vaccines. Of particular importance, there are disclosed vaccines that comprise, as antigen, the expressed protein of single TTV open reading frames, most particularly from ORF1 or ORF2, and also fragments of the full length ORF1 and ORF2-encoded proteins.

BACKGROUND OF THE INVENTION

Torque Teno Virus ("TTV"), also referred to as transfusion-transmitted virus, is generally assigned to the Circoviridae family. It is generally recognized that TTV was first isolated from human transfusion patients (see for example, Nishizawa et al., Biochem. Biophys. Res. Comm. vol. 241, 1997, pp. 92-97). Subsequently, TTV or TTV-like viruses have been identified from other mammals, including swine, and numerous strains or isolates have been published (see for example, McKeown et al. Vet. Microbiol. vol. 104, 2004, pp 113-117).

Subsequent work as shown that TTV and TTV-like viruses are very common; however the pathogenesis of TTV, and the contributions it may make to other disease states (for example, those caused by other viruses and bacteria) remains unclear. For example, TTV infections appear to be common in humans, including even in healthy individuals, and such infections are often asymptomatic, and may remain for years. In addition, the general inability to propagate the virus in cell culture, and a lack of any clear mechanistic disease models, have made any overall characterization of TTV biology difficult. Notwithstanding that TTV viremia is elevated in human patients afflicted with other viral diseases, (such as hepatitis or HIV/AIDS), there is also considerable medical literature suggesting that TTVs are, in fact, avirulent, and await any clear actual association with known disease states. See, for example, Biagini et al., Vet. Microbiol. vol. 98, 2004, pp. 95-101.

In regard of swine, the situation is similar. There is considerable work suggesting that TTV infection is associated with, and contributes to, numerous diseases such as porcine circovirus disease (and its various clinical manefestations, such as postweaning multisystemic wasting syndrome and respiratory disease complicated by lung lesions), and PRRSV-associated disease (porcine respiratory and reproductive syndrome virus). See for example published international patent applications WO 2008/150275 and WO 2008/127279. Krakowka et al. also report on an often fatal disease in pigs referred to as PDNS (porcine dermatitis and neuropathy syndrome) which is described as a manifestation of disseminated intravascular coagulation, and for which combined infection by serotype 1 TTV and PRRSV virus was possibly implicated (Am. J. Vet Res, vol 69(12), 2008, pp. 1615-1622. PDNS disease was also correlated with porcine circovirus disease (notably PCV-2) and also with bacterial infections. Accordingly, while considerable work has been accomplished, there remains little work that definitively correlates porcine TTV infection with specific pathologies. Nonetheless, it has become reasonably clear that TTV infection can potentiate numerous disease states. Accordingly, there is a need for various classes of TTV reagents, such as high affinity antibodies, and for example, peptide fragments of TTV or whole virions that are highly immunizing, both to further our understanding of overall TTV biology and to vaccinate, directly or indirectly, against numerous disease states to which TTV may contribute.

Thus, although the possibility exists that TTV is the principle causative factor of diseases in swine, it seems more likely that numerous swine diseases either require the presence of more than one virus, or that the primary effect of certain "primary" pathogens is potentiated by TTV infection. As stated, the possibility exists that numerous diseases of swine can be treated or lessened by administering anti-TTV agents to affected or potentially affected animals. Notwithstanding the well established interest in TTV, effective vaccines have not emerged.

TTV is a small, non-enveloped virus comprised of negative polarity, single-strand circularized DNA. The genome includes three major open reading frames, ORF1, ORF2 and ORF3, which overlap, and ORF1 encodes the capsid protein. (Biagini et al., supra). For a detailed discussion thereof, please see the following references, which are incorporated by reference: Kakkola et al., Virology, vol. 382 (2008), pp. 182-189; Mushahwar et al., Proc. Natl. Acad. Sci, USA, vol 96, (1999) pp. 3177-3182; and T. Kekarainen and J. Segales, "Torque teno virus infection in the pig and its potential role as a model of human infection", The Veterinary Journal, accepted Dec. 13, 2007 for 2008.

Despite the relatively simple genome, it has been generally very difficult to propagate the virus in cell culture or by other in vitro methods. The present invention is directed to recombinant constructs whereby TTV can be propagated in vitro, including via infectious clones. More particularly, the invention is directed to the discovery that effective vaccines can in fact be made from TTV, most particularly when the TTV antigen is the expression product of a single ORF, or a fragment thereof. In a preferred embodiment, the invention provides for ORFI protein vaccines.

SUMMARY OF THE INVENTION

The present invention provides a method of treating or preventing a disease or disorder in an animal caused by infection with torque teno virus (TTV), including disease states that are directly caused by TTV, and disease states contributed to or potentiated by TTV. In a preferred example, the animal treated is a swine. Disease states in swine that may be potentiated by TTV, and which may also be treated or prevented according to the practice of the invention, include those caused by or associated with porcine circovirus (PCV), and porcine reproductive and respiratory syndrome virus (PRRS).

The present invention also includes the option to administer a combination vaccine, that is, a bivalent or multivalent combination of antigens, which may include live, modified live, or inactivated antigens against the non-TTV pathogen, with appropriate choice of adjuvant.

Based in part upon the unique TTV amino acid sequences as disclosed herein, the present invention also provides a diagnostic kit for differentiating between porcine animals vaccinated with the above described TTV vaccines and porcine animals infected with field strains of TTV.

Representative embodiments of the invention include an isolated polynucleotide sequence that comprises a polynucleotide selected from the group consisting of:

($a_1$) the DNA of genotype 2 sequence TTV13 (SEQ ID NO: 1); the DNA genotype 2 sequence TTV10 (SEQ ID NO: 2); or a fragment thereof than encodes the TTV capsid protein or a fragment of said protein;

($a_2$) the DNA of a genotype 1 sequence selected from the group consisting of ttvg1-7 (SEQ ID NO: 4), ttvGT1-17 (SEQ ID NO: 5), ttvGT1-21 (SEQ ID NO: 6), ttvgt1-27 (SEQ ID NO: 3), ttvgt1-178 (SEQ ID NO: 7) or a fragment thereof than encodes the TTV capsid protein or a fragment of said protein;

(b) the complement of any sequence in (a);

(c) a polynucleotide that hybridizes with a sequence of (a) or (b) under stringent conditions defined as hybriding to filter bound DNA in 0.5M $NaHPO_4$, 7% SDS, 1 mM EDTA at 65° C., and washing in 0.1×SSC/0.1% SDS at 68° C.;

(d) a polynucleotide that is at least 70% identical to the polynucleotide of (a) or (b);

(e) a polynucleotide that is at least 80% identical to the polynucleotide of (a) or (b);

(f) a polynucleotide that is at least 90% identical to the polynucleotide of (a) or (b); and (g) a polynucleotide that is at least 95% identical to the polynucleotide of (a) or (b).

The invention further provides RNA polynucleotide molecules that are the complement of any such DNA polynucleotide sequence, and vectors and plasmids for the expression of any such RNA or DNA polynucleotides, and for TTV virus that is expressed from such nucleotide sequences, wherein said virus is live, or fully or partially attenuated.

The invention also provides a DNA vaccine that comprises a polynucleotide sequence as aforementioned, and corresponding nucleotide sequences that function as infectious clones.

The invention provides a polypeptide encoded by any of the open reading frames of the genotype 2 TTV13 (SEQ ID NO:1) or genotype 2 TTV10 (SEQ ID NO: 2) polynucleotides, or a polypeptide that is at least 90% identical thereto, or to a fragment thereof, including the option that additional otherwise identical amino acids are replaced by conservative substitutions.

The invention also provides a polypeptide encoded by any of the open reading frames of the (all sertotype 1) ttvg1-7 (SEQ ID NO:10), ttvGT1-17 (SEQ ID NO:11), ttvGT1-21 (SEQ ID NO:12), ttvgt1-27 (SEQ ID NO:13), and ttvgt1-178 (SEQ ID NO:9) ORF1 polynucleotides, or a polypeptide that is at least 90% identical thereto, or to a fragment thereof, including the option that additional otherwise identical amino acids are replaced by conservative substitutions.

Despite continued failures as reported in the art, to provide effective vaccines against TTV (or to limit the ability of TTV to potentiate other diseases), the present invention provides for such effective vaccines, which preferably comprise a polypeptide resultant from expression of a single TTV open reading frame, or a mixture thereof. In a preferred embodiment, the polypeptide is expressed from ORF1, and preferred mixtures include a combination of the polypeptides of ORF1 and ORF2, and ORF1 and ORF3.

In a further preferred embodiment, and taking advantage of the substantial polypeptide sequence information disclosed herein, there are further provided polypeptide vaccines wherein the antigen is defined by (a) the first 100 N-terminal amino acids of the capsid protein of TTV13 (SEQ NO:1) or TTV10 (SEQ ID NO:2); or (b) an amino acid sequence that is at least 90 percent identical thereto; or (c) an arginine rich region thereof.

BRIEF DESCRIPTION OF THE DRAWINGS

FIG. 4 provides a phylogenetic tree for various TTV strains including a compilation of percent identities.

FIG. 5 (panels A, B and C) provides identification of in-common arginine rich regions of ORF1 proteins as expressed from various TTV isolates. Full length ORF1 amino acid sequences are presented and aligned for strains ttvgt1-178, ttvgt1-7, ttvgt1-17, ttvgt1-21, ttvgt1-27, gt2 TTV10 and gt2 TTV13 (SEQ ID NO:9 through SEQ ID NO:15, consecutively). To depict the complete ORF1 amino acid sequences, the information is split into Panels A, B and C, with Panel A covering approximately residues 1-240, Panel B approximately residues 240-480, and Panel C approximately residues 480-670.

BRIEF DESCRIPTION OF THE SEQUENCE LISTINGS

Figures 1A, 1B:
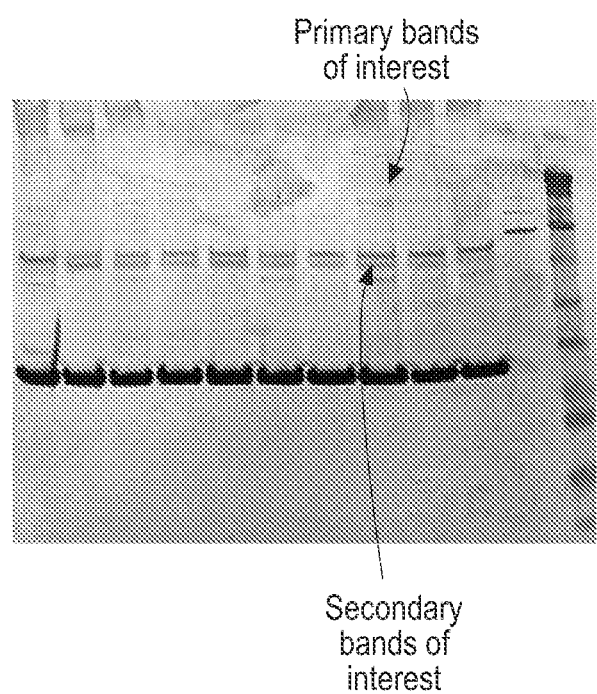
FIG. 1 (panels A and B) shows detection of ORF1 protein by immunological methods.

SEQ ID NO:1 provides the genotype gt2 TTV 10 DNA sequence.

SEQ ID NO:2 provides the genotype 2 gt2 TTV 13 DNA sequence.

SEQ ID NO:3 provides the genotype 1 ttvgt1-27 DNA sequence.

SEQ ID NO:4 provides the genotype 1 ttvgt1-7 DNA sequence.

SEQ ID NO:5 provides the genotype 1 ttvgt1-17 DNA sequence.

SEQ ID NO:6 provides the genotype 1 ttvgt1-21 DNA sequence.

SEQ ID NO:7 provides the genotype 1 ttvg1-178 DNA sequence SEQ ID NO:8 provides the amino acid sequence of TTV strain AY823991 ORF1.

SEQ ID NO:9 provides the amino acid sequence of TTV strain ttvgt1-178 ORF1 (TTV genotype 1).

SEQ ID NO:10 provides the amino acid sequence of TTV strain ttvgt1-7 ORF1.

SEQ ID NO:11 provides the amino acid sequence of TTV strain ttvgt1-17 ORF1.

SEQ ID NO:12 provides the amino acid sequence of TTV strain ttvgt1-21 ORF1.

SEQ ID NO:13 provides the amino acid sequence of TTV strain ttvgt1-27 ORF1.

SEQ ID NO:14 provides the amino acid sequence of TTV strain gt2 TTV10 ORF1 (genotype 2).

SEQ ID NO:15 provides the amino acid sequence of TTV strain gt2 TTV13 ORF1

SEQ ID NO:16 provides the DNA sequence of known strain AY823991 (genotype 2).

SEQ ID NO:17 provides the DNA sequence of known strain AY823990 (genotype 1).

SEQ ID NO:18 provides the 76057-3 TTV capsid encoding sequence, codon optimized for *E. coli.* as cloned into the pUC57 GenScript® vector.

SEQ ID NO:19 provides the 76057-4 TTV capsid encoding sequence, codon optimized for *E. coli.* as cloned into the Invitrogen pET101/D-TOPO® expression plasmid.

SEQ ID NO:20 provides the 76057-5 TTV capsid encoding sequence, codon optimized for *Saccharomyces cerevisiae* as cloned into the pUC57 GenScript® vector.

SEQ ID NO:21 provides the DNA sequence for a construct that encodes ttvgt1-7 ORF1 with a yeast invertase expression tag (Yl).

SEQ ID NO:22 provides a ttvgt1 peptide sequence (numbering based on the corresponding AY823990 sequence) from the ORF1 capsid protein corresponding to residues 167-185, which is used with the C-terminal AA in amidated form.

SEQ ID NO:23 provides a ttvgt1 peptide sequence (numbering based on the corresponding AY823990 sequence) from the ORF1 capsid protein corresponding to residues 459-479.

SEQ ID NO:24 provides a ttvgt1 peptide sequence (numbering based on the corresponding AY823990 sequence) from the ORF1 capsid protein corresponding to residues 612-637.

SEQ ID NO:25 provides the amino acid sequence of TTV strain AY823990 ORF1.

SEQ ID NOS:26-29 define primer sequences.

In connection with the descriptors for the sequences, those familiar with the art will recognize that numerous slightly different abbreviations are commonly used interchangeably for specific serotypes, for example, g1TTV, TTVg1, genotype 1 TTV, serotype 1 TTV, gt1TTV, and the like. A similar situation exists for genotype 2.

DETAILED DESCRIPTION OF THE INVENTION

The Following Definitions and Introductory Matters are Applicable in the Specification The terms "porcine" and "swine" are used interchangeably herein and refer to any animal that is a member of the family Suidae such as, for example, a pig. "Mammals" include any warm-blooded vertebrates of the Mammalia class, including humans.

An "infectious DNA molecule", for purposes of the present invention, is a DNA molecule that encodes the necessary elements for viral replication, transcription, and translation into a functional virion in a suitable host cell.

Likewise, an "isolated polynucleotide molecule" refers to a composition of matter comprising a polynucleotide molecule of the present invention purified to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refers to sense and anti-sense strands, and in all cases to the complement of any such strands. For purposes of the present invention, a polynucleotide molecule is useful in practicing the present invention, and is therefore homologous or has identity, where it can be used as a diagnostic probe to detect the presence of TTV virus or viral polynucleotide in a fluid or tissue sample of an infected pig, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova T A and T L Madden, "BLAST 2 sequences—a new tool for comparing protein and nucleotide sequences." (1999) FEMS Microbiol Lett. 174:247-250.]. Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 89:10915-10919. 1992). The percent identity is then calculated as: Total number of identical matches×100/ divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% and 95% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4) glycine and proline, (5) isoleucine, leucine and valine, (6) methionine, leucine and isoleucine, (7) phenylalanine, methionine, leucine, and tyrosine, (8) serine and threonine, (9) tryptophan and tyrosine, (10) and for example tyrosine, tyrptophan and phenylalanine.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a TTV virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, New York (1989), pp. 9.47 to 9.51.

In another embodiment, a second nucleotide sequence is homologous to SEQ ID NO:1 (or any other sequence of the invention) if it hybridizes to the complement of SEQ ID NO:1 under highly stringent conditions, e.g. hybridization to filter-bound DNA in 0.5 M NaHPO$_4$, 7% SDS, 1 mM EDTA at 65° C., and washing in 0.1×SSC/0.1% SDS at 68° C., as is known in the art.

It is furthermore to be understood that the isolated polynucleotide molecules and the isolated RNA molecules of the present invention include both synthetic molecules and molecules obtained through recombinant techniques, such as by in vitro cloning and transcription.

Polypeptides and Polynucleotides of the Invention

Representative embodiments of the invention include an isolated polynucleotide sequence that comprises a polynucleotide selected from the group consisting of:

(a$_1$) the DNA of genotype 2 sequence TTV13 (SEQ ID NO: 1); the DNA genotype 2 sequence TTV10 (SEQ ID NO: 2); or a fragment thereof than encodes the TTV capsid protein or a fragment of said protein;

(a$_2$) the DNA of a genotype 1 sequence selected from the group consisting of ttvg1-7 (SEQ ID NO: 4), ttvGT1-17 (SEQ ID NO: 5), ttvGT1-21 (SEQ ID NO: 6), ttvgt1-27 (SEQ ID NO: 3), ttvgt1-178 (SEQ ID NO: 7) or a fragment thereof than encodes the TTV capsid protein or a fragment of said protein;

(b) the complement of any sequence in (a);

(c) a polynucleotide that hybridizes with a sequence of (a) or (b) under stringent conditions defined as hybriding to filter bound DNA in 0.5M NaHPO$_4$, 7% SDS, 1 mM EDTA at 65° C., and washing in 0.1×SSC/0.1% SDS at 68° C.;

(d) a polynucleotide that is at least 70% identical to the polynucleotide of (a) or (b);

(e) a polynucleotide that is at least 80% identical to the polynucleotide of (a) or (b);

(f) a polynucleotide that is at least 90% identical to the polynucleotide of (a) or (b); and (g) a polynucleotide that is at least 95% identical to the polynucleotide of (a) or (b).

The invention also provides a polypeptide encoded by any of the open reading frames of the genotype 2 TTV13 (SEQ ID NO:1) or genotype 2 TTV10 (SEQ ID NO:2) polynucleotides, or a polypeptide that is at least 90% identical thereto, or to a fragment thereof, including the option that additional otherwise identical amino acids are replaced by conservative substitutions.

The invention also provides a polypeptide encoded by any of the open reading frames of the (all sertotype 1) ttvg1-7 (SEQ ID NO:10), ttvGT1-17 (SEQ ID NO:11), ttvGT1-21 (SEQ ID NO:12), ttvgt1-27 (SEQ ID NO:13), and ttvgt1-178 (SEQ ID NO:9) ORF1 polynucleotides, or a polypeptide that is at least 90% identical thereto, or to a fragment thereof, including the option that additional otherwise identical amino acids are replaced by conservative substitutions.

In a preferred embodiment, the polypeptide is expressed from ORF1, and preferred mixtures include a combination of the polypeptides of ORF1 and ORF2, and ORF1 and ORF3.

In a further preferred embodiment, there are further provided TTV polypeptide-based vaccines wherein the antigen is defined by:

(a) the first 300 N-terminal amino acids of the ORF1 capsid protein of TTV13 (SEQ NO:1) or TTV10 (SEQ ID NO:2); or
(b) an amino acid sequence that is at least 90 percent identical thereto;
(b) the first 200 N-terminal amino acids of the ORF1 capsid protein of TTV13 (SEQ NO:1) or TTV10 (SEQ ID NO:2); or
(b) an amino acid sequence that is at least 90 percent identical thereto;
(c) the first 100 N-terminal amino acids of the ORF1 capsid protein of TTV13 (SEQ NO:1) or TTV10 (SEQ ID NO:2); or
(b) an amino acid sequence that is at least 90 percent identical thereto;
(d) the first 300 N-terminal amino acids of the ORF1 capsid protein of any of (all sertotype 1) ttvg1-7 (SEQ ID NO:10), ttvGT1-17 (SEQ ID NO:11), ttvGT1-21 (SEQ ID NO:12), ttvgt1-27 (SEQ ID NO:13), and ttvgt1-178 (SEQ ID NO:9) or a polypeptide that is at least 90% identical thereto;
(e) the first 200 N-terminal amino acids of the ORF1 capsid protein of any of (all sertotype 1) ttvg1-7 (SEQ ID NO:10), ttvGT1-17 (SEQ ID NO:11), ttvGT1-21 (SEQ ID NO:12), ttvgt1-27 (SEQ ID NO:13), and ttvgt1-178 (SEQ ID NO:9) or a polypeptide that is at least 90% identical thereto; and
(f) the first 100 N-terminal amino acids of the ORF1 capsid protein of any of (all sertotype 1) ttvg1-7 (SEQ ID NO:10), ttvGT1-17 (SEQ ID NO:11), ttvGT1-21 (SEQ ID NO:12), ttvgt1-27 (SEQ ID NO:13), and ttvgt1-178 (SEQ ID NO:9) or a polypeptide that is at least 90% identical thereto.

Further Genetic Manipulations

The DNA and amino acid sequence information provided by the present invention also makes possible the systematic analysis of the structure and function of the viral genes and their encoded gene products. Knowledge of a polynucleotide encoding a viral gene product of the invention also makes available anti-sense polynucleotides which recognize and hybridize to polynucleotides encoding a polypeptide of the invention, or a fragment thereof. Full length and fragment anti-sense polynucleotides are useful in this respect. The worker of ordinary skill will appreciate that fragment antisense molecules of the invention include (i) those which specifically recognize and hybridize to a specific RNA (as determined by sequence comparison of DNA encoding a viral polypeptide of the invention as well as (ii) those which recognize and hybridize to RNA encoding variants of the encoded proteins. Antisense polynucleotides that hybridize to RNA/DNA encoding other TTV peptides are also identifiable through sequence comparison to identify characteristic, or signature sequences for the family of molecules. Such techniques (see Example 8) are further of use in the study of antigenic domains in TTV polypeptides, and may also be used to distinguish between infection of a host animal with remotely related non-TTV members of the Circoviridae.

Example 4 provides guidance as to effective codon optimization for enhanced expression in yeast and *E. coli* for the constructs of the invention.

Vaccine Formulations

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's *Pharmaceutical Science*, 18th ed., 1990, Mack Publishing, which is incorporated herein by reference.

Vaccines of the present invention may further comprise one or more additional immunomodulatory components such as, e.g., an adjuvant or cytokine, among others. Non-limiting examples of adjuvants that can be used in the vaccine of the present invention include the RIBI® adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21® (Cambridge Biotech Inc., Cambridge Mass.), SAF-M® (Chiron, Emeryville Calif.), AMPHIGEN® adjuvant, saponin, Quil A or other saponin fraction, monophosphoryl lipid A, ionic polysaccharides, and Avridine lipid-amine adjuvant. Non-limiting examples of oil-in-water emulsions useful in the vaccine of the invention include modified SEAM62® and SEAM 1/2® formulations. Modified SEAM62® is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2® is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Additional adjuvant systems permit for the combination of both T-helper and B-cell epitopes, resulting in one or more types of covalent T-B epitope linked structures, with may be additionally lipidated, such as those described in WO 2006/084319, WO2004/014957, and WO2004/014956.

In a preferred embodiment of the present invention, ORFI TTV protein, or other TTV proteins or fragments thereof, is formulated with 5% AMPHIGEN®.

Vaccines of the present invention can optionally be formulated for sustained release of the virus, infectious DNA molecule, plasmid, or viral vector of the present invention. Examples of such sustained release formulations include virus, infectious DNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the virus, plasmid, or viral vector can be microencapsulated to improve administration and efficacy.

Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, viral protein, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, viral protein plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies (see, for example, Examples 2 and 3 below).

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, protein, infectious DNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 µg to about 100 mg, more preferably from about 1 µg to about 10 mg, even more preferably from about 10 µg to about 1 mg. The dose amount of an infectious DNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

Suitable doses for viral protein or peptide vaccines according to the practice of the present invention range generally from 1 to 50 micrograms per dose, or higher amounts as may be determined by standard methods, with the amount of adjuvant to be determined by recognized methods in regard of each such substance. In a preferred example of the invention relating to vaccination of swine, an optimum age target for the animals is between about 1 and 21 days, which at pre-weening, may also correspond with other scheduled vaccinations such as against *Mycoplasma hyopneumoniae*. Additionally, a preferred schedule of vaccination for breeding sows would include similar doses, with an annual revaccination schedule.

Antibodies

Also contemplated by the present invention are anti-TTV antibodies (e.g., monoclonal and polyclonal antibodies, single chain antibodies, chimeric antibodies, humanized, human, porcine, and CDR-grafted antibodies, including compounds which include CDR sequences which specifically recognize a TTV polypeptide of the invention. The term "specific for" indicates that the variable regions of the antibodies of the invention recognize and bind a TTV polypeptide exclusively (i.e., are able to distinguish a single TTV polypeptide from related polypeptides despite sequence identity, homology, or similarity found in the family of polypeptides), and which are permitted (optionally) to interact with other proteins (for example, *S. aureus* protein A or other antibodies in ELISA techniques) through interactions with sequences outside the variable region of the antibodies, and in particular, in the constant region of the Ab molecule. Screening assays to determine binding specificity of an antibody of the invention are well known and routinely practiced in the art. For a comprehensive discussion of such assays, see Harlow et al. (Eds), *Antibodies A Laboratory Manual*; Cold Spring Harbor Laboratory; Cold Spring Harbor, N.Y. (1988), Chapter 6. Antibodies that recognize and bind fragments of the TTV polypeptides of the invention are also contemplated, provided that the antibodies are first and foremost specific for, as defined above, a TTV polypeptide of the invention from which the fragment was derived.

For the purposes of clarity, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. Antibodies can exist in a variety of forms including, for example, as, Fv, Fab', F(ab')$_2$, as well as in single chains, and include synthetic polypeptides that contain all or part of one or more antibody single chain polypeptide sequences.

Diagnostic Kits

The present invention also provides diagnostic kits. The kit can be valuable for differentiating between porcine animals naturally infected with a field strain of a TTV virus and porcine animals vaccinated with any of the TTV vaccines described herein. The kits can also be of value because animals potentially infected with field strains of TTV virus can be detected prior to the existence of clinical symptoms and removed from the herd, or kept in isolation away from naïve or vaccinated animals. The kits include reagents for analyzing a sample from a porcine animal for the presence of antibodies to a particular component of a specified TTV virus. Diagnostic kits of the present invention can include as a component a peptide or peptides from ORF1, 2, or 3 which is present in a field strain but not in a vaccine of interest, or vice versa, and selection of such suitable peptide domains is made possible by the extensive amino acid sequencing as provided for in Examples 1 and 2 of the Specification. As is known in the art, kits of the present invention can alternatively include as a component a peptide which is provided via a fusion protein. The term "fusion peptide" or "fusion protein" for purposes of the present invention means a single polypeptide chain consisting of at least a portion of a TTV virus protein, preferably of ORF1, and a heterologous peptide or protein.

EXAMPLES

Example 1

Cloning of Swine TTV Complete Genome

A. TTV Genotype 2.

DNA was purified from porcine serum using a DNA blood mini kit (Qiagen) per manufacturer's protocol. DNA was eluted from the columns in 50 µL Tris-EDTA buffer. DNA was then amplified via random primed rolling circle amplification. Briefly, 5 uL of purified DNA and 100 ng random hexamers (Invitrogen) were then added to 71 µl water and heated at 95 C for 3 min and cooled on ice. One mM dNTP's, 100 ng random hexamers (Invitrogen), 1×phi29 polymerase buffer and 1 µL of phi29 polymerase were then added and the reaction was incubated overnight at 30 C.

One-fifth total volume was digested with EcoRI and electrophoresed on 0.8% E-gel (Invitrogen) to detect presence of 2.7 kB fragment. EcoRI digested material was purified using a Qiagen PCR purification kit following manufacturer's protocol, and ligated into an EcoRI digested/shrimp alkaline phosphatase-treated pGem3zf(+) vector (Promega). Ligated DNA was used to transform chemically competent *E. coli* DH5a. Transformed *E. coli* was selected on LB/amp agar plates.

Plasmid DNA was isolated from transformed colonies and digested with EcoRI to confirm presence of an approximately 2.7 kB insert. Four clones (4, 7, 10 and 13) were selected and submitted to ACGT, Inc. for sequencing. Alignment of sequence data indicated that clones 10 and 13 demonstrated homology to TTV published sequence and aligned more closely to TTV genotype 2 than genotype 1. These clones were subsequently named TTV10 and TTV13.

Analyses of Sequencing Data for PAH TTV Genotype 2.

Nucleotide Alignment of TTV13 (SEQ ID NO:2) and TTV10 (SEQ ID NO:1) to published TTV genotype 2 AY823991 DNA sequence (SEQ ID NO:16).

```
AY823991   (1)  TCATGACAGGGTTCACCGGAAGGGCTGCAAAA-TTACAGCTAAAACCACA

TTV13      (1)  TAATGACAGGGTTCACCGGAAGGGCTGCAAAA-TTACAGCTAAAACCACA

TTV10      (1)  TAATGACAGGGTTC-CAGGAAGTGCTGCAAAAATTACAGCTAAAACCACA

AY823991  (50)  AGT-CTAACACAATAAACCACAAAGTATTACAGGAAACTGCAATAAATTT

TTV13     (50)  AAT-CTAACACAATAAACCACAAAATATTACAGGAAACTGCAATAAATTT

TTV10     (50)  ACTACTTACACAT--AACCACAAAATATTTCAGGAAACTGCAATAATTTT

AY823991  (99)  AGAAATAAGTTACACATAACCACCA-----------AACCACAGGAAAC
```

-continued

```
TTV13     (99)  AGAAATAAATTACACATAACCACCA------------AACCACAGGAAAC
TTV10     (98)  CAACACACATTGCACAAAACCACAAGATATCAACATAAACCACAGGAAAC

AY823991 (137)  TGTGCAAAAAGAGGAAATAAATTTCATTGGCTGGGCCTGAAGTCCTCAT
TTV13    (137)  TCTGCAAAAAGAGGAAATAAATTTCATTGGCTGGTCCATAAGTCCTCAT
TTV10    (148)  TCTGCAAAAAGAGGAAGTAAATGCTATTGGCTAAATCTGAAGTCTTCAT

AY823991 (187)  TAGAATAATAAAAGAACCAATCAGAAGAACTTCCTCTTTTAGAGTATATA
TTV13    (187)  TAGAATACAAAAGAACCAATCAGAAACACTTCCTCTTTTAGAGTATATA
TTV10    (198)  TAGCATACACAACCAACCAATCAGAAACACTTCCTCATTTGAAGTATATA

AY823991 (237)  AGTAAGTGCGCAGACGAATGGCTGAGTTTATGCCGCTGGTGGTAGACACG
TTV13    (237)  AGTAAGTGCGCAGACGAATGGCTGAGTTTATGCCGCTGGTGGTAGACACG
TTV10    (248)  AGTAAATGCGCAGACGAATGGCTGAGTTTATGCCGCTGGTGGTAGACACG

AY823991 (287)  AACAGAGCTGAGTGTCTAACCGCCTGGGCGGGTGCCGGAGCTCCTGAGAG
TTV13    (287)  AACAGAGCTGAGTGTCTAACCGCCTGGGCGGGTGCCGGAGCTCCTGAGAG
TTV10    (298)  AACAGAGCTGAGTGTCTAACCGCCTGGGCGGGTGCCGGAGCTCCAGAGAG

AY823991 (337)  CGGAGTCAAGGGGCCTATCGGGCAGGCGGTAATCCAGCGGAACCGGGCCC
TTV13    (337)  CGGAGTCAAGGGGCCTATCGGGCAGGCGGTAATCCAGCGGAACCGGGCCC
TTV10    (348)  CGGAGTCAAGGGGCCTATCGGGCGGGCGGTAATCCAGCGGAACCGGGCCC

AY823991 (387)  CCC-TCGATGGAAGAAAGATGGCTGACGGTAGCGTACTGCGCACACGGAT
TTV13    (387)  CCCCTCCATGGAAGAAAGATGGCTGACGGTAGCGTACTGCGCCCACGGAT
TTV10    (398)  CCC-TCCATGGAGGAGAGATGGCTGACGGTAGCGTACGCCGCCCACGGAT

AY823991 (436)  TATTCTGCAGCTGTAAAGACCCGAAAAAACATCTTGAAAAATGCCTTACA
TTV13    (437)  TATTCTGCGACTGTAAAGACCCGAAAAAACATCTTGAAAAATGCCTTACA
TTV10    (447)  TATTCTGCGCCTGCAGTAAGCCCAAAGACCACCTTGAAAAATGCCTTTCC

AY823991 (486)  GACGCTATCGCAGACGCCGAAGAAGACCGACACGGAGATGGAGGCACCGG
TTV13    (487)  GACGCTATCGCAGACGCCGAAGGAGACCGACAAGAAGATGGAGGCACCGG
TTV10    (497)  ACCGCTATCGCCGACGCCGAAGGAGACCCACCAGGAGATGGAGGAGAAGG

AY823991 (536)  AGGTGGAGACGCTACTTTCGATATCGGTATCGACGCGCTCCTCGCCGCCG
TTV13    (537)  AGGTGGAGACGCTACTTTCGATATCGGTATCGACGCGCTCCTCGCCGCCG
TTV10    (547)  AGGTTCCAGCGCTACTTTCGATATCGGTATAGACGCGCTCCTCGCCGCCG

AY823991 (586)  CCG---CACAAAGGTAAGGAGACGGAGG---AAAAAAGCTCCGGTCATAC
TTV13    (587)  CCG---CACAAAGGTAAGGAGACGGAGG---AGGAAAGCTCCGGTCATAC
TTV10    (597)  CCGACGCTACAAGGTAAGGAGACGGAGGGTTAAAAAGGCTCCGGTCATTC

AY823991 (630)  AATGGTTCCCTCCTAGCCGGAGAACCTGCCTCATAGAGGGATTTTGGCCG
TTV13    (631)  AATGGAACCCTCCTAGCCGGAGGACCTGCCTCATAGAGGGGTTCTGGCCG
TTV10    (647)  AATGGTTCCCCCCAACAGTCAGAAACTGTTTTATCAAGGGAATCTGGCCG

AY823991 (680)  TTGAGCTACGGACACTGGTTCCGTACCTGTCTCCCCTTTAGGCGGTTAAA
TTV13    (681)  TTGAGCTACGGACACTGGTTCCGTACCTGTCTCCCCTTTAGAAGAAAAAA
TTV10    (697)  TTGAGCTACGGACACTGGCTCCGTACCTGTCTCCCTATGAGAAAAGAAAA

AY823991 (730)  TGGACTAGTATTCCCGGGTGGAGGTTGTGACTGGAGCCAGTGGAGTTTAC
TTV13    (731)  TGGACTAATATTTACGGGAGGAGGTTGTGACTGGACTCAGTGGAGCTTAC
TTV10    (747)  CGGACTCATATTCCTAGGAGGTGGCATAGACTGGACTGTCTGGAGTTTAC
```

```
AY823991  (780) AAAACCTTTACAATGAAAAACTTAACTGGAGAAATATATGGACAGCTAGT
TTV13     (781) AAAACCTTTATCATGAAAAACTAAACTGGAGAAATATATGGACAGCTAGT
TTV10     (797) AGAATCTATACCATGAAAAACTAAACTGGAGGAATGTGTGGACTTCTTCA

AY823991  (830) AATGTTGGAATGGAATTCGCTAGATTTTTAAAAGGAAAGTTTTACTTTTT
TTV13     (831) AACGTGGGAATGGAATTCGCTAGATTTTTAAAAGGAAAATTCTACTTTTT
TTV10     (847) AATGATGGCATGGAGTTCGCTAGATTCAGATATGCAAAGTTTAAATTTTT

AY823991  (880) CAGACATCCATGGAGAAATTATATAATAACTTGGGATCAAGATATACCAT
TTV13     (881) TAGACATCCTTGGAGAAACTATATAGTGACTTGGGATCAGGACATTCCTT
TTV10     (897) TAGACACACAACCAGATCCTACGTAGTAACATGGGACCAAGACATACCAT

AY823991  (930) GCAGGCCACTACCTTATCAAAACCTGCATCCACTCCTAATGCTACTAAAA
TTV13     (931) GTAAACCTTTACCATATCAGAACTTACACCCATTATTAATGCTATTAAAA
TTV10     (947) GTAAACCTTTACCATACACAAATTTACATCCATTTGTAATGCTTCTAAAA

AY823991  (980) AAACAGCACAAAATTGTACTTTCACAGCAAAACTGTAACCCAAACAGAAA
TTV13     (981) AAACAACACAAATTAGTACTCTCACAACAAAACTGTAACCCTAACAGAAA
TTV10     (997) AAACATCATAAAGTAGTTCTAAGCAAACAAGACTGTAATCCTAGAAAAAT

AY823991 (1030) ACAAAAACCTGTCACATTAAAATTCAAACCTCCGCCAAAACTAACATCAC
TTV13    (1031) ACAAAAACCTGTAACTTTAAAATTCAGACCGCCACCAAAACTAACTTCAC
TTV10    (1047) GGACAAACCAGTCACCTTAAAAATAAAGCCACCACCAAAACTCACATCAC

AY823991 (1080) AATGGAGACTAAGTAGAGAATTAGCAAAGATGCCACTAATAAGACTTGGA
TTV13    (1081) AATGGAGACTAAGTAGAGAATTAGCAAAAATGCCACTCATTAGACTAGGA
TTV10    (1097) AGTGGAGACTAAGCAGAGAATTATCAAAAATACCGCTCTTAAGACTAGGA

AY823991 (1130) GTAAGCTTTATAGACCTAACAGAACCATGGGTAGAAGGGTGGGGAAATGC
TTV13    (1131) GTTAGTTTTATAGACTTAACAGAACCGTGGCTAGAAGGTTGGGGAAATGC
TTV10    (1147) GTTTCTTTAATAGACTTCAGAGAACCATGGGTTGAAGGTTTTGGAAATGC

AY823991 (1180) ATTTTATTCCGTGCTAGGATATGAAGCAGTAAAAGACCAAGGACACTGGT
TTV13    (1181) ATTTTACTCAGTACTAGGATATGAAGCCATAAAAGAACAAGGACACTGGT
TTV10    (1197) ATTCTTTAGTACTTTAGGATATGAAGCAGATAAAAGCAATTTAAAAACAA

AY823991 (1230) CAAACTGGACACAAATAAAATACTATTGGATCTATGACACGGGAGTAGGA
TTV13    (1231) CAAATTGGTCACAAATTAAATATTACTGGATATATGATACAGGAGTAGGA
TTV10    (1247) GCGCTTGGTGCCAATGTAAATACTTCTGGATATATGATACCGGAGTAAAT

AY823991 (1280) AATGCAGTATATGTTATACTATTAAAAAAAGACGTTACTGATAATCCAGG
TTV13    (1281) AATGCTGTATATGTAGTTATGCTAAAACAAGATGTAGACGACAACCCAGG
TTV10    (1297) AATCATGTATATGTAGTCATGTTAAACAAAGACGCAGGAGATAATGCAGG

AY823991 (1330) AAACATGGCAACAACCTTTAAAGCATCAGGAGGACAGCATCCAGATGCAA
TTV13    (1331) AAAAATGGCATCAACATTTAAAACAACTCAGGGACAACATCCCAATGCTA
TTV10    (1347) AGACCTAATAACAA-----------------------ATCAAAACTCAA

AY823991 (1380) TAGATCACATTGAATTGATAAACCAAGGATGGCCTTACTGGTTATACTTT
TTV13    (1381) TAGATCACATAGAATTAATAAATGAAGGATGGCCGTACTGGTTATACTTT
TTV10    (1373) TAGCACACATAGAACAGATAGGAGAAGGTTATCCATACTGGTTATATTTT

AY823991 (1430) TATGGTAAAAGTGAACAAGACATTAAAAAAGAGGCACAC---AGCGCAGA
```

-continued

```
TTV13    (1431) TTTGGTAAAAGTGAACAAGACATAAAAAAGGAAGCACAT---AGCGCTGA

TTV10    (1423) TTTGGAAGATCTGAAAGAGACTTAAAAGCACTAGCAACTTCAAACACAAA

AY823991 (1477) AATATCAAGAGAATATACTAGAGACCCAAAATCTAAAAAACTAAAAATAG

TTV13    (1478) AATAGCAAGAGAATATGCTACAAATCCAAAATCAAAAAAACTAAAAATAG

TTV10    (1473) CATAAGAAACGAATTCAATACTAATCCTAACAGCAAAAAATTAAAAATAG

AY823991 (1527) GAATAGTAGGATGGGCATCTTCAAACTACACAACAACAGGCAGTGATCAA

TTV13    (1528) GAATAGTAGGATGGGCATCCTCTAACTTCACAACACCAGGCAGTTCACAA

TTV10    (1523) CTGTAATAGGATGGGCTAGCAGTAACAACACAGCACAAGATAGTACACAA

AY823991 (1577) AACAGTGGTGGATCAACATCAGCTATACAAGGTGGATATGTAG-----CA

TTV13    (1578) AACTCAGGGGGAAATATAGCAGCAATACAAGGAGGATACGTAG-----CA

TTV10    (1573) ---------GGAGCGAATACTCCAATAGAAGGAACATATTTAATATCACA

AY823991 (1622) TATGC-AGG-GTCCGGGGTCA--------TAGGAGCAGGGTCAATAGGAA

TTV13    (1623) TGGGC-AGGAGGACAAGGAAAACTAAATCTAGGAGCAGGATCAATAGGAA

TTV10    (1614) TGTGCTACAAACATCAGGACATACAG---CAGGAGCAGCACAAATAAATA

AY823991 (1662) ATTTATATCAACAAGGATGGCCATCTAATCAAACTGGCCTAATACAAAC

TTV13    (1672) ATTTGTACCAACAAGGATGGCCATCAAATCAAAACTGGCCAAATACAAAC

TTV10    (1661) ACCTATTCGCCTCTGGATGGCCTAACTCTCAAAACTATCCACCTTTAAAT

AY823991 (1712) AGAGACAAAACAAACTTTGACTGGGGAATACGAGGACTATGTATACTCAG

TTV13    (1722) AGAGACGAAACTAACTTTGATTGGGGACTCAGATCACTTTGTATACTAAG

TTV10    (1711) CTAGACAAAAACAACTTTGACTGGGGAAAAAGAGCGCTATGTATACTAAG

AY823991 (1762) AGATAACATGCACTTAGGAAGCCAAGAATTAGATGATGAATGCACAATGC

TTV13    (1772) AGATAACATGCAATTAGGAAATCAAGAATTAGATGATGAATGTACCATGC

TTV10    (1761) AAACAACATGAAAATTGGAAACCAAAATTTAGATGATGAGACCACTATGT

AY823991 (1812) TCACATTGTTCGGACCCTTTGTAGAAAAAGCAAATCCAATATTTGCAACA

TTV13    (1822) TCTCACTCTTTGGACCTTTTGTAGAAAAAGCAAATCCAATATTTGCAACA

TTV10    (1811) TTGCCCTCTTCGGACCCTTGGTAGAAAAAGCAAA-CTGGGAAGGCCTAGA

AY823991 (1862) ACAGACCCTAAATTCTTTAAACCTGAACTCAAAGACTATAATATAATCAT

TTV13    (1872) ACAGACCCTAAATACTTTAAACCAGAACTAAAAGACTATAATTTAATCAT

TTV10    (1860) AAAAATACCAGAA--CTAAAACCAGAACTCAAAGACTATAATATCTTAAT

AY823991 (1912) GAAATATGCCTTTAAATTTCAGTGGGGAGGACATGGCACAGAAAGATTTA

TTV13    (1922) GAAATATGCCTTTAAATTCCAGTGGGGAGGACATGGCACAGAAAGATTTA

TTV10    (1908) GAGATATAACTTTCGCTTTCAGTGGGGCGGACACGGAACAGAGACCTTCA

AY823991 (1962) AAACCAACATCGGAGACCCCAGCACCATACCCTGCCCCTTCGAACCCGGG

TTV13    (1972) AAACAACCATCGGAGACCCCAGCACCATACCCTGCCCCTTCGAACCCGGG

TTV10    (1958) AAACAAGTATTGGAGACCCCAGCCAAATACCCTGTCCCTACGGACCAGGT

AY823991 (2012) GACCGCTTCCA-CAGCGGGATACAAGACCCCTCCAAGGTACAAAACACCG

TTV13    (2022) GACCGCTTCCA-CAGCGGGATACAAGACCCCTCCAAGGTACAAAACACCG

TTV10    (2008) GAAGCCCCCAACACCTTGTCAGGA-ACCCCTCCAAGGTACACGAGGGGG

AY823991 (2061) TCCTCAACCCCTGGGACTATGACTGTGATGGGATTGTTAGAAAAGATACT

TTV13    (2071) TCCTCAACCCCTGGGACTATGACTGTGATGGGATTGTTAGAAAAGATACT

TTV10    (2057) TCCTCAATGCGTGGGATTATGACTATGATGGAATTGTTAGAAAAGACACT
```

-continued

```
AY823991  (2111) CTCAAAAGACTTCTCGAACTCCCCACAGAGACAGAGGAGGAGGAGAAGGC

TTV13     (2121) CTCAAAAGACTTCTCGAACTCCCCACAGAGACAGAGGAGGAGGAGAAGGC

TTV10     (2107) CTCAAAAGACTGCTTGCCATCCCCACAGACTC---GGAGGAGGAGAAAGC

AY823991  (2161) GTACCCACTCCTTGGACAAAAAACAGAGAAAGAGCCATTATCAGACTCCG

TTV13     (2171) GTACCCACTCCTTGGACAAAAAACAGAGAAAGAGCCATTATCAGACTCCG

TTV10     (2154) GTACCCGCTCGCTGGACCCAAAACAGAGAAATTGCCCTCCTCAGACGAAG

AY823991  (2211) ACGAAGAGAGCGTTATCTCAAGCACGAGCAGTGGATCCTCTCAAGAA---

TTV13     (2221) ACGAAGAGAGCGTTATCTCAAGCACGAGCAGTGGATCCGATCAAGAA---

TTV10     (2204) AAGGAGAGAGCGATATCAGTTCTTCGAGCGACTCATCGACGCAAGAAAGC

AY823991  (2258) GAAGAAACGCAGAGAC---GAAGACACCACAAGCCAAGCAAGCGACGACT

TTV13     (2268) GAAGAGACGCAGAGAC---GAAAGCACCACAAGCCAAGCAAGCGACGACT

TTV10     (2254) GAAGAAGAGAAGAGATACAGAAGACGACACAAGCCCTCAAAGCGAAGACT

AY823991  (2305) CCTCAAGCACCTCCAGCGGGTGGTAAAGAGGATGAAAACACTGTGATAGA

TTV13     (2315) CCTCAAGCACCTCCAGCGGGTGGTAAAGAGGATGAAAACACTGTGATAGA

TTV10     (2304) CCTCCAGCATGTCCAGCGACTGGTGAAGAGATTCAGGACCCT---ATAGA

AY823991  (2355) TAAATATAGAAACCTAGCAGACCCCTCACTCAATGTCACAGGACACATGG

TTV13     (2365) TAAATACAGAAACCTAGCAGACCCCTCACTCAATGTCACAGGACACATGG

TTTV10    (2351) CAAATACAGAAACTTAGCAGACCCCTCATTAAATGTCACAGGACATTTTG

AY823991  (2405) AAAAATTCATGCAGTTACATATTCAAACGTACAAGAAATAAGAGCTAAA

TTV13     (2415) AAAAATTCATGCAACTACATATCCAAAACATACAAGAAATAAGAGCTAAA

TTV10     (2401) AACACTTCTGCCGCTTACACTATAAAAACATAGCAGAAATCAGAGCTAGA

AY823991  (2455) AATGCTAAAAAATCCCTCAATAAACTTTACTTTTCTGATTAATAGCGGCC

TTV13     (2465) AATGCTAAAAAATCCCTCAATAAACTTTACTTTTCTGATTAATAGCGGCC

TTV10     (2451) AATGCCAAAAAAAACCTCAATAAACTATACTTTTCAGACTAAAAGAAG--

AY823991  (2505) TCCTGTGTCCAACCTATTTTTCCTAAACCCCTTCAAAATGGCGGGCGGGA

TTV13     (2515) TCCTGTGTCCAATCTATTTTTTTAAACACCCTTCAAAATGGCGGGAGGGA

TTV10     (2499) TTT--------ATTTCTTTATTTAAAACACC--------------------

AY823991  (2555) CACAAAATGGCGGAGGGACTAAGGGGGGGGCAAGCCCCCCTNNNNNNNNN

TTV13     (2565) CACAAAATGGCGGAGGGACTAAGGG----------------TGNNNNNN

TTV10     (2522) ----------------ACTA---------------------GAGGGCG

AY823991  (2605) NNNNNNNNNNNNNNNNNNNGGGGGGCGACCCCCCCGCACCCCCCCCTGCGG

TTV13     (2598) NNNNNNNNNNTAGGCTCTTCG---------CCCCCGCACCCCCC-TGCGG

TTV10     (2533) TAGCGGGGGGGGGACC-------------CCCCTGCACCCCCCCATGCGG

AY823991  (2655) GGGCTCCGCCCCCTGCACCCCCGGGAGGGGGGGAAACCCCCCCTCAACCC

TTV13     (2638) GGGCTCCGCCCCCTGCACCCCCGGGAGGGGGGGAAACCCCCCCTCAACCC

TTV10     (2570) GGGCTCCGCCCCCTGCACCCCCGGGAGGGGGGGAAACCCCCCCTCAACCC

AY823991  (2705) CCCGCGGGGG-CAAGCCCCCCTGCACCCCCC-

TTV13     (2688) CCCGCGGGGG-CAAGCCCCCCTGCACCCCCC-

TTV10     (2620) CCCGCGGGGGGGCAAGCCCCCCTGCACCCCCCC
```

|       | AB076001 | AY823990 | AY823991 | TTV13 | TTV10 |
|-------|----------|----------|----------|-------|-------|
| AB076001 |       | 72       | 49       | 49    | 48    |
| AY823990 |       |          | 48       | 48    | 48    |
| AY823991 |       |          |          | 92    | 76    |
| TTV13    |       |          |          |       | 76    |
| TTV10    |       |          |          |       |       |

Nucleotide Identity

|          | AY823991 | TTV13 | TTV10 |
|----------|----------|-------|-------|
| AY823991 |          | 92    | 76    |
| TTV13    |          |       | 76    |

TTV 13 shows 92% identity when compared with previously published AY823991 sequence. However, TTV10 only show 76% similarity between either AY823991 or TTV13 and may be considered a separate genotype.
Amino Acid Alignment of PAH TTV Genotype ORF1 for TTV10 (SEQ ID NO:14) and TTV13 (SEQ ID NO:15) with AY823991 ORF1 (SEQ ID NO:8).

```
AY823991 Orf1  (1)    MPYRRYRRRRRRPTRRWRHRRWRRYFRYRYRRAPRRRR-TKVRRR-RKKA
TTV10Orf1      (1)    MPFHRYRRRRRRPTRRWRRRRFQRYFRYRYRRAPRRRRRYKVRRRRVKKA
TTV13ORF1      (1)    MPYRRYRRRRRRPTRRWRHRRWRRYFRYRYRRAPRRRR-TKVRRR-RRKA

AY823991 Orf1  (49)   PVIQWFPPSRRTCLIEGFWPLSYGHWFRTCLPFRRLNGLVFPGGGCDWSQ
TTV10Orf1      (51)   PVIQWFPPTVRNCFIKGIWPLSYGHWLRTCLPMRKENGLIFLGGGIDWTV
TTV13ORF1      (49)   PVIQWNPPSRRTCLIEGFWPLSYGHWFRTCLPFRRKNGLIFTGGGCDWTQ

AY823991 Orf1  (99)   WSLQNLYNEKLNWRNIWTASNVGMEFARFLKGKFYFFRHPWRNYIITWDQ
TTV10Orf1      (101)  WSLQNLYHEKLNWRNVWTSSNDGMEFARFRYAKFKFFRHTTRSYVVTWDQ
TTV13ORF1      (99)   WSLQNLYHEKLNWRNIWTASNVGMEFARFLKGKFYFFRHPWRNYIVTWDQ

AY823991 Orf1  (149)  DIPCRPLPYQNLHPLLMLLKKQHKIVLSQQNCNPNRKQKPVTLKFKPPPK
TTV10Orf1      (151)  DIPCKPLPYTNLHPFVMLLKKHHKVVLSKQDCNPRKMDKPVTLKIKPPPK
TTV13ORF1      (149)  DIPCKPLPYQNLHPLLMLLKKQHKLVLSQQNCNPNRKQKPVTLKFRPPPK

AY823991 Orf1  (199)  LTSQWRLSRELAKMPLIRLGVSFIDLTEPWVEGWGNAFYSVLGYEAVKDQ
TTV10Orf1      (201)  LTSQWRLSRELSKIPLLRLGVSLIDFREPWVEGFGNAFFSTLGYEADKSN
TTV13ORF1      (199)  LTSQWRLSRELAKMPLIRLGVSFIDLTEPWLEGWGNAFYSVLGYEAIKEQ

AY823991 Orf1  (249)  GHWSNWTQIKYYWIYDTGVGNAVYVILLKKDVTDNPGNMATTFKASGGQH
TTV10Orf1      (251)  LKTSAWCQCKYFWIYDTGVNNHVYVVMLNKDAGDNAGDLITNQNS-----
TTV13ORF1      (249)  GHWSNWSQIKYYWIYDTGVGNAVYVVMLKQDVDDNPGKMASTFKTTQGQH

AY823991 Orf1  (299)  PDAIDHIELINQGWPYWLYFYGKSEQDIKKEAHS-AEISREYTRDPKSKK
TTV10Orf1      (296)  ---IAHIEQIGEGYPYWLYFFGRSERDLKALATSNTNIRNEFNTNPNSKK
TTV13ORF1      (299)  PNAIDHIELINEGWPYWLYFFGKSEQDIKKEAHS-AEIAREYATNPKSKK

AY823991 Orf1  (348)  LKIGIVGWASSNYTTTGSDQNSGG-STSAIQGGYVAYAGSG---VIGAGS
TTV10Orf1      (343)  LKIAVIGWASSNNTAQDSTQGANTPIEGTYLISHVLQTSGH---TAGAAQ
TTV13ORF1      (348)  LKIGIVGWASSNFTTPGSSQNSGG-NIAAIQGGYVAWAGGQGKLNLGAGS

AY823991 Orf1  (394)  IGNLYQQGWPSNQNWPNTNRDKTNFDWGIRGLCILRDNMHLGSQELDDEC
TTV10Orf1      (390)  INNLFASGWPSNQNYPPLNLDKNNFDWGKRALCILRNNMKIGNQNLDDET
TTV13ORF1      (397)  IGNLYQQGWPSNQNWPNTNRDETNFDWGLRSLCILRDNMQLGNQELDDEC

AY823991 Orf1  (444)  TMLTLFGPFVEKANPIFATTDPKFFKPELKDYNIIMKYAFKFQWGGHGTE
TTV10Orf1      (440)  TMFALFGPLVEKAN-WEGLEKIPELKPELKDYNILMRYNFRFQWGGHGTE
TTV13ORF1      (447)  TMLSLFGPFVEKANPIFATTDPKYFKPELKDYNLIMKYAFKFQWGGHGTE

AY823991 Orf1  (494)  RFKTNIGDPSTIPCPFEPGDRFHSGIQDPSKVQNTVLNPWDYDCDGIVRK
TTV10Orf1      (489)  TFKTSIGDPSQIPCPYGPGEAPQHLVRNPSKVHEGVLNAWDYDYDGIVRK
```

-continued

```
TTV13ORF1    (497)   RFKTTIGDPSTIPCPFEPGDRFHSGIQDPSKVQNTVLNPWDYDCDGIVRK

AY823991 Orf1 (544)  DTLKRLLELPTETEEEEKAYPLLGQKTEKEPLSDSDEESVISSTSSGSSQ

TTV10Orf1    (539)   DTLKRLLAIPTDSEEE-KAYPLAGPKTEKLPSSDEEGESDISSSSDSSTQ

TTV13ORF1    (547)   DTLKRLLELPTETEEEEKAYPLLGQKTEKEPLSDSDEESVISSTSSGSDQ

AY823991 Orf1 (594)  EEETQR--RRHHKPSKRRLLKHLQRVVKRMKTL--

TTV10Orf1    (588)   ESEEEKRYRRRHKPSKRRLLQHVQRLVKRFRTL--

TTV13ORF1    (597)   EEETQR--RKHHKPSKRRLLKHLQRVVKRMKTL--
```

Amino Acid Alignment of TTV10 TTV13 ORF with Published Sequence

|  | AY823991 Orf1 | TTV10Orf1 | TTV13ORF1 |
|---|---|---|---|
| AY823991 Orf1 |  | 65 | 92 |
| TTV10Orf1 |  |  | 66 |
| TTV13ORF1 |  |  |  |

On the amino acid level, TTV10 ORF demonstrates only 65% homology to the published sequence and may represent a unique phenotype of TTV Cloning of TTV Genotype 2 ORF1 for Baculovirus Expression Based on sequence data derived above, primers were designed to clone the ORF from TTV10 and TTV13 for expression in baculovirus using the Invitrogen Gateway® system. Primer sequences were:
For TTV13 ORF: Ttv13Rev1211: 5' cgt act cga gtc aca gtg ttt tca tcc (SEQ ID NO:26); TTV13For1211: 5' cta ggt acc atg cct tac aga cgc tat (SEQ ID NO:27)
For TTV10 ORF: tt10for 1207: 5' cta ggt acc atg cct ttc cac cgc tat (SEQ ID NO:28) and ttvrev1207: cgt act cga gct ata ggg tcc tga at (SEQ ID NO:29)

Since the EcoRI cloning into pGem® resulted in interrupting the reading frame of the ORF1, the TTV insert in pGem® was isolated by EcoRI digestion, gel-purified and re-circularized using standard ligation conditions. Following an overnight ligation at 4° C., ligase was inactivated at 65° C., and the reaction was purified using QuiQuick® purification kit (Qiagen) following the manufacturer's protocol.

TTVORF13 was the PCR amplified using re-circularized TTV13 genomic DNA with Expand Hi-Fidelity® enzyme (Roche) using the above described TTV13 forward and reverse primers (0.15 μM each), 0.2 mM dNTP's in 1×Hi Fidelity enzyme buffer. PCR conditions were: 1 cycle at 4 min, 95° C.; 35 cycles with 94° C., 15 sec denaturation, 55° C., 30 sec anneal, and 68° C. 1.5 min extension; and 1 cycle of 72° C., 7 min extension.

Similarly, TTVORF10 was PCR amplified using re-circularized TTV10 genomic DNA with Expand Hi-Fidelity® enzyme (Roche) using the above described TTV10 forward and reverse primers (0.15 μM each) 0.2 mM dNTP's in 1×Hi Fidelity enzyme buffer. PCR conditions were: 1 cycle at 4 min, 95®° C.; 35 cycles with 94° C., 15 sec denaturation, 56° C., 30 sec anneal, and 68° C. 1.5 min extension; and 1 cycle of 72° C., 7 min extension.

PCR products were purified using QiaQuick PCR purification kit (Qiagen) following the manufacturer's protocol. Both PCR TTV10Orf1 anfd TTV13Orf1 products and the Gateway entry plasmid, pENTR3C, were digested with KpnI. Digested DNA was purified using QIAquick PCR amplification kit and subsequently digested with XhoI. Following QIAquick purifications, the TTV10 ORF1 or the TTV13ORF1 DNAs were ligated into pENTR3C using standard ligation procedures. Following a 2 hour ligation at room temperature, ligated DNA was used to transform chemically competent E. coli DH5α. Transformed colonies were selected using Kanamycin. Plasmid was purified from transformed E. coli and ORF1 DNA insertion was verified by restriction fragment analysis.

pENTR3C plasmids containing TTV10 ORF1 or TTV13 ORF1 were then inserted into Invitrogen destination vectors pDEST10 or pDEST 20 encoding a His6X or a GST protein N-terminal to the TTV Orf1 reading frame. Recombinant pDEST vectors containing the open reading frame of TTV Orf1 were used to transform DH10Bac E. coli. Recombinant bacmid DNA was isolated and used for transfection of SF9 cells following standard protocol. Recombinant baculovirus containing the native Orf1 were isolated by plaque purification. Confirmation of recombinant baculovirus was performed using PCR.

Native TTVOrf1 Construction for Baculovirus Expression.

Standard PCR was used to incorporate a BamH1 restriction site upstream from the initiation codon in TTV10 Orf1 or an XbaI restriction site upstream from the initiation codon in TTV Orf13. These constructs were cloned into pFastBac transfer vector and used to transform E. coli DH10Bac. The resultant recombinant bacmids were subsequently used to transfect SF9 cells. Recombinant baculovirus containing the native Orf1 were isolated by plaque purification. Confirmation of recombinant baculovirus was performed using PCR.

Cloning of TTV Genotype 2 ORF1 for E. coli Expression.

Full-length TTVOrf10 was also cloned into a PGex-6p-1 vector for expression of a GST-fusion protein in a bacterial system. The TTV ORFs contain an arginine rich amino terminus. To determine if protein production could be increased in a bacterial expression system, the arginine rich segment was removed from TTVOrf13 at a convenient restriction site (EcoR1) located at nucleotide 368 of the Orf1 open reading frame and was in frame with the GST coding region of pGex-6p-1. This clone resulted in the removal of 100 amino-terminal amino acids containing a highly enriched arginine segment.

B. TTV Genotype 1.

Total cellular DNA from porcine bone marrow was amplified by rolling circle amplification following procedures described above, except that single-stranded binding protein was added to improve the efficiency of the amplification reaction. Amplification products were digested with EcoR1, purified using a QIAquick PCR purification kit (Qiagen), and ligated into pGem3zf(+) vector which had been previously treated with shrimp alkaline phosphatase. Recombinant vector containing putative TTV genomic DNA was selected based on restriction digests with EcoR1 and/or BamH1. Plasmids containing approximately 2.7 kB inserts were purified and submitted to ACGT, Inc. for sequencing of the ORF1 sequences to confirm genotype. The complete genome, i.e. the region containing the high G/C rich region, was not sequenced to entirety.

Analyses of Sequencing Data for PAH TTV Genotype 1

Nucleotide alignment of PAH TTV7 (SEQ ID NO:4), TTV17 (SEQ ID NO:5), TTV21 (SEQ ID NO:6), and TTV27 (SEQ ID NO:3) with published sequence, AY823990 (SEQ ID NO:17).

```
AY823990        (1)   TACACTTTGGGGTTCAGGAGGCTCAATTTGGCTCGCTTCGCTCGCACCAC
ttvg1-7         (1)   TACACTTCCGGGTTCAGGAGGCTCAATTTGGCTCGCTTCGCTCGCACCAC
ttvGT1-17       (1)   TACACTTCCGGGTTCAGGAGGCTCAATTTGGCTCGCTTCGCTCGCACCAC
ttvGT1-21       (1)   TACACTTCCGGGTTCAGGAGGCTCAATTTGGCTCGCTTCGCTCGCACCAC
ttvgt1-27       (1)   TACACTTCCGGGTTCAGAGGGCTCAATTTGGCTCGCTTCGCTCGCACCAC AY823990       (51)   GTTTGCTGCCAGGCGGACCTGATTGAAGACTGAAAACCGTTAAATTCAAA
ttvg1-7        (51)   GTTTGCTGCCAGGCGGACCTGTTTGAAGACTGAAAACCGTTAAATTCAAA
ttvGT1-17      (51)   GTTTGCTGCCAAGCGGACCTGATTGAAGACTGAAAACCGTTACATTCAAA
ttvGT1-21      (51)   GTTTGCTGCCAGGCGGACCTGATTGAAGACTGAAAACCGTTAAATTCAAA
ttvgt1-27      (51)   GTTTGCTGCCAGGCGGACCTGATTGAAGACTGAAAACCGTTAAGTTCAAA AY823990      (101)   ATTGAAAGGGCGGGCAAA-ATGGCGGACAGGGGGCGGAGTTTATGCAAA
ttvg1-7       (101)   TTTGAAATTGGCGGT-AAACATGGCGGAAGGGGGCGGAGTATATGCAAA
ttvGT1-17     (101)   TTTGAAAATGGCGCCCAAACATGGCGGATGTGGG-CGGAGTATATGCAAA
ttvGT1-21     (101)   TTTGAAATTGGCGGT-AAATATGGCGGAAGGGGGCGGAGTATATGCAAA
ttvgt1-27     (101)   TTTGAAAATGGCGCCCAAACATGGCGGAG-GGGGCGGAGTTTATGCAAA AY823990      (150)   TTAATTTATGCAAAGTAGGAGGAGCTCGATTTTAATTTATGCAAAGTAGG
ttvg1-7  . . . (150)  TTAATTTATGCAAAGTAGGAGGAGCTCGATTTTAATTTATGCAAAGTAGG
ttvGT1-17 . . . (150) TTAATTTATGCAAAGTAGGAGGAGCTCGATTTTAATTTATGCAAAGTAGG
ttvGT1-21 . . . (150) TTAATTTATGCAAAGTAGGAGGAGCTCGATTTTAATTTATGCAAAGTAGG
ttvgt1-27 . . . (150) TTAATTTATGCAAAGTAGGAGGAGCTCCATTTTAATTTATGCAAAGTAGG AY823990      (200)   AGGAGTCAAATCTGATTGGTCGGGAGCTCAAGTCCTCATTTGCATAGGGT
ttvg1-7  . . . (200)  AGGAGTCAAATCTGATTGGTCGGGAGCTCAAGTCCTCATTTGCATAGGGT
ttvGT1-17 . . . (200) AGGAGTCACTTCTGATTGGTCGGGAACTCAAGCCCTCATTTGCATAGGGT
ttvGT1-21 . . . (200) AGGAGTCAAATCTGATTGGTCGGGAGCTCAAGTCCTCATTTGCATAGGGT
ttvgt1-27 . . . (200) AGGAGTCACTTCTGATTGGTCGGGAGCTCAAGTCCTCATTTGCATAGGGT AY823990      (250)   GTAACCAATCAGAATTAAGGCGTTCCCACGAAAGCGAATATAAGTAGGTG
ttvg1-7  . . . (250)  GTAACCAATCAGAATTAAGGCGTGCCCACTAAAGTGAATATAAGTAAGTG
ttvGT1-17 . . . (250) GTAACCAATCAGAATTAAGGCGTTCCCCGTGAAGTGAATATAAGTAAGTA
ttvGT1-21 . . . (250) GTAACCAATCAGAATTAAGGCGTGCCCACTAAAGTGAATATAAGTGAGTG
ttvgt1-27 . . . (250) GTAACCAATCAAACTTAAGGCGTTCCCACTAAAGTGAATATAAGTAAGTG AY823990      (300)   AGGTTCCGAATGGCTGAGTTTATGCCGCCAGCGGTAGACAGAACTGTCTA
ttvg1-7  . . . (300)  CAGTTCCGAATGGCTGAGTTTATGCCGCCAGCGGTAGACAGAACTGTCTA
ttvGT1-17 . . . (300) AAGTTCCGAATGGCTGAGTTTATGCCGCCAGCGGTAGACAGAACTGTCTA
ttvGT1-21 . . . (300) CAGTTCCGAATGGCTGAGTTTATGCCGCCAGCGGTAGACAGAACTGTCTA
ttvgt1-27 . . . (300) CGGTTCCGAATGGCTGAGTTTATGCCGCCAGCGGTAGACAGAACTGTCTA AY823990      (350)   GCGACTGGGCGGGTGCCGGAGGATCCCTGATCCGGAGTCAAGGGGCCTAT
ttvg1-7  . . . (350)  GCGACTGGGCGGGTGCCGGAGGATCCCAGATCCGGAGTCAAGGGGCCTAT
```

-continued

```
ttvGT1-17    ...    (350) GCGACTGGGCGGGTGCCGAAGGATCCCAGATCCGGAGTCAAGGGGCCTAT
ttvGT1-21    ...    (350) GCGACTGGGCGGGTGCCGGAGGATCCCAGATCCGGAGTCAAGGGGCCTAT
ttvgt1-27    ...    (350) GCGACTGGGCGGGTGCCGGAGGATCCCTGATCCGGAGTCAAGGGGCCTAT AY823990            (400) CGGGCAGGAGCAGCTAGGCGGAGGGCCTATGCCGGAACACTGGGAGGAAG
ttvg1-7      ...    (400) CGGGCAGGAGCAGCTGAGCGGAGGGCCTATGCCGGAACACTGGGAGGAGG
ttvGT1-17    ...    (400) CGGGCAGGAGCAGCTGAGCGGAGGGCCTATGCCGGAACACTGGGAGGAGG
ttvGT1-21    ...    (400) CGGGCAGGAGCAGCTGAGCGGAGGGCCTATGCCGGAACACTGGGAAGAGG
ttvgt1-27    ...    (400) CGGGCAGGAGCAGCTGAGCGGAGGGCCTATGCCGGAACACTGGGAAGAAG AY823990            (450) CCTGGTTGGAAGCTACCAAGGGCTGGCACGATCTCGACTGCCGCTGCGGT
ttvg1-7      ...    (450) CCTGGTTGGAAGCTACCAAGGGCTGGCACGACCTTGACTGCCGCTGCGGT
ttvGT1-17    ...    (450) CCTGGTTGGAAGCTACCAAGGGCTGGCACGACCTCGACTGCCGCTGCGGT
ttvGT1-21    ...    (450) CCTGGTTGGAAGCTACCAAGGGCTGGCACGACCTTGACTGCCGCTGCGGT
ttvgt1-27    ...    (450) CCTGGTTGGAAGCTACCAAGGGCTGGCACGACTTAGACTGCCGCTGCGGT AY823990            (500) AACTGGCAGGACCACCTATGGCTCCTACTCGCCGATGGAGACGCCGCTTT
ttvg1-7      ...    (500) AATTGGCAAGACCACCTATGGCTTTTGCTCGCCGATGGAGACGCCGCTTT
ttvGT1-17    ...    (500) AACTGGCAAGACCACCTATGGCTCCTGCTCGCCGATGGAGACGCCGGCTTT
ttvGT1-21    ...    (500) AATTGGCAAGACCACCTATGGCTTTTGCTCGCCGATGGAGACGCCGCTTT
ttvgt1-27    ...    (500) AACTGGCAGGACCACCTATGGCTCCTACTCGGCGATGGAGACGCCGCTTT AY823990            (550) GGCCGCCGCCGTAGACGCTATAGAAAGAGACGCTATGGCTGGAGACGACG
ttvg1-7      ...    (550) GGCCGCCGCCGTAGACGCTATAGAAAGAGACGCTATGGATGGAGGAGACG
ttvGT1-17    ...    (550) GGCCGCCGCCGTAGACGCTATAGAAAGAGACGCTGGGGCTGGAGAAGGCG
ttvGT1-21    ...    (550) GGCCGCCGCCGTAGACGCTATAGAAAGAGACGCTATGGATGGAGGAGACG
ttvgt1-27    ...    (550) GGCCGCCGCCGTAGACGCTATAGAAAGAGACGCTATGGCTGGAGAAGACG AY823990            (600) CTACTACCGCTACAGGCCGCGTGACTATCGGCGACGATGGCTGGTAAGGA
ttvg1-7      ...    (600) CTACTACCGCTACAGACCGCGTTACTATCGGAGACGATGGCTGGTAAGGA
ttvGT1-17    ...    (600) CTACTGGAGATACCGACCGCGTTACCGTCGGCGCAGATGGCTGGTAAGGA
ttvGT1-21    ...    (600) CTACTACCGCTACAGACCGCGTTACTATCGGAGACGATGGCTGGTAAGGA
ttvgt1-27    ...    (600) CTACTACCGCTACAGACCGCGTTACTATCGGAGACGATGGCTGGTAAGGA AY823990            (650) GAAGGCGGCGTTCCGTCTACCGTAGAGGTGGACGTAGAGCGCGCCCCTAC
ttvg1-7      ...    (650) GAAGGCGGCGTTCCGTCTACCGACGAGGTGGACGTAGAGCGCGCCCCTAC
ttvGT1-17    ...    (650) GAAGGCGGCGTTCCGTCTACCGAAGAGGTGGACGTAGAGCGCGCCCCTAC
ttvGT1-21    ...    (650) GAAGGCGGCGTTCCGTCTACCGACGAGGTGGACGTAGAGCGCGCCCCTAC
ttvgt1-27    ...    (650) GAAGGCGGCGTTCCGTCTACCGTAGAGGTGGACGTAGAGCGCGCCCCTAC AY823990            (700) CGA----CTG--TTTAATCCAAAAGTAATGCGGAGAGTAGTAATTAGGGG
ttvg1-7      ...    (700) CGCATTTCTGCCTTTAATCGAAAGTAATGCGTAGAGTAGTGATTAGAGG
ttvGT1-17    ...    (700) CGTATTTCTGCTTTTAATCCAAAATAATGCGGAGAGTAGTAATAAGGGG
ttvGT1-21    ...    (700) CGCATTTCTGCCTTTAATCCGAAAGTAATGCGTAGAGTAGTGATTAGAGG
ttvgt1-27    ...    (700) CGGGTATCTGCCTTTAACCCCAAAGTAATGCGGAGAGTAGTAATAAGGGG AY823990            (744) GTGGTGGCCTATTTTACAATGCTTAAAAGGACAGGAGGCACTAAGATATA
ttvg1-7      ...    (750) GTGGTGGCCAATACTGCAGTGCCTAAAAGGTCAGGAATCACTAAGATACA
ttvGT1-17    ...    (750) ATGGTGGCCAATCCTACAATGTCTAAGAGGACAGGAATCACTAAGATATA
```

-continued

```
ttvGT1-21   ...   (750)  GTGGTGGCCAATACTGCAGTGCCTAAAAGGTCAGGAATCACTAAGATACA
ttvgt1-27   ...   (750)  GTGGTGGCCAATACTACAGTGCTTAAAAGGACAGGAATCGCTGAGATATA
AY823990          (794)  GACCTCTACAGTGGGACACAGAGAGACAGTGGAGAGTGAGATCAGACTTC
ttvg1-7     ...   (800)  GACCACTTCAGTGGGACGTAGAGAAAAGCTGGAGAATAAACACAACTCTT
ttvGT1-17   ...   (800)  GACCGTTACAGTGGGACGTAGAAAAAAGCTGGAGAATAAAGACAGACTTA
ttvGT1-21   ...   (800)  GACCACTTCAGTGGGACGTAGAGAAAAGCTGGAGAATAAACACAACTCTT
ttvgt1-27   ...   (800)  GACCACTACAGTGGGACACAGAAAGACAGTGGAGAGTGAGACAAGACTTC
AY823990          (844)  GAAGACCAGTACGGATACCTCGTACAATACGGGGGAGGTTGGGGAAGTGG
ttvg1-7     ...   (850)  GAGGACAACTATGGATACTTAGTACAGTATGGAGGTGGTTGGGGTAGCGG
ttvGT1-17   ...   (850)  GAAGACAACTACGGCTACTTAGTACAGTACGGAGGAGGTTGGGGGAGCGG
ttvGT1-21   ...   (850)  GAGGACAACTATGGATACTTAGTACAGTATGGAGGTGGTTGGGGTAGCGG
ttvgt1-27   ...   (850)  GAGGATCAATACGGATACCTGGTGCAATACGGTGGAGGTTGGGGAAGTGG
AY823990          (894)  TGATGTGACACTTGAAGGTCTCTACCAAGAGCACTTATTGTGGAGAAACT
ttvg1-7     ...   (900)  AGAGGTAACACTGGAGGGGCTGTATCAGGAGCACCTACTATGGAGAAACT
ttvGT1-17   ...   (900)  AGAGGTGACTCTAGAAGGACTGTACCAGGAACACCTACTATGGAGAAATT
ttvGT1-21   ...   (900)  AGAGGTAACACTGGAGGGGCTGTATCAGGAGCACCTACTATGGAGAAACT
ttvgt1-27   ...   (900)  TGATGTGACACTAGAGGGACTATACCAGGAACACTTACTATGGAGAAATT
AY823990          (944)  CTTGGTCTAAAGGAAACGATGGAATGGACCTAGTAAGATACTTTGGATGT
ttvg1-7     ...   (950)  CTTGGTCAAAAGGAAACGATGGGATGGACTTAGTGAGATACTTCGGCTGC
ttvGT1-17   ...   (950)  CATGGTCAAAAGGAAATGATGGAATGGATCTAGTAAGATACTTCGGCTGC
ttvGT1-21   ...   (950)  CTTGGTCAAAAGGAAACGATGGGATGGACTTAGTGAGATACTTCGGCTGC
ttvgt1-27   ...   (950)  CCTGGTCAAAAGGAAATGATGGCATGGACTTAGTGAGATACTTTGGCTGT
AY823990          (994)  GTAGTATACCTATATCCACTAAAGGACCAGGACTATTGGTTCTGGTGGGA
ttvg1-7     ...  (1000)  ATAGTATATCTATATCCGTTAAAAGATCAAGACTACTGGTTTTGGTGGGA
ttvGT1-17   ...  (1000)  ATAGTATACCTGTACCCACTGAAAGATCAGGACTACTGGTTTTGGTGGGA
ttvGT1-21   ...  (1000)  ATAGTATATCTATATCCGTTAAAAGATCAGGACTACTGGTTTTGGTGGGA
ttvgt1-27   ...  (1000)  GTGGTATACCTCTACCCACTTAAAGATCAGGACTATTGGTTCTGGTGGGA
AY823990         (1044)  CACGGACTTCAAAGAATTATATGCAGAAAACATAAAGGAATACAGCCAAC
ttvg1-7     ...  (1050)  CACAGATTTTAAAGAATTATATGCAGAGAGTATCAAAGAATACTCACAGC
ttvGT1-17   ...  (1050)  CACAGACTTTAAGGAACTCTATGCAGAAAGTATTAAGGAGTACTCACAAC
ttvGT1-21   ...  (1050)  CACAGATTTTAAGGAATTATATGCAGAGAGTATCAAAGAATACTCACAGC
ttvgt1-27   ...  (1050)  CACTGACTTTAAAGAGCTATACGCAGAAAACATAAAAGAATACAGCCAAC
AY823990         (1094)  CATCAGTAATGATGATGGCAAAAAGAACAAGAATAGTAATAGCCAGAGAA
ttvg1-7     ...  (1100)  CATCTGTAATGATGATGGCAAAAAGAACAAAAATAGTGATCGCAAGAAGT
ttvGT1-17   ...  (1100)  CATCAGTAATGATGATGGCAAAAAAAACAAAAATTGTAATAGCGAGAAGT
ttvGT1-21   ...  (1100)  CATCTGTAATGATGATGGCAAAAAGAACAAAAATAGTGATCGCAAGAAGT
ttvgt1-27   ...  (1100)  CATCAGTAATGATGATGGCAAAAAGAACTAGAATAGTAATAGCGAGAGAC
AY823990         (1144)  AGGGCACCACATAGAAGAAAAGTAAGAAAAAATATTTATTCCGCCACCTTC
ttvg1-7     ...  (1150)  AGAGCCCCACATAGAAGGAAGGTACGCAGAATTTTCATACCGCCTCCAAG
ttvGT1-17   ...  (1150)  AGGGCACCACACAGACGAAAAGTAAGAAAAAATATTCATACCGCCACCAAG
```

-continued

```
ttvGT1-21  . . .    (1150) AGAGCCCCACATAGAAGGAAGGTACGCAGAATTTTCATACCGCCTCCAAG
ttvgt1-27  . . .    (1150) AGAGCTCCACATAGAAGAAAAGTGAGAAAAATATTCATCCCACCACCATC
AY823990            (1194) GAGAGACACAACACAGTGGCAGTTTCAGACAGATTTCTGCAATAGAAAGT
ttvg1-7    . . .    (1200) TAGAGACACGACACAGTGGCAATTTCAAACTGACTTTTGCAATAGACCAC
ttvGT1-17  . . .    (1200) TAGAGACACTACACAATGGCAATTTCAAACAGAGTTCTGCAACAAACCAC
ttvGT1-21  . . .    (1200) TAGAGACACGACACAGTGGCAATTTCAAACTGACTTTTGCAATAGACCAC
ttvgt1-27  . . .    (1200) AAGAGACACTACGCAGTGGCAGTTTCAGACAGACTTCTGTAATAGGAAGC
AY823990            (1244) TATTTACGTGGGCAGCTGGTCTAATAGACATGCAAAAACCGTTCGATGCT
ttvg1-7    . . .    (1250) TATTCACATGGGCTGCAGGACTCATAGACCTCCAAAAACCATTTGACGCA
ttvGT1-17  . . .    (1250) TATTCACTTGGGCTGCAGGACTAATAGACCTCCAAAAGCCATTTGACGCA
ttvGT1-21  . . .    (1250) TATTCACATGGGCTGCAGGACTCATAGACCTCCAAAAACCATTTGACGCA
ttvgt1-27  . . .    (1250) TATTTACCTGGGCGGCAGGACTAATAGACATGCAAAAACCCTTTGATGCC
AY823990            (1294) AATGGAGCCTTTAGAAATGCTTGGTGGCTGGAACAGAGAAATGATCAGGG
ttvg1-7    . . .    (1300) AACGGTGCGTTCAGAAATGCCTGGTGGTTAGAACAGAGAAACGAGGCAGG
ttvGT1-17  . . .    (1300) AACGGAGCTTTTAGAAATGCGTGGTGGTTAGAACAGAGAAATGAGGCAGG
ttvGT1-21  . . .    (1300) AACGGTGCGTTCAGAAATGCCTGGTGGTTAGAACAGAGAAACGAGGCAGG
ttvgt1-27  . . .    (1300) AACGGAGCTTTTAGAAATGCGTGGTGGCTGGAGCAGAGAACGGAACAGGG
AY823990            (1344) AGAAATGAAATACATAGAACTGTGGGGAAGAGTACCCCCACAAGGAGATT
ttvg1-7    . . .    (1350) AGAAATGAAATACATAGAGCTATGGGGTAGAGTACCACCCCAGGGGGACA
ttvGT1-17  . . .    (1350) AGAGATGAAATACATAGAATTATGGGGGAGAGTCCCACCGCAAGGAGACA
ttvGT1-21  . . .    (1350) AGAAATGAAATACATAGAGCTATGGGGTAGAGTACCACCCCAGGGGGACA
ttvgt1-27  . . .    (1350) TGAAATGAAGTACATAGAACTGTGGGGAAGAGTGCCCCCACAAGGAGACT
AY823990            (1394) CAGAGCTGCCCAAAAAAAAGAATTCTCCACAGGAACAG---ATAACCCA
ttvg1-7    . . .    (1400) CGGAATTACCCGTTCAAACAGAATTCCAAAAACCCTCGGGATATAACCCA
ttvGT1-17  . . .    (1400) CAGAATTGCCGGCCCAAAAAGAATTCCAGAAACCAGACGGGTATAACCCA
ttvGT1-21  . . .    (1400) CGGAATTACCCCTTCAAACAGAATTCCAAAAACCCTCGGGATATAACCCA
ttvgt1-27  . . .    (1400) CAGAACTACCCAAGAAAAGTGAATTCACAACAGCTACAG---ACAATAAA
AY823990            (1441) AACTACAATGTTCAGGACAATGAGGAGAAAAACATATACCCCATTATAAT
ttvg1-7    . . .    (1450) AAATACTACGTAAACCCGGGGGAGGAAAAACCAATCTACCCAGTAATAAT
ttvGT1-17  . . .    (1450) AAATACTATGTGCAGGCAGGAGAGGAAAAACCTATATATCCAATAATAAT
ttvGT1-21  . . .    (1450) AAATACTACGTAAACCCGGGGGAGGAAAAACCAATCTACCCAGTAATAAT
ttvgt1-27  . . .    (1447) AACTACAATGTGAATGACGGTGAGGAAAAACCTATATACCCCATAATTAT
AY823990            (1491) ATACGTAGACCAAAAGATCAAAAACCAAGAAAAAAGTACTGCGTATGTT
ttvg1-7    . . .    (1500) ATACGTAGACATGAAAGACCAAAAACCAAGAAAAAAGTACTGCGTCTGCT
ttvGT1-17  . . .    (1500) TTACGTAGACAAAAAGATCAGAAAGCAAGAAAGAAATACTGTGTCTGTT
ttvGT1-21  . . .    (1500) ATACGTAGACATGAAAGACCAAAAACCAAGAAAAAAGTACTGCGTCTGCT
ttvgt1-27  . . .    (1497) ATACGTAGACCAAAAAGACCAAAAACCAAGGAAAAAGTACTGTGTATGTT
AY823990            (1541) ATAATAAGACCCTCAACAGATGGAGACTAGGACAGGCAAGTACTCTAAAG
ttvg1-7    . . .    (1550) ACAACAAGACGCTTAACAGGTGGCGCAGCGCTCAAGCAAGCACATTAAAA
ttvGT1-17  . . .    (1550) ACAATAAGACACTAAACAGATGGAGAGCAGCACAAGCAAGTACCCTAAAA
ttvGT1-21  . . .    (1550) ACAACAAGACGCTTAACAGGTGGCGCAGCGCTCAGGCAAGCACATTAAAA
```

```
ttvgt1-27 . . .    (1547) ACAACAAAACTCTGAACAGGTGGAGATTAGGACAAGCGAGTACTCTAAAA

AY823990           (1591) ATAGGAAACCTGAAAGGACTAGTACTAAGACAGCTGATGAATCAAGAAAT ttvg1-7 . . .      (1600) ATTGGTGACTTGCAGGGGCTAGTATTGAGACAGCTAATGAACCAAGAAAT ttvGT1-17 . . .    (1600) ATAGGAGACCTGCAAGGACTAGTACTAAGACAATTAATGAACCAGGAAAT ttvGT1-21 . . .    (1600) ATTGGTGACTTGCAGGGGCTAGTATTGAGACAGCTAATGAACCAAGAAAT ttvgt1-27 . . .    (1597) ATAGGAAACCTGAAAGGACTAGTGCTAAGACAGTTGATGAACCAAGAGAT

AY823990           (1641) GACGTATATATGGAAAGAAGGAGAATACAGTGCCCCCTTTGTACAAAGGT ttvg1-7 . . .      (1650) GACATACACATGGAAAGAAGGAGAATTTACCAATGTATTCCTGCAGAGGT ttvGT1-17 . . .    (1650) GACATATATTTGGAAAGAGGGAGAGTTCACAAACGTATTCCTGCAAAGGT ttvGT1-21 . . .    (1650) GACATACACATGGAAAGAAGGAGAATTTACAAATGTATTCCTGCAAAGGT ttvgt1-27 . . .    (1647) GACTTACATATGGAAGGAAGGAGAGTACAGCTCACCATTTGTACAAAGGT

AY823990           (1691) GGAAAGGCAGCAGATTCGCTGTGATAGACGCAAGAAAGGCAGACCAAGAA ttvg1-7 . . .      (1700) GGAGAGGTTTCAGATTAGCAGTAATAGACGCAAGAAAGGCAGACACAGAA ttvGT1-17 . . .    (1700) GGAAAGGCTTCAGACTAGCAGTCATAGACGCCAGAAAGGGAGACACAGAA ttvGT1-21 . . .    (1700) GGAGAGGTTTCAGATTAGCAGTAATAGACGCTAGAAAGGCAGACACAGAA ttvgt1-27 . . .    (1697) GGAAAGGAAGCAGATTTGTTGTGATAGACGCAAGAAAGGCTGACCAGGAA

AY823990           (1741) AACCCGAAAGTATCAACATGGCCAATTGAGGGAACGTGGAACACACAGGA ttvg1-7 . . .      (1750) AACCCGACAGTCCAAACTTGGAAGGTGGACGGACAGTGGAACACACAAGG ttvGT1-17 . . .    (1750) AATCCAACAGTACAAACATGGAAAGTAGACGGAAACTGGAACACTAGTGG ttvGT1-21 . . .    (1750) AACCCGACAGTCCAAACTTGGAAGGTGGACGGACAGTGGAACACACAAGG ttvgt1-27 . . .    (1747) AATCCCAAAGTATCTACATGGCCAATAGAGGGAGTGTGGAACACACAGGG

AY823990           (1791) CACAGTACTGAAGGATGTATTCGGTATTAACTTGCAAAATCAACAATTTA ttvg1-7 . . .      (1800) GACAGTGCTTAAAGAGGTTTTCAATATAAACCTGAATAATGAACAGATGA ttvGT1-17 . . .    (1800) AACAGTACTACAAGAAGTGTTCGGCATAAAACCTCACCCAACAACAAATGA ttvGT1-21 . . .    (1800) GACAGTTCTTAAAGAGGTTTTCAATATAAACCTGAATAATGAACAGATGA ttvgt1-27 . . .    (1797) TACAGTACTTAAGGATGTATTCCAGATTGACTTAAACAGTACTAATTTCA

AY823990           (1841) GGGCGGCGGACTTTGGTAAACTCACACTACCAAAATCACCGCATGACTTA ttvg1-7 . . .      (1850) GACAGGCAGACTTTGGAAAACTAAACTTACCAAAATCCCCGCACGACATT ttvGT1-17 . . .    (1850) GGGCATCGGACTTTGCTAAGCTAACACTACCAAAATCGCCACATGACATT ttvGT1-21 . . .    (1850) GACAGGCAGACTTTGGAAAACTAAACTTACCAAAATCCCCGCACGACATT ttvgt1-27 . . .    (1847) GAGCGGCAGACTTTGGAAAACTAACACTACCAAAATCACCGCACGACTTA

AY823990           (1891) GACTTCGGTCACCACAGCAGATTTGGGCCATTTTGTGTGAAAAATGAACC ttvg1-7 . . .      (1900) GACTTTGGACACCACAGTAGATTTGGACCTTTCTGTGTAAAAAACGAACC ttvGT1-17 . . .    (1900) GACTTTGGACACCACAGTAGATTTGGGCCATTTTGTGTCAAAAACGAACC ttvGT1-21 . . .    (1900) GACTTTGGACACCACAGTAGATTTGGACCTTTCTGTGTAAAAAACGAACC ttvgt1-27 . . .    (1897) GACTTCGGACATCACAGTAGATTCGGACCATTCTGTGTGAAAAATGAACC

AY823990           (1941) ACTGGAGTTTCAGGTATACCCTCCAGAACCAACTAACTTGTGGTTTCAGT ttvg1-7 . . .      (1950) ACTGGAGTTTCAACTAACAGCCCCAGAGCCAACTAACCTGTGGTTTCAGT ttvGT1-17 . . .    (1950) GCTGGAGTTTCAACTAACCGCTCCAGAACCTATTAATCTTTGGTTTCAGT ttvGT1-21 . . .    (1950) ACTGGAGTTTCAACTAACAGCCCCAGAGCCAACTAACCTGTGGTTTCAGT
```

-continued

```
ttvgt1-27  ...  (1947) ACTGGAATTTCAGGTATACCCGCCAGAACCCACTAACCTGTGGTTTCAGT

AY823990        (1991) ACAGATTTTTCTTTCAGTTTGGAGGTGAATACCAACCCCCCACAGGAATC ttvg1-7    ...  (2000) ACAAATTTCTGTTTCAGTTTGGAGGTGAATACCAACCACCAACAGGCATC ttvGT1-17  ...  (2000) ACAAATTTCTCTTTCAGTTTGGAGGTGAATACCAACCACCAACAGGCATC ttvGT1-21  ...  (2000) ACAAATTTCTGTTTCAGTTTGGAGGTGAATACCAACCACCAACAGGCATC ttvgt1-27  ...  (1997) ACAGATTTTTCTTTCAGTTTGGAGGTGAATACCAACCCCCCACAGGAATC

AY823990        (2041) CGGGATCCATGCGTTGATACACCAGCCTATCCTGTGCCGCAGTCAGGAAG ttvg1-7    ...  (2050) CGCGATCCCTGCGCTGATAACCCAGCCTATCCTGTGCCGCAGTCAGGAAG ttvGT1-17  ...  (2050) CGCGATCCCTGCGCTGATAACCAACCCTATCCTGTGCCGCAGTCAGGAAG ttvGT1-21  ...  (2050) CGCGATCCCTGCGCTGATAACCCAGCCTATCCTGTGCCGCAGTCAGGAAG ttvgt1-27  ...  (2047) CGCGATCCATGCGTTGATACACCAGCCTATCCTGTGCCGCAGTCAGGAAG

AY823990        (2091) TATTACACACCCCAAATTCGCCGGAAAAGGAGGAATGCTCACGGAAACAG ttvg1-7    ...  (2100) TATTACACACCCCAAATTCGCCGGAAAAGGCGGCATGCTCACGGAAACAG ttvGT1-17  ...  (2100) TATTACACACCCAAAATTCGCCGGGAAAGGAGGAATGCTCACGGAAACAG ttvGT1-21  ...  (2100) TATTACACACCCCAAATTCGCCGGAAAAGGCGGCATGCTCACGGAAACAG ttvgt1-27  ...  (2097) TATTACACACCCCAAATTCGCCGGAAAAGGCGGAATGCTCACGGAAACAG

AY823990        (2141) ACCGTTGGGGTATCACTGCTGCCTCTTCCAGAGCCCTCAGTGCAGATACA ttvg1-7    ...  (2150) ACCGTTGGGGTATCACTGCTGCCTCTTCCCGAACCCTCAGTGCAGATACA ttvGT1-17  ...  (2150) ACCGTTGGGGTATCACTGCTGCCTCTTCCAGAGCCCTCAGTGCAGATACA ttvGT1-21  ...  (2150) ACCGTTGGGGTATCACTGCTGCCTCTTCCCGAGCCCTCAGTGCAGATACA ttvgt1-27  ...  (2147) ACCGTTGGGGTATCACTCCTGCCTCTACCAGAGCCCTCTGTGCAGATACA

AY823990        (2191) CCCACAGAGGCAGCGCAAAGTGCACTTCTCCGAGGGGACTCGGAAGCGAA ttvg1-7    ...  (2200) CCCACGGAAGCAACGCAAAGTGCACTTCTCCGAGGGGACTCGGAAAAGAA ttvGT1-17  ...  (2200) CCCACGGAGGCAGCGCAAAGTGCACTTCTCCGAGGGGACTCGGAAAAGAA ttvGT1-21  ...  (2200) CCCACGGAAGCAACGCAAAGTGCACTTCTCCGAGGGGACTCGGAAAAGAA ttvgt1-27  ...  (2197) CCCACAGAAGCAACGCAGAGTGCACTTCTCCGAGGGGACTCGGAAAAGAA

AY823990        (2241) AGGAGAGGAAACCGAGGAAACCGCGTCATCGTCCAGTATCACGAGTGCCG ttvg1-7    ...  (2250) AGGAGAGGAAACCGAGGAAACCTCGTCATCGTCCAGTATCACGAGTGCCG ttvGT1-17  ...  (2250) AGGAGAGGAAACCGAGGAAACCACGTCATCGTCCAGTATCACGAGTGCCG ttvGT1-21  ...  (2250) AGGAGAGGAAACCGAGGAAACCTCGTCATCGTCCAGTATCACGAGTGCCG ttvgt1-27  ...  (2247) AGGAGAGGAAACCGAGGAAACCACGTCATCGTCCAGTATCACGAGTGCCG

AY823990        (2291) AAAGCTCTACTGAGGGAGATGGATCGTCTGATGATGAAGAGACAATCAGA ttvg1-7    ...  (2300) AAAGCTCTACTGAAGGAGATGGATCGTCTGATGATGAAGAGACAATCAGA ttvGT1-17  ...  (2300) AAAGCTCTACTGAAGGAGATGGATCGTCTGATGATGAAGAGACAATCCGA ttvGT1-21  ...  (2300) AAAGCTCTACTGAAGGAGATGGATCGTCTGATGATGAAGAGACAATCAGA ttvgt1-27  ...  (2297) AAAGCTCTACTGAGGGAGATGGATCGTCTGATGATGAAGAGACAGTCAGA

AY823990        (2341) CGCAGAAGGAGGACCTGGAAGCGACTCAGACGAATGGTCAGAGAGCAGCT ttvg1-7    ...  (2350) CGCCGAAGGAGGACCTGGAAGCGACTCAGACGGATGGTCCGAGAGCAGCT ttvGT1-17  ...  (2350) CGCAGAAGGAGGACCTGGAAGCGACTCCGACGAATGGTCAGAGAGCAGCT ttvGT1-21  ...  (2350) CGCCGAAGGAGGACCTGGAAGCGACTCAGACGGATGGTCCGAGAGCAGCT ttvgt1-27  ...  (2347) CGCCGAAGGAGGACCTGGAAGCGACTCAGACGAATGGTCCGAGAGCAGCT
```

-continued

```
AY823990       (2391) TGACCGACGAATGGACCACAAGCGACAGCGACTTCATTGACACCCCCATA
ttvg1-7    ... (2400) TGACCGACGAATGGACCACAAGCGACAGCGACTTCATTGACACCCCCATT
ttvGT1-17  ... (2400) TGACCGACGAATGGACCACAAGCGACAGCGACTTCATTGACACCCCCATA
ttvGT1-21  ... (2400) TGACCGACGAATGGACCACAAGCGACAGCGACTTCATTGACACCCCCATT
ttvgt1-27  ... (2397) TGACCGACGAATGGACCACAAGCGACAGCGACTTCATTGACACCCCCATT AY823990       (2441) AGAGAAAGATGCCTCAATAAAAAACAAAAGAAACGCTAAACAGTGTCCGA
ttvg1-7    ... (2450) AAACAGAGATGCCTCAATAAAAAACAAAAGAAACGCTAAGCAGTGTCC-C
ttvGT1-17  ... (2450) AGAGAACGATGCCTGAATAAAAAACAAAAAAAACGCTACACAGTGTCCGC
ttvGT1-21  ... (2450) AGACAGAGATGCCTCAATAAAAAGCAAAAGAAACGCTAAACAGTGTCC-C
ttvgt1-27  ... (2447) AGAGACAGATGCCTCAATAAAAAGCAAAAGAAACGCTAAACTGCCTCCGC AY823990       (2491) TTACTAATGGGGGGGGGTCCGGGGGGGGCTTGCCCCCCCGCAAGCTGGGT
ttvg1-7    ... (2499) TATTATTTTGGGGGG--TCCGGGGGGGGCTTGCCCCCCCGTAAGCTGGGT
ttvGT1-17  ... (2500) TTATTTGTAGGGGGGG-TCCGGGGGGGGCTTGCCCCCCCGTAAGCTGGGT
ttvGT1-21  ... (2499) TATTACTTTGGGGGGG-TCCGGGGGGGGCTTGCCCCCCCGTAAGCTGTGT
ttvgt1-27  ... (2497) TTATTTTTTGGGGGG--TCCGGGGGGGGCTTGCCCCCCCGAAAGCTGGGT AY823990       (2541) TACCGCACTAACTCCCTGCCAAGTGAAACTCGGGGACGAGTGAGTGCGGG
ttvg1-7    ... (2547) TACCGCACTAACTCCCTGCCAAGTGAAACTCGGGGACGAGTGAGTGCGGG
ttvGT1-17  ... (2549) TGCCGCACTAACTCCCTGCCAAGTGAAACTCGGGGACGAGTGAGTGCGGG
ttvGT1-21  ... (2548) TACCGCACTAACTCCCTGCCAAGTGAAACTCGGGGACGAGTGAGTGCGGG
ttvgt1-27  ... (2545) TACCGCACTAACTCCCTGCCAAGTGAAACTCGGGGACGAGTGAGTGCGGG AY823990       (2591) ACATCCCGTGTAATGGCTACATAACTACCCGGCTTTGCTTCGACAGTGGC
ttvg1-7    ... (2597) ACATCCCGTGTAATGGCTACATAACTACCCGGCTTTGCTTCGACAGTGGC
ttvGT1-17  ... (2599) ACATCCCGTGTAATGGCTACATAACTACCCGGCTTTGCTTCGACAGTGGC
ttvGT1-21  ... (2598) ACATCCCGTGTAATGGCTACATAACTACCCGGCTTTGCTTCCACAGTGGC
ttvgt1-27  ... (2595) ACATCCCGTGTAATGGCTACATAACTACCCGGCTTTGCTTCGACAGTGGC AY823990       (2641) CGTGGCTCGACCCTCACACAACACTGCAGGTAGGGGGCGCAATTGGGATC
ttvg1-7    ... (2647) CGTGGCTCGACCCTCACACAACACTGCAGGTAGGGGGCGCAATTGTGATC
ttvGT1-17  ... (2649) CGTGGCTCGACCCTCACACAACAATGCAGGTAGGGGGCGCAATTGGGATC
ttvGT1-21  ... (2648) CGTGGCTCGACCCTCACACAACACTGCAGGTAGGGGGCGCAATTGGGATC
ttvgt1-27  ... (2645) CGTGGCTCGACCCTCACACAACACTGCAGATAGGGGGCGCAATTGGGATC AY823990       (2691) GTTAGAAAACTATGGCC--GAGCATGGGGNNNNNNNNNNNNNNNCCAACC
ttvg1-7    ... (2697) GTTAGAAAACTATGGCCCGGAGCATGG-CCCCCCAAAC------CCCCCC
ttvGT1-17  ... (2699) GTTAGAAAACTATGGCCCG-AGCATGGGCCCCCCAAAA------CCCCCC
ttvGT1-21  ... (2698) GTTAGAAAACTATGGCCCCAAGCATGG-CCCA--AAAC------CCCCCC
ttvgt1-27  ... (2695) GTTAGAAAACTATGGCC--GAGCATGGGCCCCCACAAA-----CCCCCCC AY823990       (2739) CCCCCGGTGGGGGGGCCAAGGCCCCCCCTACACCCCCCCATGGGGGGCTG
ttvg1-7    ... (2740) TTGCCCGGGGCTGTGCCCCGGACCCCC----------------------
ttvGT1-17  ... (2742) TTGCCCGGGGCTGTGCCCCGGACCCCC----------------------
ttvGT1-21  ... (2739) TT-CCCGGGGCTGTGCCCCGGACCCCC----------------------
ttvgt1-27  ... (2738) CTGCCCGGGGCTGTGCCCCGGACCCCCC---------------------
```

```
AY823990       (2789) CCGCCCCCCAAACCCCCCGCGTCGGATGGGGGGGGCTGCGCCCCCCCCAA
ttvg1-7    ... (2767) -------------------------------------------------
ttvGT1-17  ... (2769) -------------------------------------------------
ttvGT1-21  ... (2765) -------------------------------------------------
ttvgt1-27  ... (2766) -------------------------------------------------

AY823990       (2839) ACCCCCCTTGCCCGGGGCTGTGCCCCGGACCCCC
ttvg1-7    ... (2767) ----------------------------------
ttvGT1-17  ... (2769) ----------------------------------
ttvGT1-21  ... (2765) ----------------------------------
ttvgt1-27  ... (2766) ----------------------------------
```

Nucleotide Identity Among PAH TTV's and Published Sequence

|          | AY823990 | ttvg1-7 | ttvGT1-17 | ttvGT1-21 | ttvgt1-27 |
|----------|----------|---------|-----------|-----------|-----------|
| AY823990 |          | 85      | 87        | 85        | 91        |
| ttvg1-7  |          |         | 89        | 99        | 86        |
| ttvGT1-17|          |         |           | 89        | 86        |
| ttvGT1-21|          |         |           |           | 86        |
| ttvgt1-27|          |         |           |           |           |

TTVgt1-27 demonstrates the greatest homology with published sequence, AY823990, demonstrating 91% identity. TTVgt1-7, 17, and 21 demonstrate 85-87% identity. TTVgt1-7 and TTVgt1-21 share 99% nucleotide identity Orf1 Amino Acid Alignment The following provides a comparison of the published AY823990 sequence (SEQ ID NO:25) to the corresponding amino acid sequences for TTV7 (SEQ ID NO:10), TTV17 (SEQ ID NO:11), TTV21 (SEQ ID NO:12), and TTV27 (SEQ ID NO:13)

```
AY823990      (1) MAPTRRWRRRFGRRRRRYRKRRYGWRRRYYRYRPRDYRRRWLVRRRRRSV
Ttvg1-7orf1   (1) MAFARRWRRRFGRRRRRYRKRRYGWRRRYYRYRPRYYRRRWLVRRRRRSV
Ttg1-17orf1   (1) MAPARRWRRGFGRRRRRYRKRRWGWRRRYWRYRPRYRRRRWVVRRRRRSV
Ttg1-27orf1   (1) MAPTRRWRRRFGRRRRRYRKRRYGWRRRYYRYRPRYYRRRWLVRRRRRSV
ttg1-21orf1   (1) MAFARRWRRRFGRRRRRYRKRRYGWRRRYYRYRPRYYRRRWLVRRRRRSV AY823990     (51) YRRGGRRARPYRL--FNPKVMRRVVIRGWWPILQCLKGQEALRYRPLQWD
Ttvg1-7orf1  (51) YRRGGRRARPYRISAFNPKVMRRVVIRGWWPILQCLKGQESLRYRPLQWD
Ttg1-17orf1  (51) YRRGGRRARPYRISAFNPKIMRRVVIRGWWPILQCLRGQESLRYRPLQWD
Ttg1-27orf1  (51) YRRGGRRARPYRVSAFNPKVMRRVVIRGWWPILQCLKGQESLRYRPLQWD
ttg1-21orf1  (51) YRRGGRRARPYRISAFNPKVMRRVVIRGWWPILQCLKGQESLRYRPLQWD AY823990     (99) TERQWRVRSDFEDQYGYLVQYGGGWGSGDVTLEGLYQEHLLWRNSWSKGN
Ttvg1-7orf1 (101) VEKSWRINTTLEDNYGYLVQYGGGWGSGEVTLEGLYQEHLLWRNSWSKGN
Ttg1-17orf1 (101) VEKSWRIKTDLEDNYGYLVQYGGGWGSGEVTLEGLYQEHLLWRNSWSKGN
Ttg1-27orf1 (101) TERQWRVRQDFEDQYGYLVQYGGGWGSGDVTLEGLYQEHLLWRNSWSKGN
ttg1-21orf1 (101) VEKSWRINTTLEDNYGYLVQYGGGWGSGEVTLEGLYQEHLLWRNSWSKGN AY823990    (149) DGMDLVRYFGCVVYLYPLKDQDYWFWWDTDFKELYAENIKEYSQPSVMMM
Ttvg1-7orf1 (151) DGMDLVRYFGCIVYLYPLKDQDYWFWWDTDFKELYAESIKEYSQPSVMMM
Ttg1-17orf1 (151) DGMDLVRYFGCIVYLYPLKDQDYWFWWDTDFKELYAESIKEYSQPSVMMM
Ttg1-27orf1 (151) DGMDLVRYFGCVVYLYPLKDQDYWFWWDTDFKELYAENIKEYSQPSVMMM
ttg1-21orf1 (151) DGMDLVRYFGCIVYLYPLKDQDYWFWWDTDFKELYAESIKEYSQPSVMMM AY823990    (199) AKRTRIVIARERAPHRRKVRKIFIPPPSRDTTQWQFQTDFCNRKLFTWAA
Ttvg1-7orf1 (201) AKRTKIVIARSRAPHRRKVRRIFIPPPSRDTTQWQFQTDFCNRPLFTWAA
```

```
              -continued
Ttg1-17Orf1   (201)AKKTKIVIARSRAPHRRKVRKIFIPPPSRDTTQWQFQTEFCNKPLFTWAA Ttg1-27Orf1   (201)AKRTRIVIARDRAPHRRKVRKIFIPPPSRDTTQWQFQTDFCNRKLFTWAA ttg1-21Orf1   (201)AKRTKIVIARSRAPHRRKVRRIFIPPPSRDTTQWQFQTDFCNRPLFTWAA

AY823990      (249)GLIDMQKPFDANGAFRNAWWLEQRNDQGEMKYIELWGRVPPQGDSELPKK

Ttvg1-7Orf1   (251)GLIDLQKPFDANGAFRNAWWLEQRNEAGEMKYIELWGRVPPQGDTELPVQ

Ttg1-17Orf1   (251)GLIDLQKPFDANGAFRNAWWLEQRNEAGEMKYIELWGRVPPQGDTELPAQ tg1-27Orf1    (251)GLIDMQKPFDANGAFRNAWWLEQRTEQGEMKYIELWGRVPPQGDSELPKK ttg1-21Orf1   (251)GLIDLQKPFDANGAFRNAWWLEQRNEAGEMKYIELWGRVPPQGDTELPLQ

AY823990      (299)KEFSTGT-DNPNYNVQDNEEKNIYPIIIYVDQKDQKPRKKYCVCYNKTLN

Ttvg1-7Orf1   (301)TEFQKPSGYNPKYYVNPGEEKPIYPVIIYVDMKDQKPRKKYCVCYNKTLN

Ttg1-17Orf1   (301)KEFQKPDGYNPKYYVQAGEEKPIYPIIIYVDKKDQKARKKYCVCYNKTLN

Ttg1-27Orf1   (301)SEFTTAT-DNKNYNVNDGEEKPIYPIIIYVDQKDQKPRKKYCVCYNKTLN ttg1-21Orf1   (301)TEFQKPSGYNPKYYVNPGEEKPIYPVIIYVDMKDQKPRKKYCVCYNKTLN

AY823990      (348)RWRLGQASTLKIGNLKGLVLRQLMNQEMTYIWKEGEYSAPFVQRWKGSRF

Ttvg1-7Orf1   (351)RWRSAQASTLKIGDLQGLVLRQLMNQEMTYTWKEGEFTNVFLQRWRGFRL

Ttg1-17Orf1   (351)RWRAAQASTLKIGDLQGLVLRQLMNQEMTYIWKEGEFTNVFLQRWKGFRL

Ttg1-27Orf1   (350)RWRLGQASTLKIGNLKGLVLRQLMNQEMTYIWKEGEYSSPFVQRWKGSRF ttg1-21Orf1   (351)RWRSAQASTLKIGDLQGLVLRQLMNQEMTYTWKEGEFTNVFLQRWRGFRL

AY823990      (398)AVIDARKADQENPKVSTWPIEGTWNTQDTVLKDVFGINLQNQQFRAADFG

Ttvg1-7Orf1   (401)AVIDARKADTENPTVQTWKVDGQWNTQGTVLKEVFNINLNNEQMRQADFG

Ttg1-17Orf1   (401)AVIDARKGDTENPTVQTWKVDGNWNTSGTVLQEVFGINLTQQQMRASDFA

Ttg1-27Orf1   (400)VVIDARKADQENPKVSTWPIEGVWNTQGTVLKDVFQIDLNSTNFRAADFG ttg1-21Orf1   (401)AVIDARKADTENPTVQTWKVDGQWNTQGTVLKEVFNINLNNEQMRQADFG

AY823990      (448)KLTLPKSPHDLDFGHHSRFGPFCVKNEPLEFQVYPPEPTNLWFQYRFFFQ

Ttvg1-7Orf1   (451)KLNLPKSPHDIDFGHHSRFGPFCVKNEPLEFQLTAPEPTNLWFQYKFLFQ

Ttg1-17Orf1   (451)KLTLPKSPHDIDFGHHSRFGPFCVKNEPLEFQLTAPEPINLWFQYKFLFQ

Ttg1-27Orf1   (450)KLTLPKSPHDLDFGHHSRFGPFCVKNEPLEFQVYPPEPTNLWFQYRFFFQ ttg1-21Orf1   (451)KLNLPKSPHDIDFGHHSRFGPFCVKNEPLEFQLTAPEPTNLWFQYKFLFQ

AY823990      (498)FGGEYQPPTGIRDPCVDTPAYPVPQSGSITHPKFAGKGGMLTETDRWGIT

Ttvg1-7Orf1   (501)FGGEYQPPTGIRDPCADNPAYPVPQSGSITHPKFAGKGGMLTETDRWGIT

Ttg1-17Orf1   (501)FGGEYQPPTGIRDPCADNQPYPVPQSGSITHPKFAGKGGMLTETDRWGIT

Ttg1-27Orf1   (500)FGGEYQPPTGIRDPCVDTPAYPVPQSGSITHPKFAGKGGMLTETDRWGIT ttg1-21Orf1   (501)FGGEYQPPTGIRDPCADNPAYPVPQSGSITHPKFAGKGGMLTETDRWGIT

AY823990      (548)AASSRALSADTPTEAAQSALLRGDSEAKGEETEETASSSSITSAESSTEG

Ttvg1-7Orf1   (551)AASSRTLSADTPTEATQSALLRGDSEKKGEETEETSSSSSITSAESSTEG

Ttg1-17Orf1   (551)AASSRALSADTPTEAAQSALLRGDSEKKGEETEETTSSSSITSAESSTEG

Ttg1-27Orf1   (550)PASTRALCADTPTEATQSALLRGDSEKKGEETEETTSSSSITSAESSTEG ttg1-21Orf1   (551)AASSRALSADTPTEATQSALLRGDSEKKGEETEETSSSSSITSAESSTEG

AY823990      (598)DGSSDDEETIRRRRRTWKRLRRMVREQLDRRMDHKRQRLH-

Ttvg1-7Orf1   (601)DGSSDDEETIRRRRRTWKRLRRMVREQLDRRMDHKRQRLH-

Ttg1-17Orf1   (601)DGSSDDEETIRRRRRTWKRLRRMVREQLDRRMDHKRQRLH-
```

-continued

```
Ttg1-27Orf1 (600)DGSSDDEETVRRRRRTWKRLRRMVREQLDRRMDHKRQRLHttg1-21Orf1 (601)DGSSDDEETIRRRRRTWKRLRRMVREQLDRRMDHKRQRLH-
```

|              | AY823990ORF1 | ttvg1-7ORF1 | ttvgt1-16ORF1 | ttvgt1-27ORF1 | ttvg1-21ORF1 |
|--------------|:------------:|:-----------:|:-------------:|:-------------:|:------------:|
| Ay823990ORF1 |              | 87          | 86            | 95            | 87           |
| ttvg1-7ORF1  |              |             | 93            | 87            | 100          |
| ttvgt1-17ORF1|              |             |               | 85            | 93           |
| ttvgt1-27ORF1|              |             |               |               | 87           |
| ttvg1-21ORF1 |              |             |               |               |              |

Hydrophobicity plots of the proteins demonstrate 5 areas of hydrophilicity, which may indicate surface-exposed regions that are potentially antigenic. Two of these regions are at the amino terminus and at the carboxy terminus, and are both arginine-rich and highly conserved. A highly conserved hydrophilic region between amino acids 190 and 232 was observed and may potentially serve as antigenic site. The remaining hydrophilic regions between amino acids 295 and 316, and between amino acids 415 and 470 are also be antigenic.

Additionally, it has been determined that the putative start codons for ORF1 and coding region are as follows: ttvgt1-27 nt 517-2435; ttvg1-7 nt 517-2435; ttvgt1-17 nt 517-2436; ttvgt1-21 nt 517-2439; ttv10 nt 487-2346; and ttv13 nt 477-2363. The putative start codons for ORF 2 and coding region are as follows: ttvgt1-27 nt 428-646; ttvg1-7 nt 428-643; ttvgt1-17 nt 428-643; ttvgt1-21 nt 428-646; ttv10 nt 404-610; and ttv13 nt 394-597.

TTV ORF1 Protein Expression Utilizing Recombinant Baculovirus

A series of experiments was then undertaken to express the genotype 2 TTV ORF1 protein utilizing insect cells and recombinant baculovirus. Optimization of protein expression was conducted with three cell lines (SF9, SF21 and Hi Five), multiple media configurations (ExCell 420, SF900 III SFM, Express Five SFM), various cell densities (5e5, 1e6, 2e6 and 4e6 cells/ml), and various multiplicities of infection (0.005, 0.1, 0.5, 2.0), and the resultant cultures were monitored daily over a seven day post infection period.

The processes were monitored for cell density and viability, and infection was monitored through monitoring of cell size and virus titration. Protein expression was monitored through SDS-PAGE, Coomassie gel analysis and Western blotting. To ensure proper control, negative and positive controls were maintained throughout all experiments. Although all experiments were able to confirm expression of the target protein, optimal conditions were found when utilizing SF9 cells maintained in ExCell 420 media (Sigma, SAFC) with a cell density of $2 \times 10^6$ cells/ml and an MOI of 0.1, with the process terminated following a three day infection. The majority of the recombinant expressed protein can be located within the cell pellet although some resides in the resultant supernatant.

Confirmation of Protein Expression with Western Blotting (GST-tag)

As the Invitrogen destination vectors (pDEST10) contained a GST protein N-terminal to the TTV Orf1 reading frame, a resultant GST-ORF1 fusion protein of approximately 95 kD was generated, which was detected using a commercially available rabbit anti-GST (CALBIOCHEM) antibody. Of the 95 kD fusion protein, approximately 68 kD is considered to be ORF1 and 25 kD to be the GST protein. No commercial antibody was available for standardized detection of TTV ORF1 protein, which necessitated the use of the anti-GST antibody.

Production of Rabbit Anti-TTV ORF1 Antibody

Due to the initial lack of availability of known TTV reagents, efforts were undertaken to produce anti-TTV ORF1 antibodies. Following the optimized expression protocol for preparing the TTV ORF1 recombinant protein, the resultant material was further purified utilizing the commercially available Baculogold® GST purification kit. Purified TTV10 and TTV13 ORF1 protein was then utilized to hyperimmunize rabbits for the subsequent production of antibodies against the ORF1 recombinant protein.

In regard of protein detection, FIG. 1A sample lanes were as follows (from right to left)

| Samples: | |
|---|---|
| 1  | SeeBlue Plus 2 |
| 2  | ORF1 TTV13 d.3 1e6 cell/ml (GST purified pellet) |
| 3  | ORF1 TTV13 d.3 1e6 cell/ml (GST unbound) |
| 4  | ORF1 TTV13 d.3 2e6 cell/ml (GST purified pellet) |
| 5  | ORF1 TTV13 d.3 2e6 cell/ml (GST unbound) |
| 6  | ORF1 TTV13 d.3 4e6 cell/ml (GST purified pellet) |
| 7  | ORF1 TTV13 d.3 4e6 cell/ml (GST unbound) |
| 8  | ORF1 TTV13 d.3 4e6 cell/ml (GST purified supe) |
| 9  | ORF1 TTV13 d.3 4e6 cell/ml (GST unbound) |
| 10 | ORF1 TTV13 d.3 4e6 cell/ml untreated supe.) |
| 11 | ORF1 TTV13 d.3 4e6 cell/ml untreated cell pellet |
| 12 | SF9 Negative Control d.3 pellet 1e6 cell/ml |

Lanes 2, 4 and 6 demonstrate the purified 95 kD TTV13 ORF1 fusion protein which was later utilized for the rabbit immunization, see FIG. 1A.

Detection of Native TTV ORF1 Utilizing the Rabbit Anti-ORF1 Protein

Additional expression experiments were conducted with the native TTV ORF1 recombinant baculovirus. This recombinant baculovirus was constructed without a 6×His or GST fusion tag and hence requires a specific anti-TTV ORF1 antibody. Consequently, post expression Western blot analysis was conducted utilizing the rabbit anti-TTV ORF1 antibody to confirm expression of the native protein, and to confirm the reagent reactivity. Western blot analysis demonstrated a faint reaction at approximately 69 kD, which is approximately the predicted size of TTV ORF1 as well as reaction to an additional band at approximately 49 kD (see FIG. 1B). The 49 kD protein band is unknown. The faint banding at 69 kD is assumed to be a function of either low protein expression in the native TTV ORF1 construct or poor antibody yield from the rabbit immunization. It should be noted that no purification of the antigen or antibody was conducted in this particular analysis. Lane 5 (see the arrows in FIG. 1B) demonstrates a unique reaction to a ~69 kD and 49 kD protein in the native TTV ORF1 expression utilizing anti-TTV ORF1 rabbit polyclonal antibody.

Figure 6:
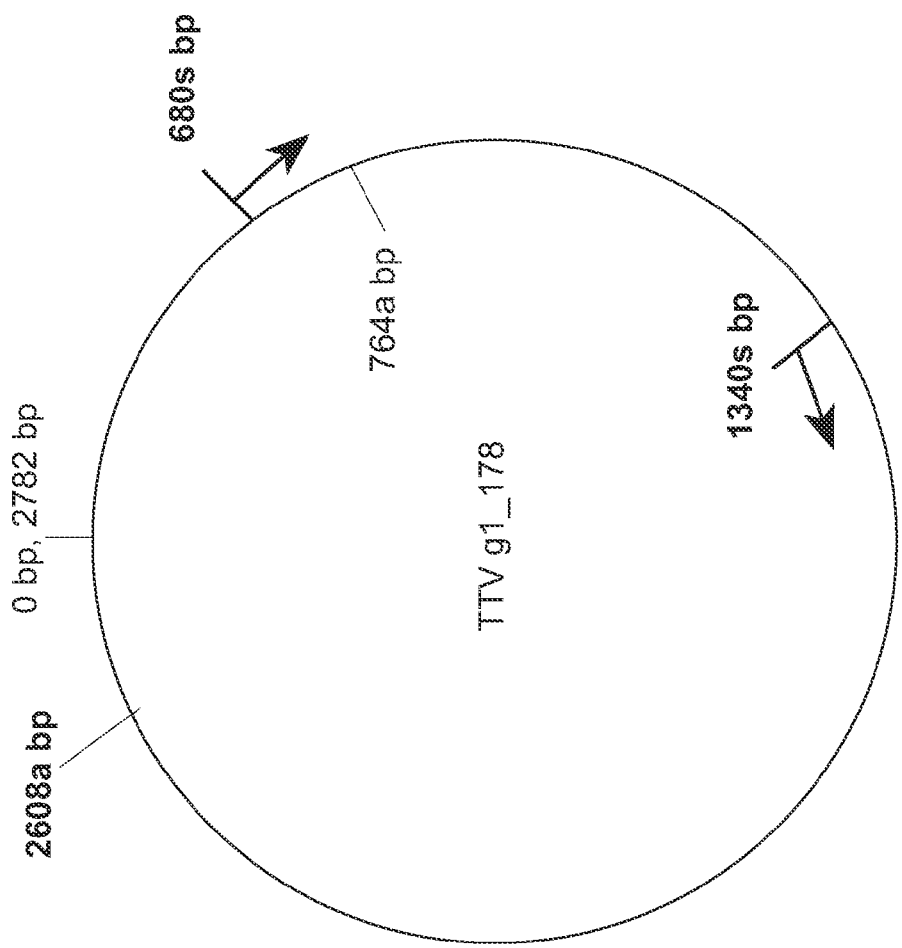
FIG. 6 provides a vector map for TTVg1-178 as assembled.

Accordingly, there was demonstrated binding of antibody to capsid protein as antigen, herein the antigen provided only TTV sequence and was not tagged. FIG. 6B sample lanes were as follows (from right to left)

| Samples: | |
|---|---|
| 1 | SeeBlue Plus 2 |
| 2 | g1TTV standard 1:50 diluted |
| 3 | g2TTV13 ORF1 Native 2DPI cell/supe 0.005 MOI |
| 4 | g2TTV13 ORF1 Native 3DPI cell/supe 0.005 MOI |
| 5 | g2TTV13 ORF1 Native 4DPI cell/supe 0.005 MOI |
| 6 | g2TTV13 ORF1 Native 2DPI cell/supe 0.1 MOI |
| 7 | g2TTV13 ORF1 Native 3DPI cell/supe 0.1 MOI |
| 8 | g2TTV13 ORF1 Native 4DPI cell/supe 0.1 MOI |
| 9 | g2TTV13 ORF1 Native 2DPI cell/supe 2.0 MOI |
| 10 | g2TTV13 ORF1 Native 3DPI cell/supe 2.0 MOI |
| 11 | g2TTV13 ORF1 Native 4DPI cell/supe 2.0 MOI |
| 12 | SF9 Neg. Control 4DPP cell/supe |

Example 2

Backpassaging

A liver was collected aseptically from a caesarean-derived, colostrum deprived (CDCD) pig. The liver tissue was tested for g1 and g2 TTV in unique qPCR assays and confirmed to be positive for only g1TTV. A 10% (wt/vol) liver homogenate was then prepared in media containing antibiotics and antimycotics. Finally, the homogenate was clarified by centrifugation, designated as g1TTVp0 and frozen at −70 C. The resulting g1TTV homogenate was tested to be free of extraneous viruses, bacteria and mycoplasma via routine testing. Following satisfactory testing, two milliliters of freshly thawed g1TTVp0 was IP inoculated into each of six 11-day old gnotobiotic piglets. At approximately 12 days post-inoculation the pigs were euthanized and the bone marrow, spleen and livers were aseptically collected. Each of the resulting livers were confirmed by qPCR to be rich in g1TTV and negative for g2TTV. Liver homogenates were then prepared from each of the resulting livers as aforementioned, labeled and aliquoted as g1TTVp1 and placed at −70 C. A further second passage (g1TTVp2) was created from g1TTVp1.

Example 3

Evaluation of the Efficacy of Three Torque Teno Virus (TTV) Vaccines in Young Pigs The present study was conducted to evaluate the efficacy of three TTV vaccine candidates administered at ~7 days of age, and again at weaning (~21 days of age) followed by a challenge at ~5 weeks of age.

This study provided a preliminary immunogenicity evaluation in pigs injected intramuscularly with formulations for TTV. As previously mentioned, TTV is a small, non-enveloped virus with a single-stranded circular DNA genome of negative polarity. The genome includes an untranslated region and at least three major overlapping open reading frames. Porcine TTV is ubiquitous and PCR-detection of the virus in serum samples collected from various geographical regions shows prevalence in pigs ranging from 33 to 100%. McKeown et al., Vet. Microbiol. (2004) 104:113-117. Krakowka et al., AJVR (2008) 69: 1623-1629, reported that g1-TTV inoculated pigs had no clinical signs but developed interstitial pneumonia, transient thymic atrophy, membranous glomerulonephropathy and modest lymphocytic to histiocytic infiltrates in the liver after inoculation. The present study provided a comparison of three different formulations of TTV vaccines, and evaluated if any of these prototype formulations can be numerically or statistically differentiated when compared to challenge control groups.

Materials and Methods

Animals: Six clinically healthy, crossbred pregnant, PRRSV and M hyo seronegative females without a history of disease caused by PRRSV or M hyo (or vaccination against the same organisms) were sourced from Lincoln Trail/Puregenic Pork, Alton, Ill., and transported to the Pfizer Animal Health Research Farm in Richland, Mich. at approximately 3 weeks pre-partum. If necessary, sows were induced to farrow within a 2 or 3 day period using injectable prostaglandin (Lutalyse®). Normal piglets from these sows were allotted to study according to the allotment design. Pigs were randomized to treatment by litter and each litter had at least one piglet assigned to each treatment.

Housing: During the vaccination phase, pigs were housed with their mother with no cross-fostering, in BL-2 isolation facilities. Pigs remained housed by litter until the time of $2^{nd}$ vaccination. Post-second vaccination pigs were moved to a further facility and housed in two rooms (one room contains NTX (non-vaccinated and non-challenge controls) animals, the second room vaccinates), and each room contains 4 or 8 pigs per pen.

Feed: Following farrowing, sows were fed a lactating sow diet as appropriate. Piglets accessed creep feed and milk replacer prior to weaning. Once weaned, piglets were feed an age-appropriate diet offering free choice. Water was available to all animals ad libitum.

Allotment/Randomization: Pigs were randomized to treatment by litter. Each litter had at least one piglet assigned to each treatment.

Study Design

| TX | Inoculum | Dose/ Route | Vacc. Days | Challenge/ Route | # of Pigs |
|---|---|---|---|---|---|
| NTX* | NA | NA | NA | NA | ~10 |
| T01 | Chromos g1TTV ORF1 recombinant protein | IM | ~7 days of age and at weaning | g1TTV pass1/IP | ~10 |
| T02 | Baculovirus g2TTV ORF1 recombinant protein | IM | (Day 21) | | ~10 |
| T03 | Inactivated challenge virus g1TTVp1. | IM | | | ~10 |
| T04 | Mock | IM | | | ~10 |

*Minimum of 1 NTX pig from each litter

Masking: Vaccine was masked using a numeric code prior to vaccination. The investigator, vaccine administrator and study personnel were masked to treatment and did not have access to the masking code unless treatment information was required for the welfare of an animal.

Investigational Veterinary Products

TABLE 1

| IVP Formulation | | |
|---|---|---|
| T01 | True Name: | Chromos g1TTV ORF1 recombinant protein |
| | Serial Number: | # 117473-185C |
| | Dosage/Formulation: | 2 mL; formulated to contain equal volumes of g1TTV ORF1 recombinant protein and sterile 5% Amphigen diluent. |
| T02 | True Name: | Baculovirus g2TTV ORF1 recombinant protein killed subunit vaccine |
| | Serial Number: | # 117473-185B |
| | Dosage/Formulation: | 2 mL; formulated to contain equal volumes of g2TTV ORF1 recombinant protein and sterile 5% Amphigen diluent. |
| T03 | True Name: | Torque Teno Vaccine, g1TTVp1 Killed Virus |
| | Serial Number: | # 117473-185D |
| | Dosage/Formulation: | 2 mL; formulated to contain equal volumes of g1TTVp1 KV antigen and sterile 5% Amphigen diluent. |
| T04 | True Name: | Mock (Placebo) |
| | Serial Number: | # 117473-185A |
| | Dosage/Formulation: | 2 mL; formulated to contain equal volumes of Phosphate buffered saline and sterile 5% Amphigen diluent. |

Challenge Material Preparation: g1TTV pass 1 was derived from liver homogenate tested positive ($7.6 \times 10^8$ to $1.6 \times 10^9$ DNA copies/2 mL) for g1TTV and negative for g2TTV by qPCR. An appropriate number of bottles were removed from the freezer and thawed shortly before challenge. An aliquot was then removed from one of the bottles, and held for retitration at a later time. Challenge stock was transported on ice to the research facility and maintained on ice during the challenge procedure. A challenge dose equals 2.0 mL of stock solution (2.0 mL intraperitoneal). The dose was delivered to each pig is therefore expected to be $7.6 \times 10^8$ to $1.6 \times 10^9$ DNA copies/2 mL. Following challenge, an aliquot of challenge stock was kept for titration to confirm challenge dose.

General Health Observations: Animals were observed daily by a qualified individual and general health observations were recorded.

Body Weights: All pigs were weighed Day 0, the day of challenge (Day 28) and at necropsy. All weights were recorded.

Vaccination: At approximately 7 days of age (Day 0), ~10 randomly allotted pigs per treatment group (Groups T01 thru T04) were vaccinated as described in Table 1. Pigs were injected in the right neck with a single dose syringe (2.0 mL intramuscular (IM) dose) of IVP, or a 2 mL IM dose of control according to allotment. A second dose of the same IVP or control was administered in the left neck at the time of weaning (~21 days of age).

Blood Sampling: Prior to Day 0, Day 14 (prior to vaccination) and Day 28 prior to challenge (as well as Day 31, 34, 37, and 40), a blood sample was collected, using 5 mL or 9 mL serum separator tubes (dependant on body weight), from all pigs for g1TTV status (qPCR-Pfizer-VMRD Laboratory Sciences). Serum samples were aliquoted by site personnel to at least three separate tubes and were stored at –80 C.

TABLE 2 g1TTV qPCR analysis to be performed on sera by time point

| | Study Day | | | | | | |
|---|---|---|---|---|---|---|---|
| | D0 | D14 | D28 | D31 | D34 | D37 | D40 |
| qPCR g1TTV | X | X | X | X | X | X | X |

Challenge: At ~5 weeks of age, piglets were inoculated with a 2.0 mL (IP or IN) dose of a TTV isolate according to allotment. Challenge material was shipped to the facility identified by a treatment code for masking purposes.

Rectal Temperatures post challenge were recorded once per day on Day 28 prior to challenge as well as Day 31, 34, 37, and 40.

Necropsies: On Day 40 all animals were euthanized and necropsied. Upon necropsy, lung lesions were scored using the following methods: 1) a numeric score (0, 1, 2, 3) and 2) the percentage of consolidation for each lobe (left cranial, left middle, left caudal, right cranial, right middle, right caudal, and accessory) was scored and recorded as percent of lobe observed with lesions. Liver, kidney, thymus and lymph nodes were also scored. A blood sample was also taken prior to euthanasia. Tissues were collected as indicated in the following table:

| Sample Type | Collection Method | Test | Location of Lab |
|---|---|---|---|
| Inguinal, mesenteric and bronchial lymph nodes | Formalin fixed sample | Formalin fixed tissue sections will be examined for histologic lesions. Sterile Tissue samples will be processed for DNA isolation and quantitative PCR analysis of g1-TTV and g2-TTV. | Borgess Hospital University: sample processing for Histology Pfizer Animal Health |
| Thymus | Formalin fixed sample | | |
| Spleen | Formalin fixed and sterile tissue samples (kidney, spleen, liver) | | |

-continued

| Sample Type | Collection Method | Test | Location of Lab |
|---|---|---|---|
| Liver | Formalin fixed and sterile tissue samples (kidney, spleen, liver) | | (qPCR) |
| Kidney | Formalin fixed and sterile tissue samples (kidney, spleen, liver) | | |
| Formalin Inflated Lung | Formalin fixed sample | | |

In regard of assessment of safety and/or efficacy, no confounding secondary disease conditions were detected. Animals were vaccinated and challenged according to protocol. In regard of outcome criteria, reduction in any or all of the following were used: decreased gross or microscopic lesions; decreased viremia by qPCR; and decreased incidence of fever, weight loss or death, two-sided tests.

Method of Analysis

Upon necropsy, lung lesions were scored using the following methods: 1) a numeric score (0=no lesions, 1=mild lesions, 2=moderate lesions, 3=severe lesions) and 2) the percentage of consolidation for each lobe (left cranial, left middle, left caudal, right cranial, right middle, right caudal, and accessory) was scored and recorded as percent of lobe observed with lesions.

The percentage of total lung with lesions was transformed and analyzed with a general linear mixed model with fixed effects, treatment, and random effect litter. Linear combinations of the parameter estimates were used in a priori contrasts after testing for a significant (P≤0.10) treatment effect. The 10% level of significance (P≤0.10) was used to assess statistical differences.

qPCR data will be transformed prior to analysis with an appropriate log transformation. The transformed titers will be analyzed using a general linear repeated measures mixed model analysis. Pairwise treatment comparisons will be made at each time point if the treatment or treatment by time point interaction effect is significant (P≤10). Treatment least squares means, 90% confidence intervals, the minimum and maximum will be calculated and back-transformed for each time point. Descriptive statistics, means, standard deviations, and ranges, will be calculated for each treatment and day of study, pre-challenge.

Study Results and Discussion

Lung Lesions

Although the overall percent lung lesions observed was low throughout all treatment groups, significant differences were found. T01 (Chromos expressed g1TTV ORF1) yielded significantly lower lung lesions when compared to both the T02 (Baculovirus expressed g2TTV ORF1) and T04 (Challenge controls). Since the challenge virus was comprised of infectious g1TTV, it may not be surprising that the genotype 2 ORF1 from Baculovirus did not provide very substantially lower lung lesions as compared to the challenge controls. It is however interesting to note that while not substantial, it did offer numerically lower lung lesion scores compared to the challenge controls, thereby indicating that some level of cross protection is possible between different TTV genotypes upon optimization of dose and adjuvant selection. It was surprising that the inactivated challenge virus (T03, g1TTVp1 Killed Virus) did not offer cross-protection against the live g1TTV challenge virus as evidenced by the lack of any statistical difference between T03 and T04. This surprising lack of cross protection further enhances the veterinary importance of novel vaccines of the invention, such as g1TTV ORF1 (T01 Chromos).

| Treatment | Number of animals | Back transform Is mean % lung with lesions | Standard error % lung with lesions | Lower 90% confidence limit of mean | Upper 90% confidence limit of mean | Range % lung with lesions |
|---|---|---|---|---|---|---|
| T01 | 11 | 0.9 | 0.74 | 0.0 | 3.2 | 0 to 7.65 |
| T02 | 11 | 1.5 | 1.07 | 0.1 | 4.3 | 0 to 12.3 |
| T03 | 11 | 2.0 | 1.23 | 0.3 | 5.1 | 0.1 to 8.6 |
| T04 | 11 | 2.0 | 1.25 | 0.3 | 5.2 | 0.18 to 7.1 |

| Contrast | 2-tailed p-value (1) | significance of 2-tailed p-value |
|---|---|---|
| T01 vs T02 | 0.2167 | N.S. |
| T01 vs T02 | 0.0472 | * |
| T01 vs. T04 | 0.0389 | * |
| T02 vs T03 | 0.5394 | N.S. |
| T02 vs T04 | 0.4955 | N.S. |
| T02 vs. T04 | 0.9454 | N.S. |

(1) P-Values > 0.10 are designated as "N.S." (Not Significant) and P-Values < or = 0.10 are designated as "*" (Signficant).

g1TTV qPCR

Analysis of the TTV qPCR viremia data (FIG. 7) reveals that T01 (Chromos g1TTV ORF1) has numerically lower TTV qPCR values as compared to T04 (Challenge controls). There exists a decrease in viremia magnitude and duration, which along with a reduction in lung lesions are indicators of efficacy. In addition, T02 (Baculovirus g2TTV ORF1) demonstrates a numerical reduction in viremia magnitude and duration compared to T04 (Challenge controls) but for a shorter period of time. This combined with the numerically lower lung lesions indicates that some genotypic cross protection (g2TTV ORF1 vaccine vs g1TTV challenge virus) was observed. One can suggest that with an optimized dose and adjuvant that broad genotypic cross protection can be realized. It is also interesting to note that (T03) g1TTVp1 KV offered no reduction in TTV qPCR viremia when compared to the challenge controls. This observation in conjunction with the lung lesion data further illustrate the novel finding that the recombinantly expressed g1TTV ORF1 (T01) provides efficacy as a vaccine.

Example 4

Codon Optimization and Recombinant Expression g1TTV ORF1 as a Full Length Protein with a 6His Tag, and Detection Thereof by an Antibody The TTVg1 nucleotide sequence was submitted to GenScript (Piscataway, N.J., USA) for codon optimization and gene synthesis for both E. coli and Saccharomyces cerevisiae. In both cases, the codon optimized gene was cloned into the GenScript pUC57 vector, as product. The GenScript OptimumGene™ codon optimization analysis involves analysis of numerous parameters including codon usage bias, GC content, CpG dinucleotide content, mRNA secondary structure, identification of possible cryptic splicing sites, presence of premature polyA sites, internal chi sites and ribosomal binding sites, negative CpG islands, RNA instability motifs (ARE), inhibition sites (INS), repeat sequences of various kinds (including direct, reverse and dyad), and also restriction sites that may interfere with cloning. Translational performance may be additionally improved via translational initiation Kozak sequences, Shine-Dalgarno sequences, and to increase efficiency of translational termination via stop codons.

Figure 2:
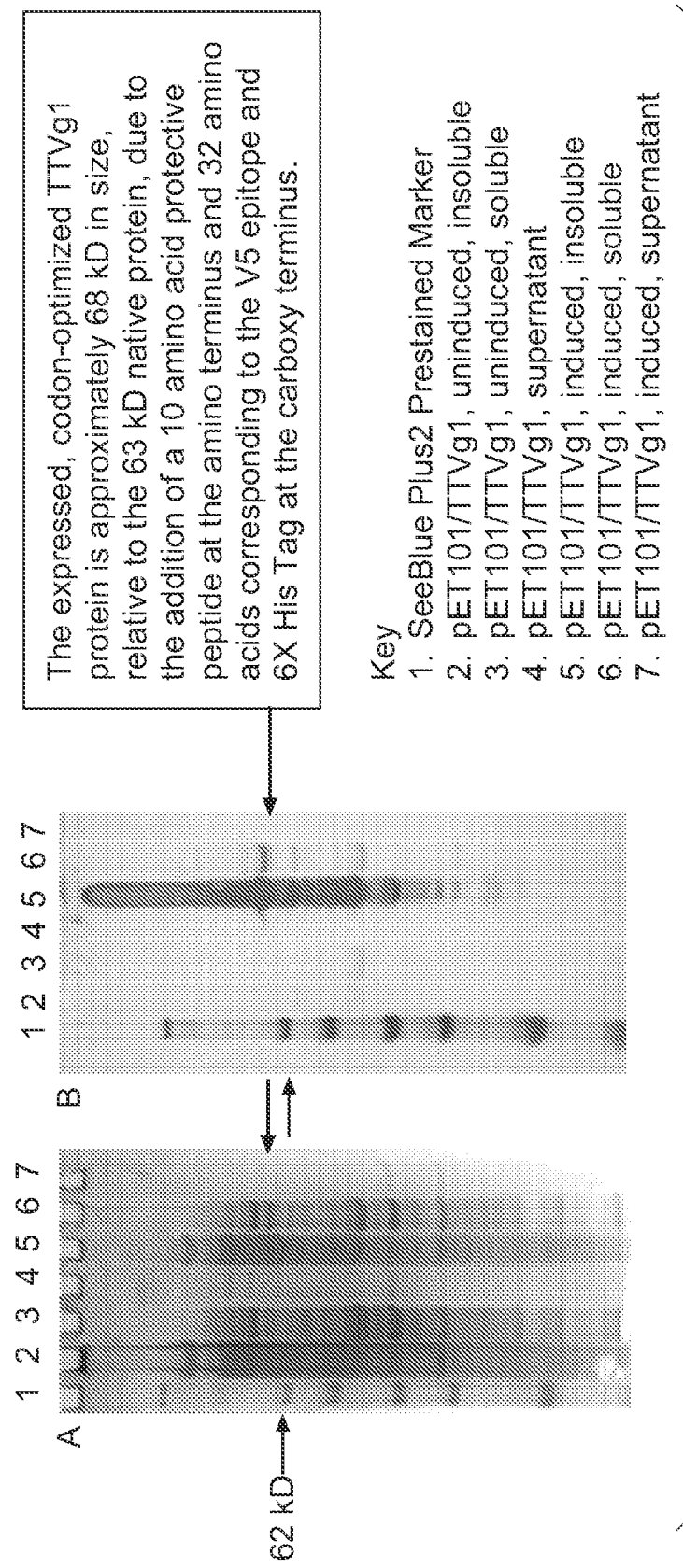
FIG. 2 evidences successful expression of codon-optimized TTVg1 ORF1 protein in *E. coli*, with a 6×His tag for affinity purification FIG. 3 provides a vector map for the Chromos construct pcTV-TTV1-7 ORF1 (plus yeast invertase) expression plasmid from which is expressed (following integration into an artificial chromosome in CHO cells) vaccinating ORF1 protein.

SEQ ID NO: NOS 18-20 provide TTV capsid gene that were codon optimized for both Escherichia coli (NOS: 18-19) and Saccharomyces cerevisiae (NO: 20). The sequences for E. coli are very similar, however, to clone the gene into the commercial pET101/D-TOPO expression vector (Invitrogen) to create 76057-4 (SEQ ID NO:19), additional CA nucleotides had to be added at the N-terminus. The pET101/D-TOPO expression vector also has a C-terminal V5 tag and 6×-His for purification, although the sequences for 76057-3 (SEQ ID NO:18) and 76057-4 are otherwise identical. The expressed codon-optimized TTVg1 protein is approximately 68 kD in size, relative to the 63 kD protein, due to the addition of a 10 amino acid protective peptide at the amino terminus, and 32 amino acids corresponding to the V5 epitope and a 6×His tag at the carboxy terminus (FIG. 2).

The sequence for 76057-5 (SEQ ID NO: 20) has been codon optimized for S. cerevisiae, and it thus differs slightly from the E. coli sequences. In addition, this sequence lacks a 10 amino acid protective peptide at the N-terminus (which was added to the E. coli sequence), and it also has flanking restriction endonuclease sites, NotI at the N-terminus and AatII at the C-terminus, for subcloning of the gene into yeast vectors.

Additionally, it should be noted that the protective peptide of ten amino acids was added to N-terminus of the TTVg1 sequence for expression in E. coli. since this has been shown to increase protein stability when fused to the amino terminus. Restriction sites have been engineered such that the peptide can be removed for evaluation of the full length protein. Expression of the codon optimized TTVg1 was evaluated in the pET101/D-TOPO vector with and without the protective peptide N-terminal fusion. The TTVg1 sequence codon optimized for S. cerevisiae was also subcloned into a pESC-Trp vector with and the potential for producing surface-expressed protein in yeast that can be used to elicit an antibody response in vivo.

Example 5

TTV Peptide Conjugation and Antibody Production (Polyclonal and Monoclonal)

Rabbit polyclonal antibodies were raised against Baculovirus expressed g2 TTV GST-ORF1 protein prepared in Example 2. Two rabbits were hyperimmunized, but only one rabbit responded. The rabbit antiserum cross-reacts to various preparations of g1 TTV whole virus that was propagated in pigs and also reacts against the immunizing antigen, Baculovirus expressed g2TTV ORF1. The rabbit antibody did not, however, respond to the E. coli expressed g2TTV ORF1 that had the 100 A.A. N-terminal arginine-rich region removed from the amino terminus as described in Example 2. This may suggest that a major antigenic epitope may be in the 100 amino acid region that was missing in the truncated g2 TTV ORF1, and that there is homology between g1 and g2 TTV in this region.

Monoclonal antibodies can be generated against full-length g1 TTV ORF1, or other g1 TTV antigens. Other potential immunizing antigens include g1 TTV whole virus, g2 TTV GST-ORF1 (Baculo), g1 TTV GST-truncated ORF1 (E. coli), and g2 TTV GST-truncated ORF1 (E. coli). A peptide library can be generated to identify linear epitopes that are antigenic. For example, 18mer peptides, with a 10AA overlap, can be utilized to cover the TTV genome. The peptides can then be utilized in Western blots or ELISA's to determine their overall reactivity to the g1TTV ORF1 or g2TTV ORF1 monoclonal and/or polyclonal antibodies so that immunogenic domains can further be identified.

Rabbit polyclonal antibodies may also be raised against three g1 TTV ORF1 peptides cross-linked to KLH, and subsequently screened using peptide-ovalbumin conjugates. The peptide-KLH conjugates can also be used to produce monoclonal antibodies. In this respect, in one embodiment, multiple g1 TTV ORF1 peptides copies may be conjugated together, including from different strains.

In particular examples, once peptides were generated (CPC Scientific), they were then conjugated to KLH or ovalbumin (by the Proteos Co). The KLH-conjugated peptides were used for immunization of rabbits, while the Ovalbumin conjugated peptides are used for screening the serum (i.e., to detect antibodies to the peptides and not the carrier protein).

Example 6

Peptide Sequences for Polyclonal Antibody Generation

The following peptide sequences were chosen from TTVg1 (numbering based on AY823990) for polyclonal antibody generation, and represent SEQ ID NOS; 22-24 respectively.

1. [L167C]TTV(167-185)-NH$_2$:
CKDQDYWFWWDTDFKELYA-NH$_2$ (19 aa, pI 4)

2. TTV(459-479):
DFGHHSRFGPFCVKNEPLEFQ (21 aa, pI 6.9)

3. [Cys612]-TTV( 612-637):
CTWKRLRRMVREQLDRRMDHKRQRLH (26 aa, pI 13)

Each of the three peptides has a single cysteine residue present in the sequence to enable selective peptide coupling to a carrier protein. In [L167C]TTV(167-185)-NH$_2$ and [Cys612]-TTV(612-637), an extra cysteine residue was added at the N-terminus, while in TTV(459-479) there is a native cys present at position 470. Additionally, [L167C]TTV (167-185)-NH$_2$ has an amidated C-terminus to yield a less acidic peptide. The peptides were selected based on sequence identity for different TTV isolates. Additionally, the C-terminal fragment [Cys612]-TTV(612-637) appears to be surface exposed. The peptides were custom made by solid phase peptide synthesis at CPC Scientific and obtained with >95% purity.

A further and highly preferred peptide is constructed by using the peptide sequence corresponding to residues 601-620 of SEQ ID NO:9 (20AA, pI 13) except that a cysteine residue is used at the N-terminus in replacement for Asn 601. This peptide is also likely surface exposed in the native protein.

Example 7

TTV g1 ORF1 Protein Expression Using the Chromos System

The Chromos ACE system is a protein expression platform that consists of three main components. The first component is a neutral, functional mammalian artificial chromosome called the Platform ACE, which resides in the genetic material of a modified Chinese Hamster Ovary (CHO) cell line. The second component is the ACE targeting vector, which is a plasmid used for loading target genes onto the Platform ACE. The third element is a site-specific, unidirectional integrase, which catalyzes the direct and specific loading of the target gene onto the Platform ACE. Additional information concerning the ACE System can be found of the website of Chromos Molecular Systems, Inc. of Canada, or by contacting the company directly at 604-415-7100 where the technology is available for license.

The Chromos ACE system has a number of significant advantages over traditional protein production platforms. The first of these is speed. The Chromos ACE system allows for the rapid, efficient and reproducible insertion of selected genes. The second advantage is expression. High level constitutive protein expression is achieved over time. A third advantage is stability. The Chromos ACE system allows selective and controlled protein expression. Briefly, restriction sites were added to both ends of the TTV7 ORF1 g1DNA using PCR. Additionally, the sequence for yeast invertase was added to the 5' end of a separate PCR preparation. The amplified sequences were then treated with restriction enzymes and sub-cloned into the plasmid pCTV927. The DNA sequence was verified by ACGT Inc. CHk2 (Chinese Hamster Ovary) cells were then transfected with the plasmids using Lipofectamine 2000 (Invitrogen), and selective pressure was added using hygromycin B. Ten single-cell clones were analyzed for TTV protein production using SDS PAGE and Western Blotting.

Figure 3:
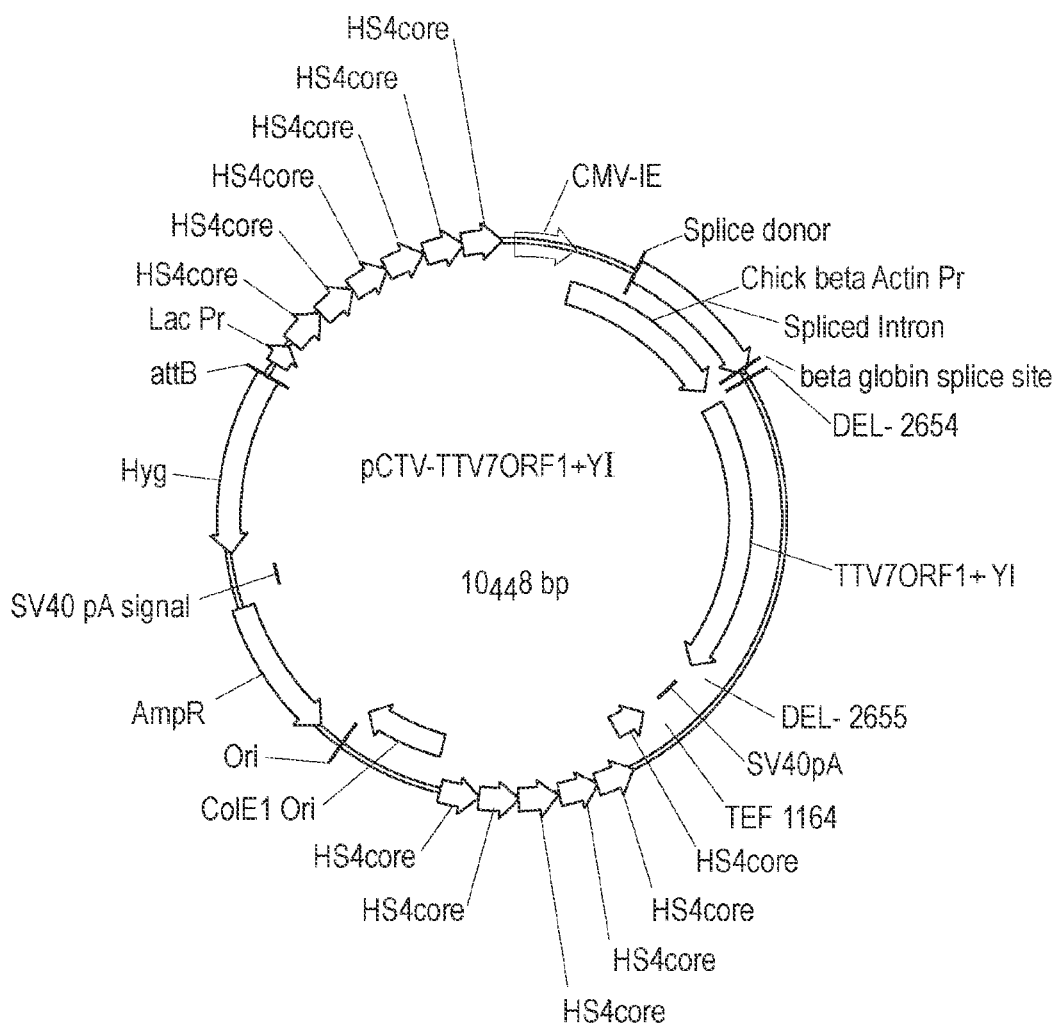

More specifically, the ACE Targeting Vector pCTV-TTV7 ORF1+YI was generated as follows (see FIG. 3). The gene TTV7 ORF1 was obtained as a PCR product. A primer was designed to contain the yeast invertase secretion signal and the restriction site EcoRV at the 5' end of the gene. A second primer was designed to contain the restriction site KpnI at the 3' end of the gene. These sequences were added to the gene TTV7 ORF1 using the polymerase chain reaction. The modified gene was then subcloned into the ACE Targeting Vector ATV$_{CHS4}$Hyg, which contained a hygromycin resistance marker suitable for downstream antibiotic selection. The new plasmid was named pCTV-TTV7 ORF1+YI.

The plasmids pCTV-TTV7 ORF1+YI and pSIO343, which coded for TTV7 ORF1/yeast invertase and the unidirectional lambda integrase, respectively, were transfected into the Chk2 cell line, which contained the Platform ACE. The transfected cells were named Chk2-TTV7 ORF1+YI. These cells were seeded in 96-well plates and monitored for the formation of single-cell clones. Media containing Hygromycin was added to each 96-well plate to select for cell clones that contained the ACE targeting vector. Once single-cell clones were identified, twelve of them were expanded into 24-well plates, and then to 6-well plates. Finally, the clones were expanded into suspension cell culture. Culture Chk2-TTV7 ORF1+YI #75 was used to generate cell-free supernatant for subsequent experimental vaccine preparation.

Figure 7:
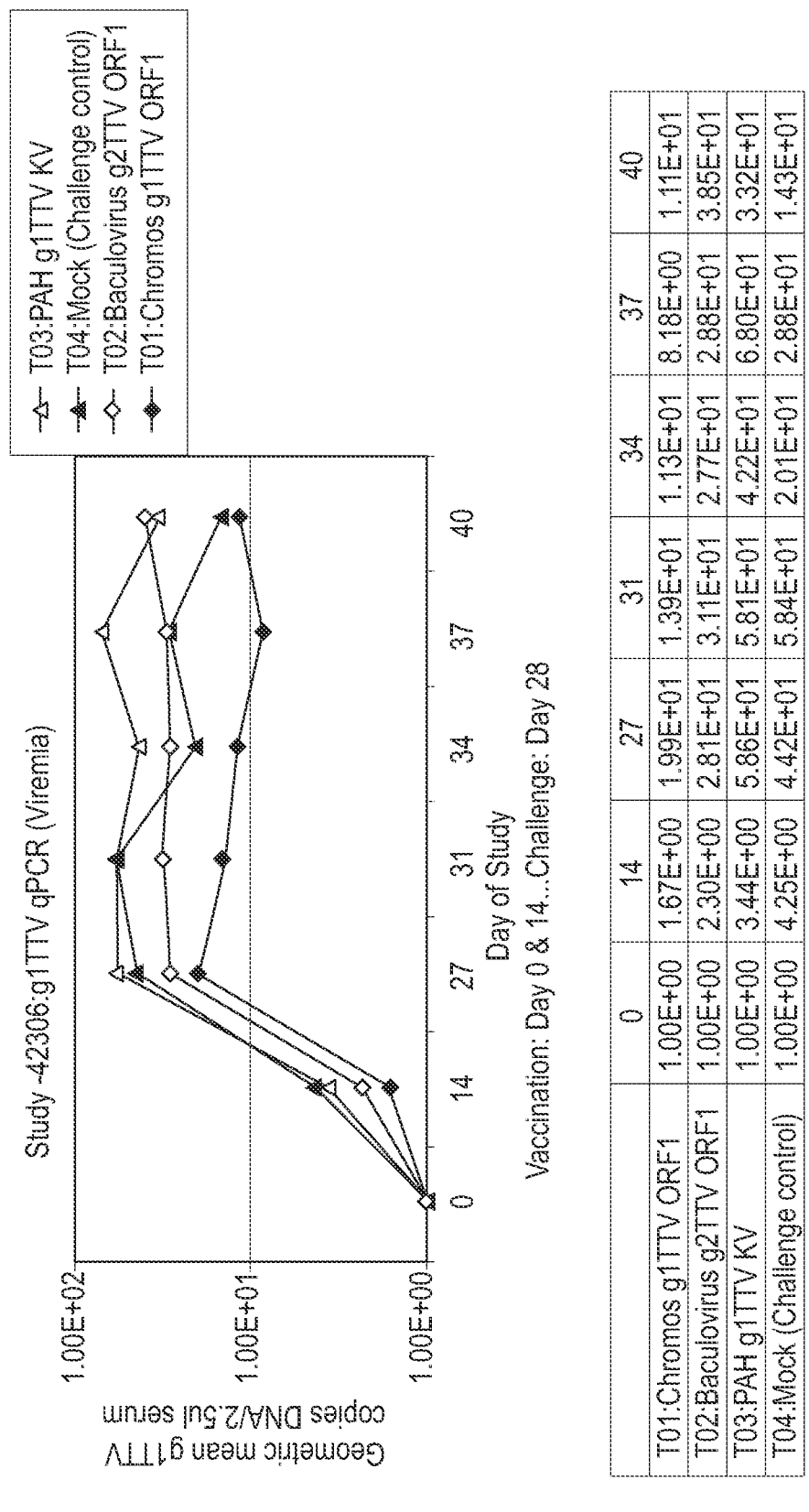
FIG. 7 demonstrates that Chromos-expressed g1TTV ORF1 significantly reduced lung lesions compared to the challenge controls and reduces the magitude and duration of g1TTV viremia, again compared to the challenge controls.
Figure 8:
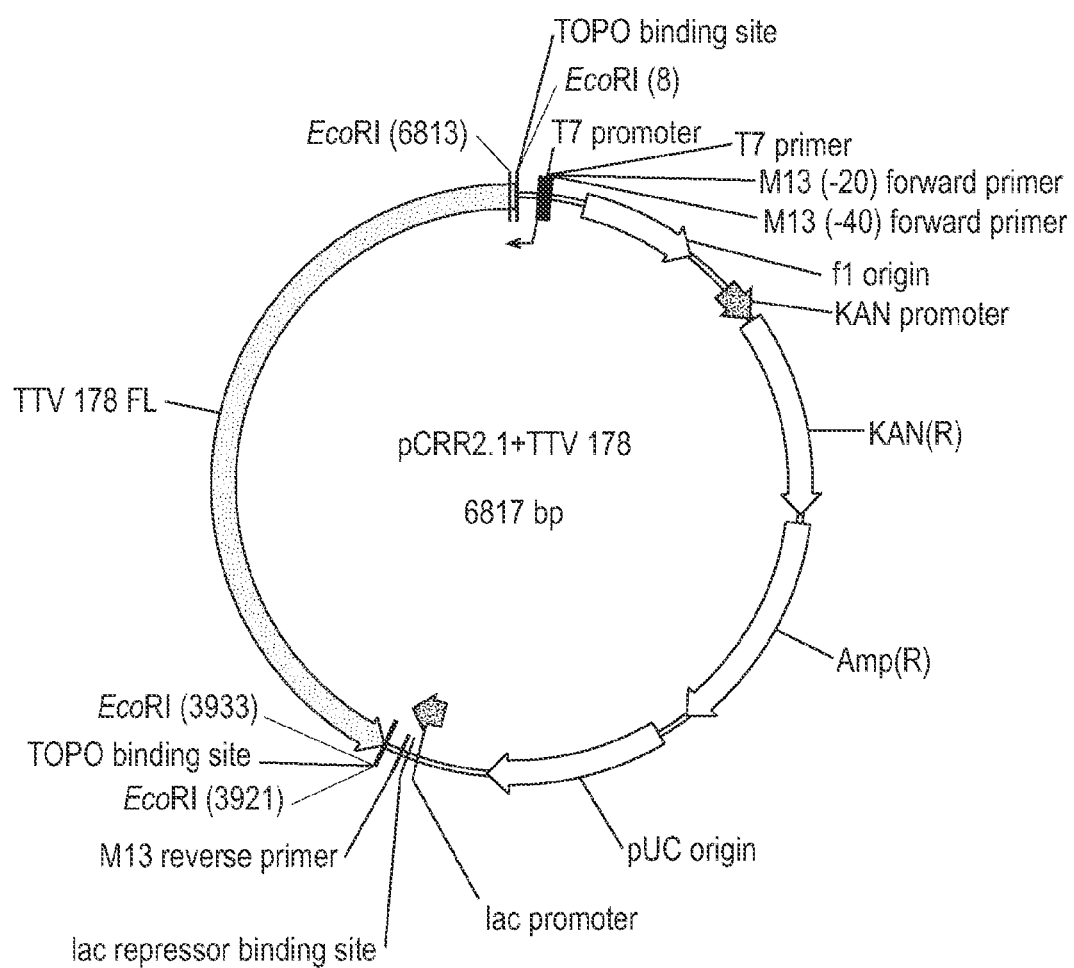
FIG. 8 provides a vector map for the pCR2.1+TTVg1-178 construct that contains a ttvg1-178 strain full length infectious clone.

FIG. 7 demonstrates that Chromos-expressed g1TTV ORF1 significantly reduced lung lesions compared to the challenge controls, and reduced the numerical magitude and duration of g1TTV viremia, again compared to the challenge controls. Vaccination was at Day 0 and 14, with challenge at Day 28. The geometric mean of detected g1TTV copies was reported exponentially, i.e. 1.00 E+00 is 1, 4.25E+00 is 4.25, and 4.42E+01 is 44.2.

Example 8

Nuclear Localization Signals

FIGS. 4 and 5 provides a 7-way amino acid alignment of ORF1 (capsid proteins) from 5 TTV gt1 viruses of the present invention and two TTV gt2 (or gt2-like) viruses of the invention. There are, of course, many gaps and mismatches because the gt1 capsids are only about 22.3 to 23.2% identical to the gt2 capsids. The five gt1 capsids are 85.6 to 99.7% identical, however, among themselves. The two gt2 capsids (TTV10 and TTV13) are similarly 66.8% identical. Full length ORF1 amino acid sequences are presented and aligned for strains ttvgt1-178, ttvgt1-7, ttvgt1-17, ttvgt1-21, ttvgt1-27, qt2 TTV10 and gt2 TTV13 (SEQ ID NO:9 through SEQ ID NO:15, consecutively). To depict the complete ORF1 amino acid sequences, the information is split into Panels A, B and C, with Panel A covering approximately residues 1-240, Panel B approximately residues 240-480, and Panel C approximately residues 480-670.

Two known types of NLS signals (Pat7 and Pat4, see U.S. Pat. No. 7,544,362, for example) were identified by inspection. In FIG. 5, the The NLS signals are underlined. Note the all seven capsids contain multiple NLS of both pat7 and pat4 type. Some are conserved between genotypes, some within a genotype, and some are not conserved. Most are near the N-terminus, where they tend to form overlapping poly-NLS regions. Numerous of these arginine—rich motifs are substantially immunogenic in mammals, and peptides containing them are useful in the generation of anti-TTV antibodies.

Example 9

Clone Fragments for Infectious Clone Construction

The following provides a basis for the construction from overlapping clones of TTV genotype 1 strain ttvgt1-178 (see SEQ ID NO:7) for which the amino acid sequence is shown as SEQ ID NO:9.

In summary, two TTV fragments (1900 bp and 2200 bp), which together span the entire TTV circular genome, were separately cloned into separate pCR 2.1 TA (Invitrogen) cloning vectors. The clone fragments were as follows: Clone 1: 680s to 2608a=~1900 bp, and Clone 2: 1340s to 764a=~2200 bp.

In order to accomplish this, PCR primers were designed using the consensus sequence that was generated from strains of the present invention (ttvgt1-27, -7, -17 and -21), and also from published sequences (AY823990(g1) and AB076001-(Sd-TTV31)). Primer pairs that correspond to the sequence at 680s and 2608a or 1340s and 764a were used to amplify PCR products from DNA that was extracted from liver homogenate samples of pigs infected with TTV challenge strain. These PCR fragments were cloned into Invitrogen's pCR2.1-TOPO TA vector using directions that were supplied with the kit. Clones were subsequently used to generate DNA sequences across the entire 2880 base genome and the sequence was found to be 86% homologous to published sequences GQ120664.1 and AY823990.1.

The fully correct sequences will now be combined for construction of a full length infectious clone.

Example 10

Infectious Clone for g1TTV

Cloning of g1TTV dsDNA Fragments.

g1TTV is a single-stranded DNA (ssDNA) virus. Fragments of g1TTV are converted to double-stranded DNA (dsDNA) using polymerase chain reaction (PCR). The dsDNA fragments of g1TTV are then cloned into pUC-based plasmid cloning vectors and transformed into *E. coli*. The fragments of g1TTV are less than 1 full-length dsDNA equivalent of the g1TTV genome.

Amplification of g1TTV dsDNA Concatemers.

Concatemers of full-length g1TTV dsDNA genome equivalents are generated using φ29 polymerase amplification kits (e.g., illustra TempliPhi). Full-length g1TTV dsDNA fragments are generated by digestion of the concatemers at appropriate restriction endonucleases (RE) sites. These full-length g1TTV dsDNA fragments can be cloned into plasmid vectors. Alternatively, the concatemers or the uncloned fragments (resulting from RE digestion) can be used without immediate cloning in subsequent molecular biology constructions (see below).

Tandem Duplications of the g1TTV Genome.

Plasmid constructs encoding tandem duplications of the g1TTV genome are next generated. The tandem duplications in the constructs are approximately greater than 1.2 copies of full-length dsDNA equivalents of the g1TTV genome. The tandem duplications in plasmids are generated using (1) subcloning employing appropriate RE sites, (2) PCR assembly of tandem duplications, or (3) other molecular biology methods. The templates for the generation of the tandem duplications are the g1TTV dsDNA fragments and/or the full-length g1TTV dsDNA clones (yielded by φ29 polymerase amplification).

In Vivo Recombination and Generation of g1TTV Virus.

The tandem duplication plasmid constructs are not identical to the g1TTV virus. The tandem duplication constructs are dsDNA while the virus is ssDNA, the constructs encode >1.2 full-length dsDNA equivalents of the g1TTV genome while the virus has only one full-length equivalent, the construct contains interrupting plasmid sequences while the virus has only viral sequences. To generate the bona fide g1TTV virus, the tandem duplication plasmid constructs are introduced into pigs (by inoculation, injection, electroporation, or other methods of introduction) or introduced into tissue culture cells (by transfection, electroporation, or other methods of introduction) where the plasmid construct recombines at homologous sequences to regenerate a unit-length dsDNA equivalent of the g1TTV genome. The dsDNA equivalent of the g1TTV genome is a presumed replicative intermediate of the g1TTV viral life cycle. The presence of this presumed dsDNA replicative intermediate will lead to the production of the bona fide ssDNA g1TTV.

Enabling In Vivo Generation of g1TTV Virus by Co-Transfection of g1TTV ORF-Expressing Constructs.

It is expected that a circular dsDNA g1TTV genome would be capable of yielding virus production. In the unexpected event that the dsDNA form of g1TTV is not replication-competent, the immediate expression of a g1TTV ORF may be required for the initiation of g1TTV replication from the dsDNA replicative intermediate. Plasmid constructs directing in vivo transcription of g1TTV ORFs can be made, such as the fusion of transcriptional promoters (e.g., CMV) to g1TTV ORFs. Alternatively, plasmid constructs directing the in vitro generation of g1TTV ORF transcripts can be made, such as the fusion of transcriptional promoters (e.g., T7) to g1TTV ORFs followed by use of in vitro transcription kits. Either g1TTV ORF-expressing plasmids or g1TTV ORF-expressing RNA transcripts can be co-injected into pigs or co-transfected into cells along with the tandem duplication plasmid constructs to yield g1TTV virus.

Detection of g1TTV Virus Production.

To date, whole g1TTV virus cannot be propagated in tissue culture cells. The generation of g1TTV virus is detected by immune reagents (e.g., α-g1TTV antibody) or by molecular methods (e.g., qPCR).

Example 11

Provision of TTV1-178 Clone in pCR2.1 Vector

Total DNA was isolated (DNEasy Blood and Tissue Kit, Qiagen, Valencia, Calif.) from a frozen liver homogenate sample (200 microliters) derived from a prior TTV challenge study. The DNA was then PCR-amplified using forward and reverse primers selected to overlap at the unique EcoRI site of the swine TTV 1-178 genome. The forward primer: for TTVg1-178 was selected as positions 1399 to 1428 (ACGG . . . CCAA) from SEQ ID NO:7, and the reverse primer: was selected to correspond to base positions 1443 (5')-to 1416 (3') ATAT . . . TTGT (opposite strand) from SEQ ID NO:7. PCR conditions were as follows: 1 cycle of denaturation at 94° C. for 1 minute; 35 cycles of 94° C., 30 seconds; 55° C., 30 sec; 72° C., 3 minutes; followed by a final 10 minute extension at 72° C. The resultant ~2.8 kb fragment was cloned into pCR2.1 vector using a TOPO TA cloning kit. (Invitrogen, Carlsbad, Calif.). Upon sequence verification, this plasmid (named pCR2.1+TTV__178) was found to contain the entire TTV 1-178 genome sequence.

pCR2.1+TTV__178 vector was then linearized with EcoRI in order to release the full length TTV genome, which was then transfected into human embryonic kidney (293), baby hamster kidney (BHK-21), swine testicular (ST) and porcine kidney (PK) cells lines using Lipofectin (Invitrogen, Carlsbad, Calif.). The transfection was allowed to proceed for a total of 5 days at which time the cells were fixed, and then used for IFA staining to determine if the TTV DNA provided expression of ORF 1 protein. IFA staining was accomplished with rabbit polyclonal sera that was raised against a peptide corresponding to a C-terminal region of the capsid protein (residues 601-620 in SEQ ID NO:9), except that the N terminal residue thereof ($Asn^{601}$) was replaced with a cysteine residue. The results indicate that the TTV-transfected DNA successfully expressed the ORF-1 protein in at least 293, BHK-21, ST and PK cells lines.

The invention claimed is:
1. An isolated plasmid that comprises a DNA polynucleotide sequence that is SEQ ID NO:5 or a polynucleotide sequence that is at least 95% identical to SEQ ID NO:5.
2. A host cell that comprises the plasmid of claim 1.

* * * * *

SEQUENCE LISTING

<160> NUMBER OF SEQ ID NOS: 29

<210> SEQ ID NO 1
<211> LENGTH: 2817
<212> TYPE: DNA
<213> ORGANISM: Torque Teno Virus, genotype 2 gt2 TTV 10

<400> SEQUENCE: 1

```
taatgacagg gttccaggaa gtgctgcaaa aattacagct aaaaccacaa ctacttacac      60
ataaccacaa atatttcag gaaactgcaa taattttcaa cacacattgc acaaaaccac     120
aagatatcaa cataaaccac aggaaactct gcaaaaaaga ggaagtaaat gctattggct     180
aaatctgaag tcttcattag catacacaac caaccaatca gaaacacttc ctcatttgaa     240
gtatataagt aaatgcgcag acgaatggct gagtttatgc cgctggtggt agacacgaac     300
agagctgagt gtctaaccgc ctgggcgggt gccggagctc cagagagcgg agtcaagggg     360
cctatcgggc gggcggtaat ccagcggaac cgggcccccc tccatggagg agagatggct     420
gacggtagcg tacgccgccc acggattatt ctgcgcctgc agtaagccca agaccacct     480 tgaaaaatgc ctttccaccg ctatcgccga cgccgaagga gacccaccag gagatggagg     540
agaaggaggt tccagcgcta ctttcgatat cggtatagac gcgctcctcg ccgccgccga     600
cgctacaagg taaggagacg gagggttaaa aaggctccgg tcattcaatg gttcccccca     660
acagtcagaa actgttttat caagggaatc tggccgttga gctacggaca ctggctccgt     720
acctgtctcc ctatgagaaa agaaaacgga ctcatattcc taggaggtgg catagactgg     780
actgtctgga gtttacagaa tctataccat gaaaaactaa actggaggaa tgtgtggact     840
tcttcaaatg atggcatgga gttcgctaga ttcagatatg caaagtttaa attttttaga     900
cacacaacca gatcctacgt agtaacatgg gaccaagaca taccatgtaa acctttacca     960
tacacaaatt tacatccatt tgtaatgctt ctaaaaaaac atcataaagt agttctaagc    1020
aaacaagact gtaatcctag aaaaatggac aaaccagtca ccttaaaaat aaagccacca    1080
ccaaaactca catcacagtg gagactaagc agagaattat caaaaatacc gctcttaaga    1140
ctaggagttt ctttaataga cttcagagaa ccatgggttg aaggttttgg aaatgcattc    1200
tttagtactt taggatatga agcagataaa agcaatttaa aaacaagcgc ttggtgccaa    1260
tgtaaatact tctggatata tgataccgga gtaaataatc atgtatatgt agtcatgtta    1320
aacaaagacg caggagataa tgcaggagac ctaataacaa atcaaaactc aatagcacac    1380
atagaacaga taggagaagg ttatccatac tggttatatt tttttggaag atctgaaaga    1440
gacttaaaag cactagcaac ttcaaacaca acataagaa acgaattcaa tactaatcct    1500
aacagcaaaa aattaaaaat agctgtaata ggatgggcta gcagtaacaa cacagcacaa    1560
gatagtacac aaggagcgaa tactccaata gaaggaacat atttaatatc acatgtgcta    1620
caaacatcag gacatacagc aggagcagca caaataaata acctattcgc ctctggatgg    1680
cctaactctc aaaactatcc acctttaaat ctagacaaaa acaactttga ctggggaaaa    1740
agagcgctat gtatactaag aaacaacatg aaaattggaa accaaaattt agatgatgag    1800
accactatgt ttgccctctt cggacccttg gtagaaaaag caaactggga aggcctagaa    1860
aaaataccag aactaaaacc agaactcaaa gactataata tcttaatgag atataacttt    1920
cgctttcagt ggggcggaca cggaacagag accttcaaaa caagtattgg agaccccagc    1980
caaataccct gtccctacgg accaggtgaa gcccccaac accttgtcag gaaccccctc    2040
aaggtacacg aggggggtcct caatgcgtgg gattatgact atgatggaat tgttagaaaa    2100
```

-continued

```
gacactctca aaagactgct tgccatcccc acagactcgg aggaggagaa agcgtacccg    2160
ctcgctggac ccaaaacaga gaaattgccc tcctcagacg aagaaggaga gagcgatatc    2220
agttcttcga gcgactcatc gacgcaagaa agcgaagaag agaagagata cagaagacga    2280
cacaagccct caaagcgaag actcctccag catgtccagc gactggtgaa gagattcagg    2340
accctataga caaatacaga aacttagcag acccctcatt aaatgtcaca ggacattttg    2400
aacacttctg ccgcttacac tataaaaaca tagcagaaat cagagctaga atgccaaaa    2460 aaaacctcaa taaactatac ttttcagact aaaagaagtt tatttcttta tttaaaacac    2520
cactagaggg cgtagcgggg ggggggaccc ccccgcaccc cccatgcgg gggcaagccc     2580 cccacacccc cctatgcggg ggctgcgccc cctgcacccc cctgctaagt cacaaaatgg    2640
cgggcgcggc tgggacacaa aatggcgcg taggggggg gggacccccc cgcaccccc      2700 ctggggggg accccctgc accccccat gcggggctc cgcccctgc accccggga         2760 ggggggaaa ccccccctca accccgcg ggggcaag ccccctgca ccccccc            2817
```

<210> SEQ ID NO 2
<211> LENGTH: 2810
<212> TYPE: DNA
<213> ORGANISM: Torque Teno Virus, genotype 2 gt2 TTV 13

<400> SEQUENCE: 2

```
taatgacagg gttcaccgga agggctgcaa aattacagct aaaaccacaa atctaacaca     60
ataaaccaca aaatattaca ggaaactgca ataaatttag aaataaatta cataaccca    120 ccaaaccaca ggaaactctg caaaaaagag gaaataaatt tcattggctg gtccataagt    180
cctcattaga atacaaaaag aaccaatcag aaacacttcc tcttttagag tatataagta    240
agtgcgcaga cgaatggctg agtttatgcc gctggtggta gacacgaaca gagctgagtg    300
tctaaccgcc tgggcgggtg ccggagctcc tgagagcgga gtcaaggggc ctatcgggca    360
ggcggtaatc cagcggaacc gggcccccc tccatggaag aaagatggct gacggtagcg    420
tactgcgccc acggattatt ctgcgactgt aaagacccga aaaacatct tgaaaaatgc     480 cttacagacg ctatcgcaga cgccgaagga gaccgacaag aagatggagg caccggaggt    540
ggagacgcta ctttcgatat cggtatcgac gcgctcctcg ccgccgccgc acaaaggtaa    600
ggagacggag gaggaaagct ccggtcatac aatggaaccc tcctagccgg aggacctgcc    660
tcatagaggg gttctggccg ttgagctacg acactggtt ccgtacctgt ctccccttta     720
gaagaaaaaa tggactaata tttacggag gaggttgtga ctggactcag tggagcttac    780 aaaacctta tcatgaaaaa ctaaactgga gaaatatatg acagctagt aacgtgggaa      840 tggaattcga attcgctaga ttttaaaag gaaaattcta cttttttaga catccttgga    900
gaaactatat agtgacttgg gatcaggaca ttccttgtaa acctttacca tatcagaact    960
tacacccatt attaatgcta ttaaaaaaac aacacaaatt agtactctca caacaaaact    1020
gtaaccctaa cagaaaacaa aaacctgtaa ctttaaaatt cagaccgcca ccaaaactaa    1080
cttcacaatg gagactaagt agagaattag caaaaatgcc actcattaga ctaggagtta    1140
gttttataga cttaacagaa ccgtggctag aaggttgggg aaatgcattt tactcagtac    1200
taggatatga agccataaaa gaacaaggac actggtcaaa ttggtcacaa attaaatatt    1260
actggatata tgatcagga gtaggaaatg ctgtatatgt agttatgcta aaacaagatg    1320
tagacgacaa cccaggaaaa atggcatcaa cattttaaaac aactcaggga caacatccca    1380
```

```
atgctataga tcacatagaa ttaataaatg aaggatggcc gtactggtta tacttttttg    1440
gtaaaagtga acaagacata aaaaggaag cacatagcgc tgaaatagca agagaatatg    1500
ctacaaatcc aaaatcaaaa aaactaaaaa taggaatagt aggatgggca tcctctaact    1560
tcacaacacc aggcagttca caaaactcag ggggaaatat agcagcaata caaggaggat    1620
acgtagcatg gcaggagga caaggaaaac taaatctagg agcaggatca ataggaaatt    1680
tgtaccaaca aggatggcca tcaaatcaaa actggccaaa tacaaacaga gacgaaacta    1740
actttgattg gggactcaga tcactttgta tactaagaga taacatgcaa ttaggaaatc    1800
aagaattaga tgatgaatgt accatgctct cactctttgg accttttgta gaaaaagcaa    1860
atccaatatt tgcaacaaca gaccctaaat actttaaacc agaactaaaa gactataatt    1920
taatcatgaa atatgccttt aaattccagt ggggaggaca tggcacagaa agatttaaaa    1980
caaccatcgg agaccccagc accatacct gccccttcga acccgggac cgcttccaca    2040 gcgggataca agacccctcc aaggtacaaa acaccgtcct caaccctgg gactatgact    2100 gtgatgggat tgttagaaaa gatactctca aaagacttct cgaactcccc acagagacag    2160
aggaggagga aaggcgtac ccactccttg acaaaaaac agagaaagag ccattatcag    2220
actccgacga agagagcgtt atctcaagca cgagcagtgg atccgatcaa gaagaagaga    2280
cgcagagacg aaagcaccac aagccaagca agcgacgact cctcaagcac ctccagcggg    2340
tggtaaagag gatgaaaaca ctgtgataga taaatacaga aacctagcag ccccctcact    2400
caatgtcaca ggacacatgg aaaaattcat gcaactacat atccaaaaca tacaagaaat    2460
aagagctaaa aatgctaaaa aatccctcaa taaactttac ttttctgatt aatagcggcc    2520
tcctgtgtcc aatctatttt tttaaacacc cttcaaaatg gcgggaggga cacaaaatgg    2580
cggagggact aagggggggg caagccccc ccccacccc catgcggggc tccgcccct    2640 gcacccccac ctaagtcaca aaatggcggc gcggctggga cacaaaatgg cggcgtcagg    2700
ggggggggga accccccccc ccctgcggg ggctccgccc cctgcacccc cgggaggggg    2760
ggaaaccccc cctcaacccc ccgcggggg caagccccc tgcacccccc    2810
```

<210> SEQ ID NO 3
<211> LENGTH: 2765
<212> TYPE: DNA
<213> ORGANISM: Torque Teno Virus, genotype 1 ttvgt1-27

<400> SEQUENCE: 3

```
tacacttccg ggttcagagg gctcaatttg gctcgcttcg ctcgcaccac gtttgctgcc      60
aggcggacct gattgaagac tgaaaaccgt taagttcaaa tttgaaaatg gcgcccaaac     120
atggcggagg ggggcggagt ttatgcaaat taatttatgc aaagtaggag gagctccatt     180
ttaatttatg caaagtagga ggagtcactt ctgattggtc gggagctcaa gtcctcattt     240
gcatagggtg taaccaatca aacttaaggc gttcccacta agtgaatat aagtaagtgc     300 ggttccgaat ggctgagttt atgccgccag cggtagacaa aactgtctag cgactgggcg     360
ggtgccggag gatccctgat ccggagtcaa ggggcctatc gggcaggagc agctgagcgg     420
agggcctatg ccggaacact gggaagaagc ctggttggaa gctaccaagg gctggcacga     480
cttagactgc cgctgcggta actggcagga ccacctatgg ctcctactcg gcgatggaga     540
cgccgctttg gccgccgccg tagacgctat agaaagagac gctatggctg gagaagacgc     600
tactaccgct acagaccgcg ttactatcgg agacgatggc tggtaaggag aaggcggcgt     660
tccgtctacc gtagaggtgg acgtagagcg cgcccctacc gggtatctgc ctttaacccc     720
```

```
aaagtaatgc ggagagtagt aataaggggg tggtggccaa tactacagtg cttaaaagga      780
caggaatcgc tgagatatag accactacag tgggacacac aaagacagtg gagagtgaga      840
caagacttcg aggatcaata cggatacctg gtgcaatacg gtggaggttg gggaagtggt      900
gatgtgacac tagagggact ataccaggaa cacttactat ggagaaattc ctggtcaaaa      960
ggaaatgatg gcatggactt agtgagatac tttggctgtg tggtatacct ctacccactt     1020
aaagatcagg actattggtt ctggtgggac actgacttta aagagctata cgcagaaaac     1080
ataaaagaat acagccaacc atcagtaatg atgatggcaa aagaactag aatagtaata     1140 gcgagagaca gagctccaca tagaagaaaa gtgagaaaaa tattcatccc accaccatca     1200
agagacacta cgcagtggca gtttcagaca gacttctgta ataggaagct atttacctgg     1260
gcggcaggac taatagacat gcaaaaaccc tttgatgcca acggagcttt tagaaatgcg     1320
tggtggctgg agcagagaac ggaacagggt gaaatgaagt acatagaact gtggggaaga     1380
gtgcccccac aaggagactc agaactaccc aagaaaagtg aattcacaac agctacagac     1440
aataaaaact acaatgtgaa tgacggtgag gaaaaaccta tatccccat aattatatac     1500 gtagaccaaa aagaccaaaa accaaggaaa agtactgtg tatgttacaa caaaactctg     1560
aacaggtgga gattaggaca agcgagtact ctaaaaatag gaaacctgaa aggactagtg     1620
ctaagacagt tgatgaacca agagatgact tacatatgga aggaaggaga gtacagctca     1680
ccatttgtac aaaggtggaa aggaagcaga tttgttgtga tagacgcaag aaaggctgac     1740
caggaaaatc ccaaagtatc tacatggcca atagagggga tgtggaacac acagggtaca     1800
gtacttaagg atgtattcca gattgactta aacagtacta atttcagagc ggcagacttt     1860
ggaaaactaa cactaccaaa atcaccgcac gacttagact tcggacatca cagtagattc     1920
ggaccattct gtgtgaaaaa tgaaccactg gaatttcagg tatacccgcc agaacccact     1980
aacctgtggt ttcagtacag attttttcttt cagtttggag gtgaatacca accccccaca     2040
ggaatccgcg atccatgcgt tgatacacca gcctatcctg tgccgcagtc aggaagtatt     2100
acacacccca aattcgccgg aaaaggcgga atgctcacgg aaacagaccg ttggggtatc     2160
actcctgcct ctaccagagc cctctgtgca gatacaccca cagaagcaac gcagagtgca     2220
cttctccgag gggactcgga aaagaaagga gaggaaaccg aggaaaccac gtcatcgtcc     2280
agtatccgta gtgccgaaag ctctactgag ggagatggat cgtctgatga tgaagagaca     2340
gtcagacgcc gaaggaggac ctggaagcga ctcagacgaa tggtccgaga gcagcttgac     2400
cgacgaatgg accacaagcg acagcgactt cattgacacc cccattagag acagatgcct     2460
caataaaaag caaagaaac gctaaactgc ctccgcttat tttttggggg gtccgggggg     2520
ggcttgcccc cccgaaagct gggttaccgc actaactccc tgccaagtga aactcgggga     2580
cgagtgagtg cgggacatcc cgtgtaatgg ctacataact acccggcttt gcttcgacag     2640
tggccgtggc tcgaccctca cacaacactg cagataggg gcgcaattgg gatcgttaga     2700
aaactatggc cgagcatggg cccccacaaa ccccccctg cccggggctg tgccccggac     2760
ccccc                                                                 2765
```

<210> SEQ ID NO 4  
<211> LENGTH: 2766  
<212> TYPE: DNA  
<213> ORGANISM: Torque Teno Virus, genotype 1 ttvgt1-7

<400> SEQUENCE: 4

```
tacacttccg ggttcaggag gctcaatttg gctcgcttcg ctcgcaccac gtttgctgcc      60
aggcggacct gtttgaagac tgaaaaccgt taaattcaaa tttgaaattg gcggtaaaca     120
tggcggaagg ggggcggagt atatgcaaat taatttatgc aaagtaggag gagctcgatt     180
ttaatttatg caaagtagga ggagtcaaat ctgattggtc gggagctcaa gtcctcattt     240
gcatagggtg taaccaatca gaattaaggc gtgcccacta aagtgaatat aagtaagtgc     300
agttccgaat ggctgagttt atgccgccag cggtagacag aactgtctag cgactgggcg     360
ggtgccggag gatcccagat ccggagtcaa ggggcctatc gggcaggagc agctgagcgg     420
agggcctatg ccggaacact gggaggaggc ctggttggaa gctaccaagg gctggcacga     480
ccttgactgc cgctgcggta attggcaaga ccacctatgg ctttgtctcg ccgatggaga     540
cgccgctttg gccgccgccg tagacgctat agaaagagac gctatggatg gaggagacgc     600
tactaccgct acagaccgcg ttactatcgg agacgatggc tggtaaggag aaggcggcgt     660
tccgtctacc gacgaggtgg acgtagagcg cgccccctacc gcatttctgc ctttaatccg     720
aaagtaatgc gtagagtagt gattagaggg tggtggccaa tactgcagtg cctaaaaggt     780
caggaatcac taagatacag accacttcag tgggacgtag agaaaagctg gagaataaac     840
acaactcttg aggacaacta tggatactta gtacagtatg gaggtggttg gggtagcgga     900
gaggtaacac tggaggggct gtatcaggag cacctactat ggagaaactc ttggtcaaaa     960
ggaaacgatg ggatggactt agtgagatac ttcggctgca tagtatatct atatccgtta    1020
aaagatcaag actactggtt ttggtgggac acagatttta aagaattata tgcagagagt    1080
atcaaagaat actcacagcc atctgtaatg atgatggcaa aaagaacaaa atagtgatc     1140
gcaagaagta gagccccaca tagaaggaag gtacgcagaa ttttcatacc gcctccaagt    1200
agagacacga cacagtggca atttcaaact gacttttgca atagaccact attcacatgg    1260
gctgcaggac tcatagacct ccaaaaacca tttgacgcaa acggtgcgtt cagaaatgcc    1320
tggtggttag aacagagaaa cgaggcagga gaaatgaaat acatagagct atggggtaga    1380
gtaccacccc aggggacac ggaattaccc gttcaaacag aattccaaaa accctcggga    1440
tataacccaa aatactacgt aaacccgggg gaggaaaaac caatctaccc agtaataata    1500
tacgtagaca tgaaagacca aaaccaagaa aaaagtact gcgtctgcta caacaagacg    1560
cttaacaggt ggcgcagcgc tcaagcaagc acattaaaaa ttggtgactt gcagggcta    1620
gtattgagac agctaatgaa ccaagaaatg acatacacat ggaaagaagg agaatttacc    1680
aatgtattcc tgcagaggtg gagaggtttc agattagcag taatagacgc aagaaaggca    1740
gacacagaaa acccgacagt ccaaacttgg aaggtggacg acagtggaa cacacaaggg    1800
acagtgctta agaggttttt caatataaac ctgaataatg aacagatgag acaggcagac    1860
tttggaaaac taaacttacc aaaatccccg cacgacattg actttggaca ccacagtaga    1920
tttggaccctt tctgtgtaaa aaacgaacca ctggagtttc aactaacagc cccgagcca    1980
actaacctgt ggtttcagta caaatttctg tttcagtttg gaggtgaata ccaaccacca    2040
acaggcatcc gcgatccctg cgctgataac ccagcctatc ctgtgccgca gtcaggaagt    2100
attacacacc ccaaattcgc cggaaaaggc ggcatgctca cggaaacaga ccgttggggt    2160
atcactgctg cctcttcccg aaccctcagt gcagatacac ccacggaagc aacgcaaagt    2220
gcacttctcc gagggactc ggaaaagaaa ggagaggaaa ccgaggaaac ctcgtcatcg    2280
tccagtatca cgagtgccga aagctctact gaaggagatg gatcgtctga tgatgaagag    2340
acaatcagac gccgaaggag gacctggaag cgactcagac ggatggtccg agagcagctt    2400
```

```
gaccgacgaa tggaccacaa gcgacagcga cttcattgac acccccatta aacagagatg    2460
cctcaataaa aaacaaaaga aacgctaagc agtgtcccta ttattttggg gggtccgggg    2520
ggggcttgcc cccccgtaag ctgggttacc gcactaactc cctgccaagt gaaactcggg    2580
gacgagtgag tgcgggacat cccgtgtaat ggctacataa ctacccggct ttgcttcgac    2640
agtggccgtg gctcgaccct cacacaacac tgcaggtagg gggcgcaatt gtgatcgtta    2700
gaaaactatg gcccggagca tggcccccca accccccct tgcccggggc tgtgcccgg     2760 accccc                                                              2766
```

<210> SEQ ID NO 5
<211> LENGTH: 2768
<212> TYPE: DNA
<213> ORGANISM: Torque Teno Virus, genotype 1 ttvgt1-17

<400> SEQUENCE: 5

```
tacacttccg ggttcaggag gctcaatttg gctcgcttcg ctcgcaccac gtttgctgcc      60
aagcggacct gattgaagac tgaaaaccgt tacattcaaa tttgaaaatg gcgcccaaac     120
atggcggatg tgggcggagt atatgcaaat taatttatgc aaagtaggag gagctcgatt     180
ttaatttatg caaagtagga ggagtcactt ctgattggtc gggaactcaa gccctcattt     240
gcatagggtg taaccaatca gaattaaggc gttccccgtg aagtgaatat aagtaagtaa     300
agttccgaat ggctgagttt atgccgccag cggtagacag aactgtctag cgactgggcg     360
ggtgccgaag gatcccagat ccggagtcaa ggggcctatc gggcaggagc agctgagcgg     420
agggcctatg ccggaacact gggaggaggc ctggttggaa gctaccaagg gctggcacga     480
cctcgactgc cgctgcggta actggcaaga ccacctatgg ctcctgctcg ccgatggaga     540
cgcggctttg gccgccgccg tagacgctat agaaagagac gctgggggctg gagaaggcgc     600 tactggagat accgaccgcg ttaccgtcgg cgcagatggc tggtaaggag aaggcggcgt     660
tccgtctacc gaagaggtgg acgtagagcg cgccctacc gtatttctgc ttttaatcca     720 aaataatgc ggagagtagt aataagggga tggtggccaa tcctacaatg tctaagagga     780
caggaatcac taagatatag accgttacag tgggactgag aaaaagctg gagaataaag     840 acagacttag aagacaacta cggctactta gtacagtacg gaggaggttg ggggagcgga     900
gaggtgactc tagaaggact gtaccaggaa cacctactat ggagaaattc atggtcaaaa     960
ggaaatgatg gaatggatct agtaagatac ttcggctgca tagtatacct gtacccactg    1020
aaagatcagg actactggtt ttggtgggac acagacttta aggaactcta tgcagaaagt    1080
attaaggagt actcacaacc atcagtaatg atgatggcaa aaaaaaacaaa aattgtaata    1140 gcgagaagta gggcaccaca cagacgaaaa gtaagaaaaa tattcatacc gccaccaagt    1200
agagacacta cacaatggca atttcaaaca gagttctgca acaaaccact attcacttgg    1260
gctgcaggac taatagacct ccaaaagcca tttgacgcaa acgagctttt tagaaatgcg    1320
tggtggttag aacagagaaa tgaggcagga gagatgaaat acatagaatt atgggggaga    1380
gtcccaccgc aaggagacac agaattgccg gcccaaaaag aattccagaa accagacggg    1440
tataacccaa atactatgt gcaggcagga gaggaaaaac ctatatatcc aataataatt    1500
tacgtagaca aaaaagatca gaaagcaaga aagaaatact gtgtctgtta caataagaca    1560
ctaaacagat ggagagcagc acaagcaagt ccctaaaaa taggagacct gcaaggacta    1620
gtactaagac aattaatgaa ccaggaaatg acatatattt ggaaagaggg agagttcaca    1680
```

```
aacgtattcc tgcaaaggtg gaaaggcttc agactagcag tcatagacgc cagaaagg

```
aaagatcagg actactggtt ttggtgggac acagatttta aggaattata tgcagagagt      1080
atcaaagaat actcacagcc atctgtaatg atgatggcaa aaagaacaaa aatagtgatc      1140
gcaagaagta gagccccaca tagaaggaag gtacgcagaa ttttcatacc gcctccaagt      1200
agagacacga cacagtggca atttcaaact gacttttgca atagaccact attcacatgg      1260
gctgcaggac tcatagacct ccaaaaacca tttgacgcaa acggtgcgtt cagaaatgcc      1320
tggtggttag aacagagaaa cgaggcagga gaaatgaaat acatagagct atggggtaga      1380
gtaccacccc aggggacac ggaattaccc cttcaaacag aattccaaaa accctcggga       1440
tataacccaa aatactacgt aaacccgggg gaggaaaaac caatctaccc agtaataata      1500
tacgtagaca tgaaagacca aaaccaaga aaaagtact gcgtctgcta caacaagacg        1560
cttaacaggt ggcgcagcgc tcaggcaagc acattaaaaa ttggtgactt gcaggggcta      1620
gtattgagac agctaatgaa ccaagaaatg acatacacat ggaaagaagg agaatttaca      1680
aatgtattcc tgcaaaggtg gagaggtttc agattagcag taatagacgc tagaaaggca      1740
gacacagaaa acccgacagt ccaaacttgg aaggtggacg acagtggaa cacacaaggg       1800 acagttctta aagaggtttt caatataaac ctgaataatg aacagatgag acaggcagac      1860
tttgaaaaac taaacttacc aaaatccccg cacgacattg actttggaca ccacagtaga      1920 tttgacctt tctgtgtaaa aaacgaacca ctggagtttc aactaacagc cccagagcca       1980
actaacctgt ggtttcagta caaatttctg tttcagtttg gaggtgaata ccaaccacca      2040
acaggcatcc gcgatccctg cgctgataac ccagcctatc ctgtgccgca gtcaggaagt      2100
attacacacc ccaaattcgc cggaaaaggc ggcatgctca cggaaacaga ccgttgggt       2160 atcactgctg cctcttcccg agccctcagt gcagatacac ccacggaagc aacgcaaagt      2220
gcacttctcc gaggggactc ggaaaagaaa ggagaggaaa ccgaggaaac ctcgtcatcg      2280
tccagtatca cgagtgccga aagctctact gaaggagatg gatcgtctga tgatgaagag      2340
acaatcagac gccgaaggag gacctggaag cgactcagac ggatggtccg agagcagctt      2400
gaccgacgaa tggaccacaa gcgacagcga cttcattgac accccatta gacagagatg       2460 cctcaataaa aagcaaaaga aacgctaaac agtgtcccta ttactttggg ggggtccggg      2520
gggggcttgc ccccccgtaa gctgtgttac cgcactaact ccctgccaag tgaaactcgg      2580
ggacgagtga gtgcgggaca tcccgtgtaa tggctacata actacccggc tttgcttcca      2640
cagtggccgt ggctcgaccc tcacacaaca ctgcaggtag ggggcgcaat gggatcgtt       2700 agaaaactat ggccccaagc atggcccaaa acccccctt cccggggctg tgccccggac        2760
cccc                                                                   2764
```

<210> SEQ ID NO 7
<211> LENGTH: 2880
<212> TYPE: DNA
<213> ORGANISM: Torque Teno Virus, genotype 1 ttvg1-178

<400> SEQUENCE: 7

```
tacacttccg ggttcaggag gctcaatttg gctcgcttcg ctcgcaccac gtttgctgcc        60
aggcggacvt gattgaagac tgaaaaccgt taaattcaaa tttgaaattg gcggtaaaca       120
tggcggaagg ggggcggagt atatgcaaat taatttatgc aaagtaggag gagctcgatt       180
ttaatttatg caaagtagga gggagtcaat ctgattggtc gggagcgcaa gtcctcattt       240
gcatagggtg taaccaatca gaattaaggc gtgcccacta aagtgaatat aagtaagtgc       300
```

```
agttccgaat ggctgagttt atgccgccag cggtagacag aactgtctag cgactgggcg    360
ggtgccggag gatcccagat ccggagtcaa ggggcctatc gggcaggagc agctgagcgg    420
agggcctatg ccggaacact gggaggaggc ctggttggaa gctaccaagg gctggcacga    480
ccttgactgc cgctgcggta attggcaaga ccacctatgg cttttgctcg ccgatggaga    540
cgccgctttg gccgccgccg tagacgctat agaaagagac gctatggatg gaggagacgc    600
tactaccgct acagaccgcg ttactatcgg agacgatggc tggtaaggag aaggcggcgt    660
tccgtctacc gacgaggtgg acgtagagcg cgcccctacc gcatttctgc ctttaatccg    720
aaagtaatgc gtagagtagt gattagaggg tggtggccaa tactgcagtg cctaaaaggt    780
caggaatcac taagatacag accacttcag tgggacgtag agaaaagctg agaataaac    840
acaactcttg aggacaacta tggatactta gtacagtatg gaggtggttg gggtagcgga    900
gaggtaacac tggaggggct gtatcaggag cacctactat ggagaaactc ttggtcaaaa    960
ggaaacgatg ggatggactt agtgagatac ttcggctgca tagtatatct atatccgtta    1020
aaagatcagg actactggtt ttggtgggac acagatttta aggaattata tgcagagagt    1080
atcaaagaat actcacagcc atctgtaatg atgatggcaa aaagaacaaa aatagtgatc    1140
gcaagaagta gagccccaca tagaaggaag gtacgcagaa ttttcatacc gcctccaagt    1200
agagacacga cacagtggca atttcaaact gacttttgca atagaccact attcacatgg    1260
gctgcaggac tcatagacct ccaaaaacca tttgacgcaa atggtgcgtt cagaaatgcc    1320
tggtggttag aacagagaaa cgaggcagga gaaatgaaat acatagagct atggggtaga    1380
gtaccacccc aggggacac ggaattaccc cttcaaacag aattccaaaa accctcggga    1440
tataacccaa aatactacgt aaacccgggg gaggaaaaac caatctaccc agtaataata    1500
tacgtagaca tgaaagacca aaaaccaaga aaaaagtact gcgtctgcta caacaagacg    1560
cttaacaggt ggcgcagcgc tcaggcaagc acattaaaaa ttggtgactt gcagggcta    1620
gtattgagac agctaatgaa ccaagaaatg acatacacat ggaaagaagg agaatttaca    1680
aatgtattcc tgcaaaggtg gagaggtttc agattagcag taatagacgc aagaaaggca    1740
gacacagaaa acccgacagt ccaaacttgg aaggtggacg gacagtggaa cacacaagga    1800
acagtactta agaggttttt caatataaac ctgaataatg aacagatgag acaggcagac    1860
tttgaaaaac taaacttacc aaaatccccg cacgacattg actttggaca ccacagtaga    1920
tttggacctt tctgtgtaaa aaacgaacca ctggagtttc aactaacagc cccagagcca    1980
actaacctgt ggtttcagta caaatttctg tttcagtttg gaggtgaata ccaaccacca    2040
acaggcatcc gcgatccctg cgctgataac ccagcctatc ctgtgccgca gtcaggaagt    2100
attacacacc ccaaattcgc cggaaaaggc ggcatgctca cggaaacaga ccgttgggt    2160
atcactgctg cctcttcccg agccctcagt gcagatacac ccacggaagc aacgcaaagt    2220
gcacttctcc gagggactc ggaaaagaaa ggagaggaaa ccgaggaaac ctcgtcatcg    2280
tccagtatca cgagtgccga aagctctact gaaggaaatg gatcgtctga tgatgaagag    2340
acaatcagac gccgaaggag gacctggaag cgactcagac ggatggtccg agagcagctt    2400
gaccgacgaa tggaccacaa cgacagcga cttcattgac ccctccatt aaagagagat    2460
gcctcaataa aaagcaaaag aaacgctaaa cagtgtccct attattttgg ggggcttcc    2520
gggagggctt gccccccccgt aagctgggtt accgcactaa ctccctgcca agtgaaactc    2580
ggggacgagt gagtgcggga catcccgtgt aatggctaca taactacccg gctttgcttc    2640
gacagtggcc gtgactcgac cctcacacaa cactgcagat aggggcgca attgggatcg    2700
```

```
ttagaaaact atggccgagc atgggggggg ctccgccccc ccaacccccc ccggtggggg    2760
ggccaaggcc ccctacacc ccccatggg gggctgccgc ccccaaaccc cccgcgtcg       2820 gatggggggg gctgcgcccc ccccaaaccc ccttgcccg ggctgtgcc ccggaccccc     2880
```

<210> SEQ ID NO 8
<211> LENGTH: 624
<212> TYPE: PRT
<213> ORGANISM: Torque Teno Virus
<220> FEATURE:
<221> NAME/KEY: PEPTIDE
<222> LOCATION: (1)..(624)
<223> OTHER INFORMATION: amino acid sequence of TTV strain AY823991 ORF1

<400> SEQUENCE: 8

```
Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Arg Arg
            20                  25                  30

Ala Pro Arg Arg Arg Thr Lys Val Arg Arg Arg Lys Lys Ala
        35                  40                  45

Pro Val Ile Gln Trp Phe Pro Ser Arg Arg Thr Cys Leu Ile Glu
50                  55                  60

Gly Phe Trp Pro Leu Ser Tyr Gly His Trp Phe Arg Thr Cys Leu Pro
65                  70                  75                  80

Phe Arg Arg Leu Asn Gly Leu Val Phe Pro Gly Gly Cys Asp Trp
                85                  90                  95

Ser Gln Trp Ser Leu Gln Asn Leu Tyr Asn Glu Lys Leu Asn Trp Arg
            100                 105                 110

Asn Ile Trp Thr Ala Ser Asn Val Gly Met Glu Phe Ala Arg Phe Leu
        115                 120                 125

Lys Gly Lys Phe Tyr Phe Phe Arg His Pro Trp Arg Asn Tyr Ile Ile
    130                 135                 140

Thr Trp Asp Gln Asp Ile Pro Cys Arg Pro Leu Pro Tyr Gln Asn Leu
145                 150                 155                 160

His Pro Leu Leu Met Leu Leu Lys Lys Gln His Lys Ile Val Leu Ser
                165                 170                 175

Gln Gln Asn Cys Asn Pro Asn Arg Lys Gln Lys Pro Val Thr Leu Lys
            180                 185                 190

Phe Lys Pro Pro Lys Leu Thr Ser Gln Trp Arg Leu Ser Arg Glu
        195                 200                 205

Leu Ala Lys Met Pro Leu Ile Arg Leu Gly Val Ser Phe Ile Asp Leu
    210                 215                 220

Thr Glu Pro Trp Val Glu Gly Trp Gly Asn Ala Phe Tyr Ser Val Leu
225                 230                 235                 240

Gly Tyr Glu Ala Val Lys Asp Gln Gly His Trp Ser Asn Trp Thr Gln
                245                 250                 255

Ile Lys Tyr Tyr Trp Ile Tyr Asp Thr Gly Val Gly Asn Ala Val Tyr
            260                 265                 270

Val Ile Leu Leu Lys Lys Asp Val Thr Asp Asn Pro Gly Asn Met Ala
        275                 280                 285

Thr Thr Phe Lys Ala Ser Gly Gly Gln His Pro Asp Ala Ile Asp His
    290                 295                 300

Ile Glu Leu Ile Asn Gln Gly Trp Pro Tyr Trp Leu Tyr Phe Tyr Gly
305                 310                 315                 320
```

```
Lys Ser Glu Gln Asp Ile Lys Lys Glu Ala His Ser Ala Glu Ile Ser
                325                 330                 335

Arg Glu Tyr Thr Arg Asp Pro Lys Ser Lys Leu Lys Ile Gly Ile
            340                 345                 350

Val Gly Trp Ala Ser Ser Asn Tyr Thr Thr Gly Ser Asp Gln Asn
        355                 360                 365

Ser Gly Ser Thr Ser Ala Ile Gln Gly Gly Tyr Val Ala Tyr Ala
    370                 375                 380

Gly Ser Gly Val Ile Gly Ala Gly Ser Ile Gly Asn Leu Tyr Gln Gln
385                 390                 395                 400

Gly Trp Pro Ser Asn Gln Asn Trp Pro Asn Thr Asn Arg Asp Lys Thr
            405                 410                 415

Asn Phe Asp Trp Gly Ile Arg Gly Leu Cys Ile Leu Arg Asp Asn Met
            420                 425                 430

His Leu Gly Ser Gln Glu Leu Asp Asp Glu Cys Thr Met Leu Thr Leu
            435                 440                 445

Phe Gly Pro Phe Val Glu Lys Ala Asn Pro Ile Phe Ala Thr Thr Asp
    450                 455                 460

Pro Lys Phe Phe Lys Pro Glu Leu Lys Asp Tyr Asn Ile Ile Met Lys
465                 470                 475                 480

Tyr Ala Phe Lys Phe Gln Trp Gly His Gly Thr Glu Arg Phe Lys
            485                 490                 495

Thr Asn Ile Gly Asp Pro Ser Thr Ile Pro Cys Pro Phe Glu Pro Gly
            500                 505                 510

Asp Arg Phe His Ser Gly Ile Gln Asp Pro Ser Lys Val Gln Asn Thr
            515                 520                 525

Val Leu Asn Pro Trp Asp Tyr Asp Cys Asp Gly Ile Val Arg Lys Asp
    530                 535                 540

Thr Leu Lys Arg Leu Leu Glu Leu Pro Thr Glu Thr Glu Glu Glu
545                 550                 555                 560

Lys Ala Tyr Pro Leu Leu Gly Gln Lys Thr Glu Lys Glu Pro Leu Ser
            565                 570                 575

Asp Ser Asp Glu Glu Ser Val Ile Ser Ser Thr Ser Gly Ser Ser
            580                 585                 590

Gln Glu Glu Glu Thr Gln Arg Arg His His Lys Pro Ser Lys Arg
            595                 600                 605

Arg Leu Leu Lys His Leu Gln Arg Val Val Lys Arg Met Lys Thr Leu
            610                 615                 620

<210> SEQ ID NO 9
<211> LENGTH: 640
<212> TYPE: PRT
<213> ORGANISM: Torque Teno Virus
<220> FEATURE:
<221> NAME/KEY: PEPTIDE
<222> LOCATION: (1)..(640)
<223> OTHER INFORMATION: amino acid sequence of TTV strain ttvgt1-178
      ORF1 (TTV genotype 1)

<400> SEQUENCE: 9

Met Ala Phe Ala Arg Arg Trp Arg Arg Phe Gly Arg Arg Arg
1               5                   10                  15

Arg Tyr Arg Lys Arg Arg Tyr Gly Trp Arg Arg Arg Tyr Tyr Arg Tyr
            20                  25                  30

Arg Pro Arg Tyr Tyr Arg Arg Trp Leu Val Arg Arg Arg Arg
            35                  40                  45
```

Ser Val Tyr Arg Arg Gly Gly Arg Arg Ala Arg Pro Tyr Arg Ile Ser
    50                  55                  60

Ala Phe Asn Pro Lys Val Met Arg Arg Val Val Ile Arg Gly Trp Trp
65                  70                  75                  80

Pro Ile Leu Gln Cys Leu Lys Gly Gln Glu Ser Leu Arg Tyr Arg Pro
                85                  90                  95

Leu Gln Trp Asp Val Glu Lys Ser Trp Arg Ile Asn Thr Thr Leu Glu
            100                 105                 110

Asp Asn Tyr Gly Tyr Leu Val Gln Tyr Gly Gly Trp Gly Ser Gly
            115                 120                 125

Glu Val Thr Leu Glu Gly Leu Tyr Gln Glu His Leu Leu Trp Arg Asn
        130                 135                 140

Ser Trp Ser Lys Gly Asn Asp Gly Met Asp Leu Val Arg Tyr Phe Gly
145                 150                 155                 160

Cys Ile Val Tyr Leu Tyr Pro Leu Lys Asp Gln Asp Tyr Trp Phe Trp
                165                 170                 175

Trp Asp Thr Asp Phe Lys Glu Leu Tyr Ala Glu Ser Ile Lys Glu Tyr
            180                 185                 190

Ser Gln Pro Ser Val Met Met Met Ala Lys Arg Thr Lys Ile Val Ile
            195                 200                 205

Ala Arg Ser Arg Ala Pro His Arg Arg Lys Val Arg Arg Ile Phe Ile
        210                 215                 220

Pro Pro Pro Ser Arg Asp Thr Thr Gln Trp Gln Phe Gln Thr Asp Phe
225                 230                 235                 240

Cys Asn Arg Pro Leu Phe Thr Trp Ala Ala Gly Leu Ile Asp Leu Gln
                245                 250                 255

Lys Pro Phe Asp Ala Asn Gly Ala Phe Arg Asn Ala Trp Trp Leu Glu
            260                 265                 270

Gln Arg Asn Glu Ala Gly Glu Met Lys Tyr Ile Glu Leu Trp Gly Arg
        275                 280                 285

Val Pro Pro Gln Gly Asp Thr Glu Leu Pro Leu Gln Thr Glu Phe Gln
290                 295                 300

Lys Pro Ser Gly Tyr Asn Pro Lys Tyr Tyr Val Asn Pro Gly Glu Glu
305                 310                 315                 320

Lys Pro Ile Tyr Pro Val Ile Ile Tyr Val Asp Met Lys Asp Gln Lys
                325                 330                 335

Pro Arg Lys Lys Tyr Cys Val Cys Tyr Asn Lys Thr Leu Asn Arg Trp
            340                 345                 350

Arg Ser Ala Gln Ala Ser Thr Leu Lys Ile Gly Asp Leu Gln Gly Leu
        355                 360                 365

Val Leu Arg Gln Leu Met Asn Gln Glu Met Thr Tyr Thr Trp Lys Glu
370                 375                 380

Gly Glu Phe Thr Asn Val Phe Leu Gln Arg Trp Arg Gly Phe Arg Leu
385                 390                 395                 400

Ala Val Ile Asp Ala Arg Lys Ala Asp Thr Glu Asn Pro Thr Val Gln
                405                 410                 415

Thr Trp Lys Val Asp Gly Gln Trp Asn Thr Gln Gly Thr Val Leu Lys
            420                 425                 430

Glu Val Phe Asn Ile Asn Leu Asn Asn Glu Gln Met Arg Gln Ala Asp
        435                 440                 445

Phe Gly Lys Leu Asn Leu Pro Lys Ser Pro His Asp Ile Asp Phe Gly
450                 455                 460

His His Ser Arg Phe Gly Pro Phe Cys Val Lys Asn Glu Pro Leu Glu

```
                465                 470                 475                 480
Phe Gln Leu Thr Ala Pro Glu Pro Thr Asn Leu Trp Phe Gln Tyr Lys
                    485                 490                 495
Phe Leu Phe Gln Phe Gly Gly Glu Tyr Gln Pro Pro Thr Gly Ile Arg
                    500                 505                 510
Asp Pro Cys Ala Asp Asn Pro Ala Tyr Pro Val Pro Gln Ser Gly Ser
                    515                 520                 525
Ile Thr His Pro Lys Phe Ala Gly Lys Gly Met Leu Thr Glu Thr
                    530                 535                 540
Asp Arg Trp Gly Ile Thr Ala Ala Ser Ser Arg Ala Leu Ser Ala Asp
545                 550                 555                 560
Thr Pro Thr Glu Ala Thr Gln Ser Ala Leu Leu Arg Gly Asp Ser Glu
                    565                 570                 575
Lys Lys Gly Glu Glu Thr Glu Glu Thr Ser Ser Ser Ser Ile Thr
                    580                 585                 590
Ser Ala Glu Ser Ser Thr Glu Gly Asn Gly Ser Ser Asp Asp Glu Glu
                    595                 600                 605
Thr Ile Arg Arg Arg Arg Arg Thr Trp Lys Arg Leu Arg Arg Met Val
                    610                 615                 620
Arg Glu Gln Leu Asp Arg Arg Met Asp His Lys Arg Gln Arg Leu His
625                 630                 635                 640

<210> SEQ ID NO 10
<211> LENGTH: 640
<212> TYPE: PRT
<213> ORGANISM: Torque Teno Virus
<220> FEATURE:
<221> NAME/KEY: PEPTIDE
<222> LOCATION: (1)..(640)
<223> OTHER INFORMATION: amino acid sequence of TTV strain ttvgt1-7 ORF1

<400> SEQUENCE: 10

Met Ala Phe Ala Arg Arg Trp Arg Arg Phe Gly Arg Arg Arg
1               5                   10                  15
Arg Tyr Arg Lys Arg Arg Tyr Gly Trp Arg Arg Tyr Tyr Arg Tyr
                20                  25                  30
Arg Pro Arg Tyr Tyr Arg Arg Trp Leu Val Arg Arg Arg Arg
                35                  40                  45
Ser Val Tyr Arg Gly Gly Arg Arg Ala Arg Pro Tyr Arg Ile Ser
                50                  55                  60
Ala Phe Asn Pro Lys Val Met Arg Arg Val Val Ile Arg Gly Trp Trp
65                  70                  75                  80
Pro Ile Leu Gln Cys Leu Lys Gly Gln Glu Ser Leu Arg Tyr Arg Pro
                    85                  90                  95
Leu Gln Trp Asp Val Glu Lys Ser Trp Arg Ile Asn Thr Thr Leu Glu
                    100                 105                 110
Asp Asn Tyr Gly Tyr Leu Val Gln Tyr Gly Gly Gly Trp Gly Ser Gly
                    115                 120                 125
Glu Val Thr Leu Glu Gly Leu Tyr Gln Glu His Leu Leu Trp Arg Asn
                    130                 135                 140
Ser Trp Ser Lys Gly Asn Asp Gly Met Asp Leu Val Arg Tyr Phe Gly
145                 150                 155                 160
Cys Ile Val Tyr Leu Tyr Pro Leu Lys Asp Gln Asp Tyr Trp Phe Trp
                    165                 170                 175
Trp Asp Thr Asp Phe Lys Glu Leu Tyr Ala Glu Ser Ile Lys Glu Tyr
                    180                 185                 190
```

```
Ser Gln Pro Ser Val Met Met Met Ala Lys Arg Thr Lys Ile Val Ile
        195                 200                 205

Ala Arg Ser Arg Ala Pro His Arg Arg Lys Val Arg Arg Ile Phe Ile
210                 215                 220

Pro Pro Pro Ser Arg Asp Thr Thr Gln Trp Gln Phe Gln Thr Asp Phe
225                 230                 235                 240

Cys Asn Arg Pro Leu Phe Thr Trp Ala Ala Gly Leu Ile Asp Leu Gln
                245                 250                 255

Lys Pro Phe Asp Ala Asn Gly Ala Phe Arg Asn Ala Trp Trp Leu Glu
                260                 265                 270

Gln Arg Asn Glu Ala Gly Glu Met Lys Tyr Ile Glu Leu Trp Gly Arg
            275                 280                 285

Val Pro Pro Gln Gly Asp Thr Glu Leu Pro Val Gln Thr Glu Phe Gln
        290                 295                 300

Lys Pro Ser Gly Tyr Asn Pro Lys Tyr Val Asn Pro Gly Glu Glu
305                 310                 315                 320

Lys Pro Ile Tyr Pro Val Ile Ile Tyr Val Asp Met Lys Asp Gln Lys
                325                 330                 335

Pro Arg Lys Lys Tyr Cys Val Cys Tyr Asn Lys Thr Leu Asn Arg Trp
                340                 345                 350

Arg Ser Ala Gln Ala Ser Thr Leu Lys Ile Gly Asp Leu Gln Gly Leu
            355                 360                 365

Val Leu Arg Gln Leu Met Asn Gln Glu Met Thr Tyr Thr Trp Lys Glu
        370                 375                 380

Gly Glu Phe Thr Asn Val Phe Leu Gln Arg Trp Arg Gly Phe Arg Leu
385                 390                 395                 400

Ala Val Ile Asp Ala Arg Lys Ala Asp Thr Glu Asn Pro Thr Val Gln
                405                 410                 415

Thr Trp Lys Val Asp Gly Gln Trp Asn Thr Gln Gly Thr Val Leu Lys
                420                 425                 430

Glu Val Phe Asn Ile Asn Leu Asn Asn Glu Gln Met Arg Gln Ala Asp
            435                 440                 445

Phe Gly Lys Leu Asn Leu Pro Lys Ser Pro His Asp Ile Asp Phe Gly
        450                 455                 460

His His Ser Arg Phe Gly Pro Phe Cys Val Lys Asn Glu Pro Leu Glu
465                 470                 475                 480

Phe Gln Leu Thr Ala Pro Glu Pro Thr Asn Leu Trp Phe Gln Tyr Lys
                485                 490                 495

Phe Leu Phe Gln Phe Gly Gly Glu Tyr Gln Pro Pro Thr Gly Ile Arg
                500                 505                 510

Asp Pro Cys Ala Asp Asn Pro Ala Tyr Pro Val Pro Gln Ser Gly Ser
            515                 520                 525

Ile Thr His Pro Lys Phe Ala Gly Lys Gly Met Leu Thr Glu Thr
        530                 535                 540

Asp Arg Trp Gly Ile Thr Ala Ala Ser Ser Arg Thr Leu Ser Ala Asp
545                 550                 555                 560

Thr Pro Thr Glu Ala Thr Gln Ser Ala Leu Leu Arg Gly Asp Ser Glu
                565                 570                 575

Lys Lys Gly Glu Glu Thr Glu Thr Ser Ser Ser Ser Ile Thr
                580                 585                 590

Ser Ala Glu Ser Ser Thr Glu Gly Asp Gly Ser Ser Asp Asp Glu Glu
            595                 600                 605
```

```
Thr Ile Arg Arg Arg Arg Thr Trp Lys Arg Leu Arg Arg Met Val
    610                 615                 620

Arg Glu Gln Leu Asp Arg Arg Met Asp His Lys Arg Gln Arg Leu His
625                 630                 635                 640

<210> SEQ ID NO 11
<211> LENGTH: 640
<212> TYPE: PRT
<213> ORGANISM: Torque Teno Virus
<220> FEATURE:
<221> NAME/KEY: PEPTIDE
<222> LOCATION: (1)..(640)
<223> OTHER INFORMATION: amino acid sequence of TTV strain ttvgt1-17
      ORF1

<400> SEQUENCE: 11

Met Ala Pro Ala Arg Arg Trp Arg Arg Gly Phe Gly Arg Arg Arg
1               5                   10                  15

Arg Tyr Arg Lys Arg Arg Trp Gly Trp Arg Arg Tyr Trp Arg Tyr
            20                  25                  30

Arg Pro Arg Tyr Arg Arg Arg Trp Leu Val Arg Arg Arg Arg
            35                  40                  45

Ser Val Tyr Arg Gly Gly Arg Arg Ala Arg Pro Tyr Arg Ile Ser
50                  55                  60

Ala Phe Asn Pro Lys Ile Met Arg Arg Val Val Ile Arg Gly Trp Trp
65                  70                  75                  80

Pro Ile Leu Gln Cys Leu Arg Gly Gln Glu Ser Leu Arg Tyr Arg Pro
                85                  90                  95

Leu Gln Trp Asp Val Glu Lys Ser Trp Arg Ile Lys Thr Asp Leu Glu
            100                 105                 110

Asp Asn Tyr Gly Tyr Leu Val Gln Tyr Gly Gly Gly Trp Gly Ser Gly
            115                 120                 125

Glu Val Thr Leu Glu Gly Leu Tyr Gln Glu His Leu Leu Trp Arg Asn
130                 135                 140

Ser Trp Ser Lys Gly Asn Asp Gly Met Asp Leu Val Arg Tyr Phe Gly
145                 150                 155                 160

Cys Ile Val Tyr Leu Tyr Pro Leu Lys Asp Gln Asp Tyr Trp Phe Trp
                165                 170                 175

Trp Asp Thr Asp Phe Lys Glu Leu Tyr Ala Glu Ser Ile Lys Glu Tyr
            180                 185                 190

Ser Gln Pro Ser Val Met Met Ala Lys Thr Lys Ile Val Ile
            195                 200                 205

Ala Arg Ser Arg Ala Pro His Arg Arg Lys Val Arg Lys Ile Phe Ile
210                 215                 220

Pro Pro Pro Ser Arg Asp Thr Thr Gln Trp Gln Phe Gln Thr Glu Phe
225                 230                 235                 240

Cys Asn Lys Pro Leu Phe Thr Trp Ala Ala Gly Leu Ile Asp Leu Gln
                245                 250                 255

Lys Pro Phe Asp Ala Asn Gly Ala Phe Arg Asn Ala Trp Trp Leu Glu
            260                 265                 270

Gln Arg Asn Glu Ala Gly Glu Met Lys Tyr Ile Glu Leu Trp Gly Arg
            275                 280                 285

Val Pro Pro Gln Gly Asp Thr Glu Leu Pro Ala Gln Lys Glu Phe Gln
290                 295                 300

Lys Pro Asp Gly Tyr Asn Pro Lys Tyr Tyr Val Gln Ala Gly Glu Glu
305                 310                 315                 320
```

```
Lys Pro Ile Tyr Pro Ile Ile Tyr Val Asp Lys Asp Gln Lys
            325                 330                 335

Ala Arg Lys Lys Tyr Cys Val Cys Tyr Asn Lys Thr Leu Asn Arg Trp
        340                 345                 350

Arg Ala Ala Gln Ala Ser Thr Leu Lys Ile Gly Asp Leu Gln Gly Leu
            355                 360                 365

Val Leu Arg Gln Leu Met Asn Gln Glu Met Thr Tyr Ile Trp Lys Glu
370                 375                 380

Gly Glu Phe Thr Asn Val Phe Leu Gln Arg Trp Lys Gly Phe Arg Leu
385                 390                 395                 400

Ala Val Ile Asp Ala Arg Lys Gly Asp Thr Glu Asn Pro Thr Val Gln
            405                 410                 415

Thr Trp Lys Val Asp Gly Asn Trp Asn Thr Ser Gly Thr Val Leu Gln
            420                 425                 430

Glu Val Phe Gly Ile Asn Leu Thr Gln Gln Met Arg Ala Ser Asp
            435                 440                 445

Phe Ala Lys Leu Thr Leu Pro Lys Ser Pro His Asp Ile Asp Phe Gly
    450                 455                 460

His His Ser Arg Phe Gly Pro Phe Cys Val Lys Asn Glu Pro Leu Glu
465                 470                 475                 480

Phe Gln Leu Thr Ala Pro Glu Pro Ile Asn Leu Trp Phe Gln Tyr Lys
                485                 490                 495

Phe Leu Phe Gln Phe Gly Gly Glu Tyr Gln Pro Pro Thr Gly Ile Arg
            500                 505                 510

Asp Pro Cys Ala Asp Asn Gln Pro Tyr Pro Val Pro Gln Ser Gly Ser
            515                 520                 525

Ile Thr His Pro Lys Phe Ala Gly Lys Gly Gly Met Leu Thr Glu Thr
    530                 535                 540

Asp Arg Trp Gly Ile Thr Ala Ala Ser Ser Arg Ala Leu Ser Ala Asp
545                 550                 555                 560

Thr Pro Thr Glu Ala Ala Gln Ser Ala Leu Leu Arg Gly Asp Ser Glu
                565                 570                 575

Lys Lys Gly Glu Glu Thr Glu Glu Thr Thr Ser Ser Ser Ser Ile Thr
            580                 585                 590

Ser Ala Glu Ser Ser Thr Glu Gly Asp Gly Ser Ser Asp Asp Glu Glu
        595                 600                 605

Thr Ile Arg Arg Arg Arg Arg Thr Trp Lys Arg Leu Arg Arg Met Val
    610                 615                 620

Arg Glu Gln Leu Asp Arg Arg Met Asp His Lys Arg Gln Arg Leu His
625                 630                 635                 640

<210> SEQ ID NO 12
<211> LENGTH: 640
<212> TYPE: PRT
<213> ORGANISM: Torque Teno Virus
<220> FEATURE:
<221> NAME/KEY: PEPTIDE
<222> LOCATION: (1)..(640)
<223> OTHER INFORMATION: amino acid sequence of TTV strain ttvgt1-21
      ORF1

<400> SEQUENCE: 12

Met Ala Phe Ala Arg Arg Trp Arg Arg Phe Gly Arg Arg Arg
1               5                   10                  15

Arg Tyr Arg Lys Arg Arg Tyr Gly Trp Arg Arg Arg Tyr Tyr Arg Tyr
            20                  25                  30
```

-continued

```
Arg Pro Arg Tyr Tyr Arg Arg Trp Leu Val Arg Arg Arg Arg
            35                  40                  45

Ser Val Tyr Arg Arg Gly Gly Arg Arg Ala Arg Pro Tyr Arg Ile Ser
 50                  55                  60

Ala Phe Asn Pro Lys Val Met Arg Arg Val Val Ile Arg Gly Trp Trp
 65                  70                  75                  80

Pro Ile Leu Gln Cys Leu Lys Gly Gln Glu Ser Leu Arg Tyr Arg Pro
                 85                  90                  95

Leu Gln Trp Asp Val Glu Lys Ser Trp Arg Ile Asn Thr Thr Leu Glu
            100                 105                 110

Asp Asn Tyr Gly Tyr Leu Val Gln Tyr Gly Gly Trp Gly Ser Gly
            115                 120                 125

Glu Val Thr Leu Glu Gly Leu Tyr Gln Glu His Leu Leu Trp Arg Asn
            130                 135                 140

Ser Trp Ser Lys Gly Asn Asp Gly Met Asp Leu Val Arg Tyr Phe Gly
145                 150                 155                 160

Cys Ile Val Tyr Leu Tyr Pro Leu Lys Asp Gln Asp Tyr Trp Phe Trp
                165                 170                 175

Trp Asp Thr Asp Phe Lys Glu Leu Tyr Ala Glu Ser Ile Lys Glu Tyr
            180                 185                 190

Ser Gln Pro Ser Val Met Met Met Ala Lys Arg Thr Lys Ile Val Ile
            195                 200                 205

Ala Arg Ser Arg Ala Pro His Arg Arg Lys Val Arg Arg Ile Phe Ile
            210                 215                 220

Pro Pro Pro Ser Arg Asp Thr Thr Gln Trp Gln Phe Gln Thr Asp Phe
225                 230                 235                 240

Cys Asn Arg Pro Leu Phe Thr Trp Ala Ala Gly Leu Ile Asp Leu Gln
                245                 250                 255

Lys Pro Phe Asp Ala Asn Gly Ala Phe Arg Asn Ala Trp Trp Leu Glu
                260                 265                 270

Gln Arg Asn Glu Ala Gly Glu Met Lys Tyr Ile Glu Leu Trp Gly Arg
            275                 280                 285

Val Pro Pro Gln Gly Asp Thr Glu Leu Pro Leu Gln Thr Glu Phe Gln
            290                 295                 300

Lys Pro Ser Gly Tyr Asn Pro Lys Tyr Tyr Val Asn Pro Gly Glu Glu
305                 310                 315                 320

Lys Pro Ile Tyr Pro Val Ile Ile Tyr Val Asp Met Lys Asp Gln Lys
                325                 330                 335

Pro Arg Lys Lys Tyr Cys Val Cys Tyr Asn Lys Thr Leu Asn Arg Trp
            340                 345                 350

Arg Ser Ala Gln Ala Ser Thr Leu Lys Ile Gly Asp Leu Gln Gly Leu
            355                 360                 365

Val Leu Arg Gln Leu Met Asn Gln Glu Met Thr Tyr Thr Trp Lys Glu
            370                 375                 380

Gly Glu Phe Thr Asn Val Phe Leu Gln Arg Trp Arg Gly Phe Arg Leu
385                 390                 395                 400

Ala Val Ile Asp Ala Arg Lys Ala Asp Thr Glu Asn Pro Thr Val Gln
                405                 410                 415

Thr Trp Lys Val Asp Gly Gln Trp Thr Gln Gly Thr Val Leu Lys
            420                 425                 430

Glu Val Phe Asn Ile Asn Leu Asn Asn Glu Gln Met Arg Gln Ala Asp
            435                 440                 445

Phe Gly Lys Leu Asn Leu Pro Lys Ser Pro His Asp Ile Asp Phe Gly
```

450                 455                 460
His His Ser Arg Phe Gly Pro Phe Cys Val Lys Asn Glu Pro Leu Glu
465                 470                 475                 480

Phe Gln Leu Thr Ala Pro Glu Pro Thr Asn Leu Trp Phe Gln Tyr Lys
                485                 490                 495

Phe Leu Phe Gln Phe Gly Gly Glu Tyr Gln Pro Pro Thr Gly Ile Arg
                500                 505                 510

Asp Pro Cys Ala Asp Asn Pro Ala Tyr Pro Val Pro Gln Ser Gly Ser
                515                 520                 525

Ile Thr His Pro Lys Phe Ala Gly Lys Gly Gly Met Leu Thr Glu Thr
                530                 535                 540

Asp Arg Trp Gly Ile Thr Ala Ala Ser Ser Arg Ala Leu Ser Ala Asp
545                 550                 555                 560

Thr Pro Thr Glu Ala Thr Gln Ser Ala Leu Leu Arg Gly Asp Ser Glu
                565                 570                 575

Lys Lys Gly Glu Glu Thr Glu Val Thr Ser Ser Ser Ser Ile Thr
                580                 585                 590

Ser Ala Glu Ser Ser Thr Glu Gly Asp Gly Ser Ser Asp Asp Glu Glu
                595                 600                 605

Thr Ile Arg Arg Arg Arg Arg Thr Trp Lys Arg Leu Arg Arg Met Val
610                 615                 620

Arg Glu Gln Leu Asp Arg Arg Met Asp His Lys Arg Gln Arg Leu His
625                 630                 635                 640

<210> SEQ ID NO 13
<211> LENGTH: 639
<212> TYPE: PRT
<213> ORGANISM: Torque Teno Virus
<220> FEATURE:
<221> NAME/KEY: PEPTIDE
<222> LOCATION: (1)..(639)
<223> OTHER INFORMATION: amino acid sequence of TTV strain ttvgt1-27
      ORF1

<400> SEQUENCE: 13

Met Ala Pro Thr Arg Arg Trp Arg Arg Phe Gly Arg Arg Arg
1               5                   10                  15

Arg Tyr Arg Lys Arg Tyr Gly Trp Arg Arg Tyr Tyr Arg Tyr
                20                  25                  30

Arg Pro Arg Tyr Tyr Arg Arg Trp Leu Val Arg Arg Arg Arg
                35                  40                  45

Ser Val Tyr Arg Gly Gly Arg Ala Arg Pro Tyr Arg Val Ser
50                  55                  60

Ala Phe Asn Pro Lys Val Met Arg Arg Val Val Ile Arg Gly Trp Trp
65                  70                  75                  80

Pro Ile Leu Gln Cys Leu Lys Gly Gln Glu Ser Leu Arg Tyr Arg Pro
                85                  90                  95

Leu Gln Trp Asp Thr Glu Arg Gly Trp Arg Val Arg Gln Asp Phe Glu
                100                 105                 110

Asp Gln Tyr Gly Tyr Leu Val Gln Tyr Gly Gly Gly Trp Ser Gly
                115                 120                 125

Asp Val Thr Leu Glu Gly Leu Tyr Gln Glu His Leu Leu Trp Arg Asn
                130                 135                 140

Ser Trp Ser Lys Gly Asn Asp Gly Met Asp Leu Val Arg Tyr Phe Gly
145                 150                 155                 160

Cys Val Val Tyr Leu Tyr Pro Leu Lys Asp Gln Asp Tyr Trp Phe Trp

-continued

```
                165                 170                 175
Trp Asp Thr Asp Phe Lys Glu Leu Tyr Ala Glu Asn Ile Lys Glu Tyr
            180                 185                 190

Ser Gln Pro Ser Val Met Met Ala Lys Arg Thr Arg Ile Val Ile
        195                 200                 205

Ala Arg Asp Arg Ala Pro His Arg Arg Lys Val Arg Lys Ile Phe Ile
    210                 215                 220

Pro Pro Pro Ser Arg Asp Thr Thr Gln Trp Gln Phe Gln Thr Asp Phe
225                 230                 235                 240

Cys Asn Arg Lys Leu Phe Thr Trp Ala Ala Gly Leu Ile Asp Met Gln
                245                 250                 255

Lys Pro Phe Asp Ala Asn Gly Ala Phe Arg Asn Ala Trp Trp Leu Glu
            260                 265                 270

Gln Arg Thr Glu Gln Gly Glu Met Lys Tyr Ile Glu Leu Trp Gly Arg
        275                 280                 285

Val Pro Pro Gln Gly Asp Ser Glu Leu Pro Lys Lys Ser Glu Phe Thr
    290                 295                 300

Thr Ala Thr Asp Asn Lys Asn Tyr Asn Val Asn Asp Gly Glu Glu Lys
305                 310                 315                 320

Pro Ile Tyr Pro Ile Ile Tyr Val Asp Gln Lys Asp Gln Lys Pro
                325                 330                 335

Arg Lys Lys Tyr Cys Val Cys Tyr Asn Lys Thr Leu Asn Arg Trp Arg
            340                 345                 350

Leu Gly Gln Ala Ser Thr Leu Lys Ile Gly Asn Leu Lys Gly Leu Val
        355                 360                 365

Leu Arg Gln Leu Met Asn Gln Glu Met Thr Tyr Ile Trp Lys Glu Gly
    370                 375                 380

Glu Tyr Ser Ser Pro Phe Val Gln Arg Trp Lys Gly Ser Arg Phe Val
385                 390                 395                 400

Val Ile Asp Ala Arg Lys Ala Asp Gln Glu Asn Pro Lys Val Ser Thr
                405                 410                 415

Trp Pro Ile Glu Gly Val Trp Asn Thr Gln Gly Thr Val Leu Lys Asp
            420                 425                 430

Val Phe Gln Ile Asp Leu Asn Ser Thr Asn Phe Arg Ala Ala Asp Phe
        435                 440                 445

Gly Lys Leu Thr Leu Pro Lys Ser Pro His Asp Leu Asp Phe Gly His
    450                 455                 460

His Ser Arg Phe Gly Pro Phe Cys Val Lys Asn Glu Pro Leu Glu Phe
465                 470                 475                 480

Gln Val Tyr Pro Pro Glu Pro Thr Asn Leu Trp Phe Gln Tyr Arg Phe
                485                 490                 495

Phe Phe Gln Phe Gly Gly Glu Tyr Gln Pro Pro Thr Gly Ile Arg Asp
            500                 505                 510

Pro Cys Val Asp Thr Pro Ala Tyr Pro Val Pro Gln Ser Gly Ser Ile
        515                 520                 525

Thr His Pro Lys Phe Ala Gly Lys Gly Gly Met Leu Thr Glu Thr Asp
    530                 535                 540

Arg Trp Gly Ile Thr Pro Ala Ser Thr Arg Ala Leu Cys Ala Asp Thr
545                 550                 555                 560

Pro Thr Glu Ala Thr Gln Ser Ala Leu Leu Arg Gly Asp Ser Glu Lys
                565                 570                 575

Lys Gly Glu Glu Thr Glu Glu Thr Thr Ser Ser Ser Ile Thr Ser
            580                 585                 590
```

Ala Glu Ser Ser Thr Glu Gly Asp Gly Ser Ser Asp Asp Glu Glu Thr
            595                 600                 605

Val Arg Arg Arg Arg Thr Trp Lys Arg Leu Arg Arg Met Val Arg
610                 615                 620

Glu Gln Leu Asp Arg Arg Met Asp His Lys Arg Gln Arg Leu His
625                 630                 635

<210> SEQ ID NO 14
<211> LENGTH: 620
<212> TYPE: PRT
<213> ORGANISM: Torque Teno Virus
<220> FEATURE:
<221> NAME/KEY: PEPTIDE
<222> LOCATION: (1)..(620)
<223> OTHER INFORMATION: amino acid sequence of TTV strain gt2 TTV10
      ORF1 (genotype 2)

<400> SEQUENCE: 14

Met Pro Phe His Arg Tyr Arg Arg Arg Arg Pro Thr Arg Arg
1               5                   10                  15

Trp Arg Arg Arg Phe Gln Arg Tyr Phe Arg Tyr Arg Arg
            20                  25                  30

Ala Pro Arg Arg Arg Tyr Lys Val Arg Arg Arg Val Lys
        35                  40                  45

Lys Ala Pro Val Ile Gln Trp Phe Pro Thr Val Arg Asn Cys Phe
50                  55                  60

Ile Lys Gly Ile Trp Pro Leu Ser Tyr Gly His Trp Leu Arg Thr Cys
65                  70                  75                  80

Leu Pro Met Arg Lys Glu Asn Gly Leu Ile Phe Leu Gly Gly Ile
                85                  90                  95

Asp Trp Thr Val Trp Ser Leu Gln Asn Leu Tyr His Glu Lys Leu Asn
                    100                 105                 110

Trp Arg Asn Val Trp Thr Ser Ser Asn Asp Gly Met Glu Phe Ala Arg
            115                 120                 125

Phe Arg Tyr Ala Lys Phe Lys Phe Phe Arg His Thr Thr Arg Ser Tyr
    130                 135                 140

Val Val Thr Trp Asp Gln Asp Ile Pro Cys Lys Pro Leu Pro Tyr Thr
145                 150                 155                 160

Asn Leu His Pro Phe Val Met Leu Leu Lys Lys His His Lys Val Val
                165                 170                 175

Leu Ser Lys Gln Asp Cys Asn Pro Arg Lys Met Asp Lys Pro Val Thr
            180                 185                 190

Leu Lys Ile Lys Pro Pro Lys Leu Thr Ser Gln Trp Arg Leu Ser
    195                 200                 205

Arg Glu Leu Ser Lys Ile Pro Leu Leu Arg Leu Gly Val Ser Leu Ile
    210                 215                 220

Asp Phe Arg Glu Pro Trp Val Glu Gly Phe Gly Asn Ala Phe Phe Ser
225                 230                 235                 240

Thr Leu Gly Tyr Glu Ala Asp Lys Ser Asn Leu Lys Thr Ser Ala Trp
                245                 250                 255

Cys Gln Cys Lys Tyr Phe Trp Ile Tyr Asp Thr Gly Val Asn Asn His
            260                 265                 270

Val Tyr Val Val Met Leu Asn Lys Asp Ala Gly Asp Asn Ala Gly Asp
        275                 280                 285

Leu Ile Thr Asn Gln Asn Ser Ile Ala His Ile Glu Gln Ile Gly Glu
    290                 295                 300

Gly Tyr Pro Tyr Trp Leu Tyr Phe Phe Gly Arg Ser Glu Arg Asp Leu
305                 310                 315                 320

Lys Ala Leu Ala Thr Ser Asn Thr Asn Ile Arg Asn Glu Phe Asn Thr
            325                 330                 335

Asn Pro Asn Ser Lys Lys Leu Lys Ile Ala Val Ile Gly Trp Ala Ser
            340                 345                 350

Ser Asn Asn Thr Ala Gln Asp Ser Thr Gln Gly Ala Asn Thr Pro Ile
        355                 360                 365

Glu Gly Thr Tyr Leu Ile Ser His Val Leu Gln Thr Ser Gly His Thr
370                 375                 380

Ala Gly Ala Ala Gln Ile Asn Asn Leu Phe Ala Ser Gly Trp Pro Asn
385                 390                 395                 400

Ser Gln Asn Tyr Pro Pro Leu Asn Leu Asp Lys Asn Asn Phe Asp Trp
            405                 410                 415

Gly Lys Arg Ala Leu Cys Ile Leu Arg Asn Asn Met Lys Ile Gly Asn
            420                 425                 430

Gln Asn Leu Asp Asp Glu Thr Thr Met Phe Ala Leu Phe Gly Pro Leu
        435                 440                 445

Val Glu Lys Ala Asn Trp Glu Gly Leu Glu Lys Ile Pro Glu Leu Lys
450                 455                 460

Pro Glu Leu Lys Asp Tyr Asn Ile Leu Met Arg Tyr Asn Phe Arg Phe
465                 470                 475                 480

Gln Trp Gly Gly His Gly Thr Glu Thr Phe Lys Thr Ser Ile Gly Asp
            485                 490                 495

Pro Ser Gln Ile Pro Cys Pro Tyr Gly Pro Gly Glu Ala Pro Gln His
            500                 505                 510

Leu Val Arg Asn Pro Ser Lys Val His Glu Gly Val Leu Asn Ala Trp
        515                 520                 525

Asp Tyr Asp Tyr Asp Gly Ile Val Arg Lys Thr Leu Lys Arg Leu
530                 535                 540

Leu Ala Ile Pro Thr Asp Ser Glu Glu Lys Ala Tyr Pro Leu Ala
545                 550                 555                 560

Gly Pro Lys Thr Glu Lys Leu Pro Ser Ser Asp Glu Glu Gly Glu Ser
            565                 570                 575

Asp Ile Ser Ser Ser Ser Asp Ser Ser Thr Gln Glu Ser Glu Glu Glu
            580                 585                 590

Lys Arg Tyr Arg Arg Arg His Lys Pro Ser Lys Arg Arg Leu Leu Gln
        595                 600                 605

His Val Gln Arg Leu Val Lys Arg Phe Arg Thr Leu
        610                 615                 620

<210> SEQ ID NO 15
<211> LENGTH: 629
<212> TYPE: PRT
<213> ORGANISM: Torque Teno Virus
<220> FEATURE:
<221> NAME/KEY: PEPTIDE
<222> LOCATION: (1)..(629)
<223> OTHER INFORMATION: amino acid sequence of TTV strain gt2 TTV13
      ORF1

<400> SEQUENCE: 15

Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Arg Tyr Arg Arg
            20                  25                  30

```
Ala Pro Arg Arg Arg Thr Lys Val Arg Arg Arg Lys Ala
        35                  40                  45

Pro Val Ile Gln Trp Asn Pro Ser Arg Arg Thr Cys Leu Ile Glu
 50                  55                  60

Gly Phe Trp Pro Leu Ser Tyr Gly His Trp Phe Arg Thr Cys Leu Pro
 65                  70                  75                  80

Phe Arg Arg Lys Asn Gly Leu Ile Phe Thr Gly Gly Cys Asp Trp
                 85                  90                  95

Thr Gln Trp Ser Leu Gln Asn Leu Tyr His Glu Lys Leu Asn Trp Arg
                100                 105                 110

Asn Ile Trp Thr Ala Ser Asn Val Gly Met Glu Phe Glu Phe Ala Arg
                115                 120                 125

Phe Leu Lys Gly Lys Phe Tyr Phe Phe Arg His Pro Trp Arg Asn Tyr
            130                 135                 140

Ile Val Thr Trp Asp Gln Asp Ile Pro Cys Lys Pro Leu Pro Tyr Gln
145                 150                 155                 160

Asn Leu His Pro Leu Leu Met Leu Leu Lys Lys Gln His Lys Leu Val
                165                 170                 175

Leu Ser Gln Gln Asn Cys Asn Pro Asn Arg Lys Gln Lys Pro Val Thr
                180                 185                 190

Leu Lys Phe Arg Pro Pro Lys Leu Thr Ser Gln Trp Arg Leu Ser
            195                 200                 205

Arg Glu Leu Ala Lys Met Pro Leu Ile Arg Leu Gly Val Ser Phe Ile
            210                 215                 220

Asp Leu Thr Glu Pro Trp Leu Glu Gly Trp Gly Asn Ala Phe Tyr Ser
225                 230                 235                 240

Val Leu Gly Tyr Glu Ala Ile Lys Glu Gln Gly His Trp Ser Asn Trp
                245                 250                 255

Ser Gln Ile Lys Tyr Tyr Trp Ile Tyr Asp Thr Gly Val Gly Asn Ala
            260                 265                 270

Val Tyr Val Val Met Leu Lys Gln Asp Val Asp Asp Asn Pro Gly Lys
            275                 280                 285

Met Ala Ser Thr Phe Lys Thr Thr Gln Gly Gln His Pro Asn Ala Ile
            290                 295                 300

Asp His Ile Glu Leu Ile Asn Glu Gly Trp Pro Tyr Trp Leu Tyr Phe
305                 310                 315                 320

Phe Gly Lys Ser Glu Gln Asp Ile Lys Lys Glu Ala His Ser Ala Glu
                325                 330                 335

Ile Ala Arg Glu Tyr Ala Thr Asn Pro Lys Ser Lys Lys Leu Lys Ile
                340                 345                 350

Gly Ile Val Gly Trp Ala Ser Ser Asn Phe Thr Thr Pro Gly Ser Ser
            355                 360                 365

Gln Asn Ser Gly Gly Asn Ile Ala Ala Ile Gln Gly Gly Tyr Val Ala
        370                 375                 380

Trp Ala Gly Gly Gln Gly Lys Leu Asn Leu Gly Ala Gly Ser Ile Gly
385                 390                 395                 400

Asn Leu Tyr Gln Gln Gly Trp Pro Ser Asn Gln Asn Trp Pro Asn Thr
                405                 410                 415

Asn Arg Asp Glu Thr Asn Phe Asp Trp Gly Leu Arg Ser Leu Cys Ile
                420                 425                 430

Leu Arg Asp Asn Met Gln Leu Gly Asn Gln Glu Leu Asp Asp Glu Cys
            435                 440                 445
```

```
Thr Met Leu Ser Leu Phe Gly Pro Phe Val Glu Lys Ala Asn Pro Ile
    450             455                 460
Phe Ala Thr Thr Asp Pro Lys Tyr Phe Pro Glu Leu Lys Asp Tyr
465             470                 475                 480
Asn Leu Ile Met Lys Tyr Ala Phe Lys Phe Gln Trp Gly His Gly
                485                 490                 495
Thr Glu Arg Phe Lys Thr Thr Ile Gly Asp Pro Ser Thr Ile Pro Cys
            500                 505                 510
Pro Phe Glu Pro Gly Asp Arg Phe His Ser Gly Ile Gln Asp Pro Ser
            515                 520                 525
Lys Val Gln Asn Thr Val Leu Asn Pro Trp Tyr Asp Cys Asp Gly
    530                 535                 540
Ile Val Arg Lys Asp Thr Leu Lys Arg Leu Leu Glu Leu Pro Thr Glu
545             550                 555                 560
Thr Glu Glu Glu Glu Lys Ala Tyr Pro Leu Leu Gly Gln Lys Thr Glu
                565                 570                 575
Lys Glu Pro Leu Ser Asp Ser Asp Glu Glu Ser Val Ile Ser Ser Thr
            580                 585                 590
Ser Ser Gly Ser Asp Gln Glu Glu Glu Thr Gln Arg Arg Lys His His
            595                 600                 605
Lys Pro Ser Lys Arg Arg Leu Leu Lys His Leu Gln Arg Val Val Lys
    610                 615                 620
Arg Met Lys Thr Leu
625
```

<210> SEQ ID NO 16
<211> LENGTH: 2735
<212> TYPE: DNA
<213> ORGANISM: Torque Teno Virus, strain AY823991
<220> FEATURE:
<221> NAME/KEY: misc_feature
<222> LOCATION: (2596)..(2622)
<223> OTHER INFORMATION: n is a, c, g, or t

<400> SEQUENCE: 16

| | | | | | |
|---|---|---|---|---|---|
| tcatgacagg | gttcaccgga | agggctgcaa | aattacagct | aaaaccacaa | gtctaacaca | 60 |
| ataaaccaca | aagtattaca | ggaaactgca | ataaatttag | aaataagtta | cacataacca | 120 |
| ccaaaccaca | ggaaactgtg | caaaaaagag | gaaataaatt | tcattggctg | ggcctgaagt | 180 |
| cctcattaga | ataataaaag | aaccaatcag | aagaacttcc | tcttttagag | tatataagta | 240 |
| agtgcgcaga | cgaatggctg | agtttatgcc | gctggtggta | gacacgaaca | gagctgagtg | 300 |
| tctaaccgcc | tgggcgggtg | ccggagctcc | tgagagcgga | gtcaaggggc | ctatcgggca | 360 |
| ggcggtaatc | cagcggaacc | gggcccccct | cgatggaaga | aagatggctg | acggtagcgt | 420 |
| actgcgcaca | cggattattc | tgcagctgta | aagacccgaa | aaacatcttc | gaaaaatgcc | 480 |
| ttacagacgc | tatcgcagac | gccgaagaag | accgacacgg | agatggaggc | accgagagtg | 540 |
| gagacgctac | tttcgatatc | ggtatcgacg | cgctcctcgc | cgccgccgca | caaaggtaag | 600 |
| gagacggagg | aaaaaagctc | cggtcataca | atggttccct | cctagccgga | gaacctgcct | 660 |
| catgaggga | ttttggccgt | tgagctacgg | acactggttc | cgtacctgtc | tccccttag | 720 |
| gcggttaaat | ggactagtat | tcccgggtgg | aggttgtgac | tggagccagt | ggagtttaca | 780 |
| aaacctttac | aatgaaaaac | ttaactggag | aaatatatgg | acagctagta | atgttggaat | 840 |
| ggaattcgct | agattttttaa | aaggaaagtt | ttactttttc | agacatccat | ggagaaatta | 900 |
| tataataact | tgggatcaag | atataccatg | caggccacta | ccttatcaaa | acctgcatcc | 960 |

```
actcctaatg ctactaaaaa aacagcacaa aattgtactt tcacagcaaa actgtaaccc      1020
aaacagaaaa caaaaacctg tcacattaaa attcaaacct ccgccaaaac taacatcaca      1080
atggagacta agtagagaat tagcaaagat gccactaata agacttggag taagctttat      1140
agacctaaca gaaccatggg tagaagggtg gggaaatgca ttttattccg tgctaggata      1200
tgaagcagta aaagaccaag gacactggtc aaactggaca caaataaaat actattggat      1260
ctatgacacg ggagtaggaa atgcagtata tgttatacta ttaaaaaaag acgttactga      1320
taatccagga aacatggcaa caacctttaa agcatcagga ggacagcatc cagatgcaat      1380
agatcacatt gaattgataa accaaggatg gccttactgg ttatactttt atggtaaaag      1440
tgaacaagac attaaaaaag aggcacacag cgcagaaata tcaagagaat atactagaga      1500
cccaaaatct aaaaaactaa aaataggaat agtaggatgg gcatcttcaa actcacaaac      1560
aacaggcagt gatcaaaaca gtggtggatc aacatcagct atacaaggtg gatatgtagc      1620
atatgcaggg tccggggtca taggagcagg gtcaatagga aatttatatc aacaaggatg      1680
gccatctaat caaaactggc ctaatacaaa cagagacaaa acaaactttg actggggaat      1740
acgaggacta tgtatactca gagataacat gcacttagga agccaagaat tagatgatga      1800
atgcacaatg ctcacattgt tcggacccctt tgtagaaaaa gcaaatccaa tatttgcaac      1860
aacagaccct aaattcttta aacctgaact caaagactat aatataatca tgaaatatgc      1920 cttaaattt cagtggggag acatggcac agaaagattt aaaaccaaca tcggagaccc      1980
cagcaccata ccctgcccct tcgaacccgg ggaccgcttc cacagcggga tacaagaccc      2040
ctccaaggta caaacaccg tcctcaaccc ctgggactat gactgtgatg ggattgttag      2100
aaaagatact ctcaaaagac ttctcgaact ccccacagag acagaggagg aggaagaggc      2160
gtacccactc cttggacaaa aaacagagaa agagccatta tcagactccg acgaagagag      2220
cgttatctca agcacgagca gtggatcctc tcaagaagaa gaaacgcaga gacgaagaca      2280
ccacaagcca agcaagcgac gactcctcaa gcacctccag cgggtggtaa agaggatgaa      2340
aacactgtga tagataaata tagaaaccta gcagacccct cactcaatgt cacaggacac      2400
atggaaaaat tcatgcagtt acatattcaa aacgtacaag aaataagagc taaaaatgct      2460
aaaaaatccc tcaataaact ttacttttct gattaatagc ggcctcctgt gtccaaccta      2520
tttttcctaa accccttcaa aatggcgggc gggacacaaa atggcggagg gactaagggg      2580
ggggcaagcc ccctnnnnn nnnnnnnnnn nnnnnnnnnn nnggggggcg acccccccgc      2640 accccccct gcggggctc cgcccctgc accccggga ggggggaaa ccccccctca      2700 accccccgcg gggggcaagc ccccctgcac ccccc                                2735

<210> SEQ ID NO 17
<211> LENGTH: 2872
<212> TYPE: DNA
<213> ORGANISM: Torque Teno Virus, strain AY823990
<220> FEATURE:
<221> NAME/KEY: misc_feature
<222> LOCATION: (2719)..(2732)
<223> OTHER INFORMATION: n is a, c, g, or t

<400> SEQUENCE: 17
tacactttgg ggttcaggag gctcaatttg gctcgcttcg ctcgcaccac gtttgctgcc        60
aggcggacct gattgaagac tgaaaaccgt taaattcaaa attgaaaagg gcgggcaaaa      120
tggcggacag ggggcggagt ttatgcaaat taatttatgc aaagtaggag gagctcgatt      180
```

-continued

```
ttaatttatg caaagtagga ggagtcaaat ctgattggtc gggagctcaa gtcctcattt      240 gcataggtgtg taaccaatca gaattaaggc gttcccacga aagcgaatat aagtaggtga      300
ggttccgaat ggctgagttt atgccgccag cggtagacag aactgtctag cgactgggcg      360
ggtgccggag gatccctgat ccggagtcaa ggggcctatc gggcaggagc agctaggcgg      420
agggcctatg ccggaacact gggaggaagc ctggttggaa gctaccaagg ctggcacga      480 tctcgactgc cgctgcggta actggcagga ccacctatgg ctcctactcg ccgatggaga      540
cgccgctttg gccgccgccg tagacgctat agaaagagac gctatggctg agacgacgc      600 tactaccgct acaggccgcg tgactatcgg cgacgatggc tggtaaggag aaggcggcgt      660
tccgtctacc gtagaggtgg acgtagagcg cgcccctacc gactgtttaa tccaaaagta      720
atgcggagag tagtaattag ggggtggtgg cctattttac aatgcttaaa aggacaggag      780
gcactaagat atagacctct acagtgggac acagagagac agtggagagt gagatcagac      840
ttcgaagacc agtacggata cctcgtacaa tacgggggag gttggggaag tggtgatgtg      900
acacttgaag gtctctacca agagcactta ttgtggagaa actcttggtc taaaggaaac      960
gatggaatgg acctagtaag atactttgga tgtgtagtat acctatatcc actaaaggac     1020
caggactatt ggttctggtg ggacacggac ttcaaagaat tatatgcaga aaacataaag     1080
gaatacagcc aaccatcagt aatgatgatg gcaaaaagaa caagaatagt aatagccaga     1140
gaaagggcac cacatagaag aaaagtaaga aaaatattta ttccgccacc ttcgagagac     1200
acaacacagt ggcagtttca gacagatttc tgcaatagaa agttatttac gtgggcagct     1260
ggtctaatag acatgcaaaa accgttcgat gctaatggag cctttagaaa tgcttggtgg     1320
ctggaacaga gaaatgatca gggagaaatg aaatacatag aactgtgggg aagagtaccc     1380
ccacaaggag attcagagct gcccaaaaaa aagaattct ccacaggaac agataaccca     1440
aactacaatg ttcaggacaa tgaggagaaa acatatacc ccattataat atacgtagac     1500
caaaaagatc aaaaaccaag aaaaaagtac tgcgtatgtt ataataagac cctcaacaga     1560
tggagactag acaggcaag tactctaaag ataggaaacc tgaaaggact agtactaaga     1620
cagctgatga atcaagaaat gacgtatata tggaaagaag gagaatacag tgccccctt     1680 gtacaaaggt ggaaaggcag cagattcgct gtgatagacg caagaaaggc agaccaagaa     1740
aacccgaaag tatcaacatg gccaattgag ggaacgtgga acacacagga cacagtactg     1800
aaggatgtat tcggtattaa cttgcaaaat caacaattta gggcggcgga ctttggtaaa     1860
ctcacactac caaaatcacc gcatgactta gacttcggtc accacagcag atttgggcca     1920
ttttgtgtga aaaatgaacc actggagttt caggtatacc ctccagaacc aactaacttg     1980
tggtttcagt acagatttt ctttcagttt ggaggtgaat accaaccccc cacaggaatc     2040
cgggatccat gcgttgatac accagcctat cctgtgccgc agtcaggaag tattacacac     2100
cccaaattcg ccggaaaagg aggaatgctc acggaaacag accgttgggg tatcactgct     2160
gcctcttcca gagccctcag tgcagataca cccacagagg cagcgcaaag tgcacttctc     2220
cgaggggact cggaagcgaa aggagaggaa accgaggaaa ccgcgtcatc gtccagtatc     2280
acgagtgccg aaagctctac tgagggagat ggatcgtctg atgatgaaga gacaatcaga     2340
cgcagaagga ggacctggaa gcgactcaga cgaatggtca gagagcagct tgaccgacga     2400
atggaccaca agcgacagcg acttcattga caccccccata agagaaagat gcctcaataa     2460
aaaacaaaag aaacgctaaa cagtgtccga ttactaatgg gggggggtcc gggggggct      2520 tgccccccccg caagctgggt taccgcacta actccctgcc aagtgaaact cggggacgag     2580
```

```
tgagtgcggg acatcccgtg taatggctac ataactaccc ggctttgctt cgacagtggc    2640
cgtggctcga ccctcacaca acactgcagg tagggggcgc aattgggatc gttagaaaac    2700
tatggccgag catgggggnn nnnnnnnnnn nnccaacccc cccggtgggg gggccaaggc    2760
cccccctaca cccccccatg ggggctgccg cccccccaaa cccccgcgt  cggatggggg    2820 gggctgcgcc ccccccaaac cccccttgcc cggggctgtg ccccggaccc cc           2872
```

<210> SEQ ID NO 18
<211> LENGTH: 1952
<212> TYPE: DNA
<213> ORGANISM: Torque Teno Virus
<220> FEATURE:
<221> NAME/KEY: misc_feature
<222> LOCATION: (1)..(1952)
<223> OTHER INFORMATION: TTV capsid encoding sequence for strain 76057-3

<400> SEQUENCE: 18

```
ccatgggtac caccaccacc accacctctc tgatgggtac cgcccgtcgc tggcgtcgcc    60
gttttggtcg ccgtcgccgt cgctatcgta aacgtcgcta cggctggcgt cgccgttatt    120
accgttatcg cccgcgttat tatcgccgtc gctggctggt gcgtcgccgt cgccgttctg    180
tttatcgccg tggcggtcgc cgtgcacgtc cgtaccgtat tagtgcattc aacccgaaag    240
tgatgcgccg tgtggttatt cgcggttggt ggccgatcct gcagtgcctg aaaggccaag    300
aaagtctgcg ctatcgtccg ctgcagtggg atgttgaaaa aagctggcgt atcaacacca    360
cgctggaaga taattatggt tacctggtgc agtatggcgg tggctggggt agcggcgaag    420
ttaccctgga aggcctgtac caggaacatc tgctgtggcg caacagttgg agcaagggta    480
atgatggcat ggatctggtg cgttattttg gttgtattgt ttatctgtac ccgctgaaag    540
atcaggatta ctggttctgg tgggataccg attttaaaga actgtatgca gaaagcatca    600
aagaatacag ccagccgtct gtgatgatga tggcgaaacg caccaaaatt gtgattgcac    660
gtagccgtgc accgcaccgc cgtaaagtgc gccgtatttt tattccgccg ccgtctcgcg    720 ataccacccca gtggcagttc cagaccgatt tttgtaatcg cccgctgttc acctgggccg    780
caggtctgat tgatctgcag aaaccgttcg atgcgaacgg cgccttttcgc aatgcgtggt    840 ggctggaaca gcgtaatgaa gccggcgaaa tgaaatatat tgaactgtgg ggtcgtgtgc    900
cgccgcaggg tgataccgaa ctgccggttc agacggaatt tcagaaaccg agcggttaca    960
acccgaaata ttacgtgaat ccgggcgaag aaaaaccgat ttatccggtg atcatctacg    1020
ttgatatgaa agatcagaaa ccgcgcaaaa atattgcgt gtgttacaac aaaacccctga    1080 atcgctggcg tagtgcccag gcaagcacgc tgaaaatcgg tgatctgcag ggcctggttc    1140
tgcgtcagct gatgaaccag gaaatgacct atacgtggaa agaaggtgaa tttaccaatg    1200
tgtttctgca gcgctggcgt ggctttcgcc tggcagttat tgatgcacgt aaagcggata    1260
ccgaaaaccc gaccgtgcag acgtggaaag ttgatggcca gtggaatacc cagggcacgg    1320
tgctgaaaga agttttcaac atcaacctga caacgaaca gatgcgccag gcggatttttg    1380 gcaaactgaa cctgccgaaa agcccgcatg atatcgattt cggtcatcac tctcgtttcg    1440
gcccgttttg cgtgaaaaac gaaccgctgg aatttcagct gaccgccccg gaaccgacga    1500
atctgtggtt tcagtataaa tttctgttcc agtttggtgg cgaataccag ccgccaaccg    1560
gtattcgcga tccgtgtgcg gataatccgg cctatccggt tccgcagtct ggtagtatca    1620
cccacccgaa atttgccggc aaaggtggca tgctgaccga aacggatcgc tgggggcatta    1680
```

| | |
|---|---|
| ccgcagcgag ctctcgtacg ctgagcgcag ataccccgac ggaagcaacc cagtctgcgc | 1740 |
| tgctgcgtgg tgatagtgag aaaaaaggcg aagaaaccga agaaacgagt agctctagta | 1800 |
| gcattaccag cgccgaatct agtacggaag gtgatggcag ctctgatgat gaagaaacca | 1860 |
| ttcgccgtcg ccgtcgcacc tggaaacgtc tgcgtcgcat ggtgcgtgaa cagctggatc | 1920 |
| gtcgcatgga tcataaacgc cagcgtctgc ac | 1952 |

<210> SEQ ID NO 19
<211> LENGTH: 1954
<212> TYPE: DNA
<213> ORGANISM: Torque Teno Virus
<220> FEATURE:
<221> NAME/KEY: misc_feature
<222> LOCATION: (1)..(1954)
<223> OTHER INFORMATION: TTV capsid encoding sequence for strain 76057-4

<400> SEQUENCE: 19

| | |
|---|---|
| caccatgggt accaccacca ccaccacctc tctgatgggt accgccgtc gctggcgtcg | 60 |
| ccgttttggt cgccgtcgcc gtcgctatcg taaacgtcgc tacggctggc gtcgccgtta | 120 |
| ttaccgttat cgcccgcgtt attatcgccg tcgctggctg gtgcgtcgcc gtcgccgttc | 180 |
| tgtttatcgc cgtggcggtc gccgtgcacg tccgtaccgt attagtgcat tcaacccgaa | 240 |
| agtgatgcgc cgtgtggtta ttcgcggttg gtggccgatc ctgcagtgcc tgaaaggcca | 300 |
| agaaagtctg cgctatcgtc cgctgcagtg ggatgttgaa aaaagctggc gtatcaacac | 360 |
| cacgctggaa gataattatg gttacctggt gcagtatggc ggtggctggg gtagcggcga | 420 |
| agttaccctg gaaggcctgt accaggaaca tctgctgtgg cgcaacagtt ggagcaaggg | 480 |
| taatgatggc atggatctgg tgcgttattt tggttgtatt gtttatctgt acccgctgaa | 540 |
| agatcaggat tactggttct ggtgggatac cgattttaaa gaactgtatg cagaaagcat | 600 |
| caaagaatac agccagccgt ctgtgatgat gatggcgaaa cgcaccaaaa ttgtgattgc | 660 |
| acgtagccgt gcaccgcacc gccgtaaagt gcgccgtatt tttattccgc cgccgtctcg | 720 |
| cgataccacc cagtggcagt tccagaccga ttttttgtaat cgcccgctgt tcacctgggc | 780 |
| cgcaggtctg attgatctgc agaaaccgtt cgatgcgaac ggcgcctttc gcaatgcgtg | 840 |
| gtggctggaa cagcgtaatg aagccggcga aatgaaatat attgaactgt ggggtcgtgt | 900 |
| gccgccgcag ggtgataccg aactgccggt tcagacggaa tttcagaaac cgagcggtta | 960 |
| caacccgaaa tattacgtga atccgggcga agaaaaaccg atttatccgg tgatcatcta | 1020 |
| cgttgatatg aaagatcaga aaccgcgcaa aaaatattgc gtgtgttaca acaaaaccct | 1080 |
| gaatcgctgg cgtagtgccc aggcaagcac gctgaaaatc ggtgatctgc agggcctggt | 1140 |
| tctgcgtcag ctgatgaacc aggaaatgac ctatacgtgg aaagaaggtg aatttaccaa | 1200 |
| tgtgtttctg cagcgctggc gtggctttcg cctggcagtt attgatgcac gtaaagcgga | 1260 |
| taccgaaaac ccgaccgtgc agacgtgaaa agttgatggc cagtggaata cccagggcac | 1320 |
| ggtgctgaaa gaagttttca acatcaacct gaacaacgaa cagatgcgcc aggcggattt | 1380 |
| tggcaaactg aacctgccga aaagcccgca tgatatcgat ttcggtcatc actctcgttt | 1440 |
| cggcccgttt tgcgtgaaaa acgaaccgct ggaatttcag ctgaccgccc ggaaccgac | 1500 |
| gaatctgtgg tttcagtata aatttctgtt ccagtttggt ggcgaatacc agccgccaac | 1560 |
| cggtattcgc gatccgtgtg cggataatcc ggcctatccg gttccgcagt ctggtagtat | 1620 |
| cacccacccg aaatttgccg gcaaaggtgg catgctgacc gaaacggatc gctgggcat | 1680 |
| taccgcagcg agctctcgta cgctgagcgc agatacccccg acggaagcaa cccagtctgc | 1740 |

```
gctgctgcgt ggtgatagtg agaaaaaagg cgaagaaacc gaagaaacga gtagctctag    1800
tagcattacc agcgccgaat ctagtacgga aggtgatggc agctctgatg atgaagaaac    1860
cattcgccgt cgccgtcgca cctggaaacg tctgcgtcgc atggtgcgtg aacagctgga    1920
tcgtcgcatg gatcataaac gccagcgtct gcac                                1954

<210> SEQ ID NO 20
<211> LENGTH: 1929
<212> TYPE: DNA
<213> ORGANISM: Torque Teno Virus
<220> FEATURE:
<221> NAME/KEY: misc_feature
<222> LOCATION: (1)..(1929)
<223> OTHER INFORMATION: TTV capsid encoding sequence for strain 76057-5

<400> SEQUENCE: 20
ccatgggctt tcgcaagaag atggagaaga agattcggta gaagaagaag aagatataga      60
aagagaagat acggttggag aagaagatac tacagatata gaccaagata ctacagaaga     120
agatggttgg ttagaagaag aagaagatca gtttacagaa gaggtggtag aagagctaga     180
ccttacagaa tttccgcttt taatccaaag gttatgagaa gagttgttat tagaggttgg     240
tggcctatct tgcaatgttt gaagggtcaa gaaagtttga gatacagacc attacaatgg     300
gatgttgaaa gtcttggag aattaatact acattggaag ataactacgg ttacttagtt     360
caatacggtg gtggttgggg ttcaggtgaa gttactttgg aaggtttgta ccaagaacat     420
ttgttgtgga gaaatagttg gtctaagggt aacgatggta tggatttggt tagatacttc     480
ggttgtatcg tttatttgta cccattgaag gatcaagatt actggttctg gtgggatact     540
gatttcaagg aattgtacgc tgaatctatt aaggaataca gtcaaccttc tgttatgatg     600
atggcaaaga gaacaaagat cgttatcgct agatcaagag caccacatag aagaaaagtt     660
agaagaattt ttattccacc tccatcaaga gataccactc aatggcaatt ccaaaccgat     720
ttttgtaata gaccttgtt cacttgggct gcaggtttga ttgatttgca aaaaccattc     780
gatgctaatg gtgcttttag aaacgcttgg tggttagaac aaagaaacga agcaggtgaa     840
atgaagtata ttgaattgtg gggtagagtt cctccacaag gtgacactga attgcctgtt     900
caaacagaat ttcaaaaacc ttctggttac aatccaaagt attacgttaa cccaggtgaa     960
gaaaagccta tctatccagt tattatctat gttgatatga aggatcaaaa gccaagaaag    1020
aaatactgtg tttgttacaa taagacattg aacagatgga gatcagctca agcatccacc    1080
ttgaagattg gtgacttgca aggtttggtt ttgagacaat tgatgaacca agaaatgaca    1140
tatacctgga aagaaggcga gtttactaac gttttcttgc aaagatggag aggttttaga    1200
ttggctgtta ttgatgctag aaaagcagat acagaaaatc caacagttca aacctggaag    1260
gttgatggtc aatggaacac tcaaggtaca gttttgaagg aagttttcaa tatcaactta    1320
aataacgaac aaatgagaca agctgatttt ggtaaattga atttgcctaa gtcaccacat    1380
gatattgatt tcggtcatca ttccagattc ggtcctttt gtgttaaaaa tgaaccattg    1440
gaatttcaat tgacagctcc tgaaccaacc aacttgtggt tccaatacaa gttcttgttc    1500
caattcggtg tgaataccaa acctccaact ggtattagag atccttgtgc tgataatcca    1560
gcatatcctg ttccacaatc aggttccatt acacatccta aatttgctgg taaaggtggt    1620
atgttgactg aaacagatag atgggggtatt accgctgcat cttcaagaac tttatctgca    1680
gataccccaa ctgaagctac acaaagtgca ttgttaagag gtgactctga aaagaaaggt    1740
```

| | |
|---|---|
| gaagaaaccg aagaaacttc cagttcttca tccattacat ctgctgaaag ttctaccgaa | 1800 |
| ggtgacggtt catccgatga tgaagaaact atcagaagaa gaagaagaac atggaaaaga | 1860 |
| ttgagaagaa tggttagaga acaattggat agaagaatgg atcataagag acaaagatta | 1920 |
| catgacgtc | 1929 |

<210> SEQ ID NO 21
<211> LENGTH: 10448
<212> TYPE: DNA
<213> ORGANISM: Torque Teno Virus
<220> FEATURE:
<221> NAME/KEY: misc_feature
<222> LOCATION: (1)..(10448)
<223> OTHER INFORMATION: TTV sequence for strain ttvgt1-7, ORF1, with a
      yeast invertase expression tag

<400> SEQUENCE: 21

| | |
|---|---|
| ggtagcgaac tagttattaa tagtaatcaa ttacggggtc attagttcat agcccatata | 60 |
| tggagttccg cgttacataa cttacggtaa atggcccgcc tggctgaccg cccaacgacc | 120 |
| cccgcccatt gacgtcaata atgacgtatg ttcccatagt aacgccaata gggactttcc | 180 |
| attgacgtca atgggtggag tatttacggt aaactgccca cttggcagta catcaagtgt | 240 |
| atcatatgcc aagtacgccc cctattgacg tcaatgacgg taaatggccc gcctggcatt | 300 |
| atgcccagta catgacctta tgggactttc ctacttggca gtacatctac gtattagtca | 360 |
| tcgctattac catggtcgag gtgagcccca cgttctgctt cactctcccc atctccccc | 420 |
| cctccccacc cccaattttg tatttattta ttttttaatt attttgtgca gcgatggggg | 480 |
| cggggggggg gggggggcgc gcgccaggcg gggcggggcg gggcgagggg cggggcgggg | 540 |
| cgaggcggag aggttcggcg gcagccaatc agaacggcgc gctccgaaag tttccttta | 600 |
| tggcgaaggc ggcggcggcg gcggccctat aaaaagcgaa gcgcgcggcg ggcgggagtc | 660 |
| gctgcgcgct gccttcgccc cgtgccccgc tccgccgccg cctcgcgccg cccgccccgg | 720 |
| ctctgactga ccgcgttact cccacaggtg agcgggcggg acggcccttc tcctccgggc | 780 |
| tgtaattagc gcttggttta atgacggctt gtttcttttc tgtggctgcg tgaaagcctt | 840 |
| gaggggctcc gggagggccc tttgtgcggg gggagcggct cggggggtgc gtgcgtgtgt | 900 |
| gtgtgcgtgg ggagcgccgc gtgcggctcc gcgctgcccg gcggctgtga gcgctgcggg | 960 |
| cgcggcgcgg ggctttgtgc gctccgcagt gtgcgcgagg ggagcgcggc cggggcggt | 1020 |
| gccccgcggt gcggggggg ctgcgagggg aacaaaggct gcgtgcgggg tgtgtgcgtg | 1080 |
| gggggtgag caggggtgt gggcgcgtcg gtcgggctgc aaccccccct gcaccccct | 1140 |
| ccccgagttg ctgagcacgg cccggcttcg ggtgcgggc tccgtacggg gcgtggcgcg | 1200 |
| gggctcgccg tgccgggcgg ggtggcgg caggtgggg tgccgggcgg ggcggggccg | 1260 |
| cctcgggccg gggagggctc gggggagggg cgcggcggcc cccggagcgc cggcggctgt | 1320 |
| cgaggcgcgc cgagccgcag ccattgcctt ttatggtaat cgtgcgagag ggcgcaggga | 1380 |
| cttcctttgt cccaaatctg tgcggagccg aaatctggga ggcgccgccg cacccctct | 1440 |
| agcgggcgcg gggcgaagcg gtgcggcgcc ggcaggaagg aaatgggcgg ggagggcctt | 1500 |
| cgtgcgtcgc cgcgccgccg tccccttctc cctctccagc ctcggggctg tccgcggggg | 1560 |
| gacggctgcc ttcggggggg acggggcagg gcggggttcg gcttctggcg tgtgaccggc | 1620 |
| ggctctagag cctctgctaa ccatgttcat gccttcttct ttttcctaca gctcctgggc | 1680 |
| aacgtgctgg ttattgtgct gtctcatcat tttggcaaag aattgacggt atcgataagc | 1740 |

```
ttgatatcgc caccatgctt ttgcaagcct tccttttcct tttggctggt tttgcagcca    1800
agatctccgc ggcttttgct cgccgatgga gacgccgctt tggccgccgc cgtagacgct    1860
atagaaagag acgctatgga tggaggagac gctactaccg ctacagaccg cgttactatc    1920
ggagacgatg gctggtaagg agaaggcggc gttccgtcta ccgacgaggt ggacgtagag    1980
cgcgcccta ccgcatttct gcctttaatc cgaaagtaat gcgtagagta gtgattagag     2040
ggtggtggcc aatactgcag tgcctaaaag gtcaggaatc actaagatac agaccacttc    2100
agtgggacgt agagaaaagc tggagaataa acacaactct tgaggacaac tatggatact    2160
tagtacagta tggaggtggt tggggtagcg gagaggtaac actggagggg ctgtatcagg    2220
agcacctact atggagaaac tcttggtcaa aaggaaacga tgggatggac ttagtgagat    2280
acttcggctg catagtatat ctatatccgt taaaagatca agactactgg ttttggtggg    2340
acacagattt taaagaatta tatgcagaga gtatcaaaga atactcacag ccatctgtaa    2400
tgatgatggc aaaagaaca aaaatagtga tcgcaagaag tagagcccca catagaagga     2460
aggtacgcag aattttcata ccgcctccaa gtagagacac gacacagtgg caatttcaaa    2520
ctgacttttg caatagacca ctattcacat gggctgcagg actcatagac ctccaaaaac    2580
catttgacgc aaacggtgcg ttcagaaatg cctggtggtt agaacagaga aacgaggcag    2640
gagaaatgaa atacatagag ctatgggta gagtaccacc ccaggggac acggaattac      2700
ccgttcaaac agaattccaa aaccctcgg gatataaccc aaaatactac gtaaacccgg     2760
gggaggaaaa accaatctac ccagtaataa tatacgtaga catgaaagac caaaaaccaa    2820
gaaaaagta ctgcgtctgc tacaacaaga cgcttaacag gtggcgcagc gctcaagcaa     2880
gcacattaaa aattggtgac ttgcaggggc tagtattgag acagctaatg aaccaagaaa    2940
tgacatacac atggaaagaa ggagaattta ccaatgtatt cctgcagagg tggagaggtt    3000
tcagattagc agtaatagac gcaagaaagg cagacacaga aaacccgaca gtccaaactt    3060
ggaaggtgga cggacagtgg aacacacaag ggacagtgct taaagaggtt ttcaatataa    3120
acctgaataa tgaacagatg agacaggcag actttggaaa actaaactta ccaaaatccc    3180
cgcacgacat tgactttgga caccacagta gatttggacc tttctgtgta aaaaacgaac    3240
cactggagtt tcaactaaca gccccagagc caactaacct gtggtttcag tacaaatttc    3300
tgtttcagtt tggaggtgaa taccaaccac caacaggcat ccgcgatccc tgcgctgata    3360
acccagccta tcctgtgccg cagtcaggaa gtattacaca ccccaaattc gccggaaaag    3420
gcggcatgct cacggaaaca gaccgttggg gtatcactgc tgcctcttcc cgaaccctca    3480
gtgcagatac acccacggaa gcaacgcaaa gtgcacttct ccgagggac tcggaaaaga     3540
aaggagagga aaccgaggaa acctcgtcat cgtccagtat cacgagtgcc gaaagctcta    3600
ctgaaggaga tggatcgtct gatgatgaag agacaatcag acgccgaagg aggacctgga    3660
agcgactcag acggatggtc cgagagcagc ttgaccgacg aatggaccac aagcgacagc    3720
gacttcattg ataatagggt accgtttaaa cgctagcggc cgcctcaggt gcaggctgcc    3780
tatcagaagg tggtggctgg tgtgggtgct acgagatttc gattccaccg ccgccttcta    3840
tgaaaggttg ggcttcggaa tcgttttccg ggacgccgc tggatgatcc tccagcgcgg     3900
ggatctcatg ctggagttct tcgcccaccc caacttgttt attgcagctt ataatggtta    3960
caaataaagc aatagcatca caaatttcac aaataaagca ttttttttcac tgcattctag    4020
ttgtggtttg tccaaactca tcaatgtatc ttatcatgtc tgtatggcaa acagctatta    4080
tgggtattat gggtctcgag atctatgtcg ggtgcggaga aagaggtaat gaaatggcat    4140
```

```
agggataaca gggtaatact agtggatccc ccgccccgta tccccaggt gtctgcaggc    4200
tcaaagagca gcgagaagcg ttcagaggaa agcgatcccg tgccaccttc cccgtgcccg    4260
ggctgtcccc gcacgctgcc ggctcgggga tgcgggggga gcgccggacc ggagcggagc    4320
cccgggcggc tcgctgctgc cccctagcgg gggaggacg taattacatc cctgggggct     4380
ttggggggg gctgtcccg tgagcggatc cgcggcccg tatccccag gtgtctgcag        4440
gctcaaagag cagcgagaag cgttcagagg aaagcgatcc cgtgccacct tccccgtgcc    4500
cgggctgtcc ccgcacgctg ccggctcggg gatgcggggg gagcgccgga ccggagcgga    4560
gccccgggcg ctcgctgct gccccctagc ggggagggga cgtaattaca tccctggggg     4620
ctttgggggg gggctgtccc cgtgagcgga tccgcggccc cgtatccccc aggtgtctgc    4680
aggctcaaag agcagcgaga agcgttcaga ggaaagcgat cccgtgccac cttcccgtg    4740
cccgggctgt ccccgcacgc tgccggctcg gggatgcggg gggagcgccg gaccggagcg    4800
gagcccgggg cggctcgctg ctgccccta gcggggagg gacgtaatta catccctggg      4860
ggctttgggg gggctgtc ccgtgagcg gatccgcggc cccgtatccc caggtgtct        4920
gcaggctcaa agagcagcga gaagcgttca ggaaagcg atcccgtgcc accttcccg       4980
tgcccgggct gtccccgcac gctgccggct cggggatgcg gggggagcgc cggaccggag    5040
cggagccccg gcggctcgc tgctgccccc tagcggggga gggacgtaat tacatccctg     5100
ggggctttgg gggggggctg tccccgtgag cggatccgcg gccccgtat ccccaggtgt     5160
ctgcaggctc aaagagcagc gagaagcgtt cagaggaaag cgatcccgtg ccaccttccc    5220
cgtgcccggg ctgtccccgc acgctgccgg ctcggggatg cgggggagc gccggaccgg    5280
agcggagccc cgggcggctc gctgctgccc cctagcgggg gagggacgta attacatccc    5340
tgggggcttt gggggggggc tgtccccgtg agcggatccg cggccccgta tccccaggt    5400
gtctgcaggc tcaaagagca gcgagaagcg ttcagaggaa agcgatcccg tgccaccttc    5460
cccgtgcccg ggctgtcccc gcacgctgcc ggctcgggga tgcggggga gcgccggacc    5520
ggagcggagc ccgggcggc tcgctgctgc cccctagcgg gggagggacg taattacatc    5580
cctgggggct ttggggggg gctgtcccg tgagcggatc cgcggggctg caggaattcg     5640
atagcttgca tgcctgcagg ctggcgtttt tccataggct ccgcccccct gacgagcatc    5700
acaaaaatcg acgctcaagt cagaggtggc gaaacccgac aggactataa agataccagg    5760
cgtttccccc tggaagctcc ctcgtgcgct ctcctgttcc gaccctgccg cttaccggat    5820
acctgtccgc ctttctccct tcgggaagcg tggcgctttc tcatagctca cgctgtaggt    5880
atctcagttc ggtgtaggtc gttcgctcca agctgggctg tgtgcacgaa ccccccgttc    5940
agcccgaccc ctgcgcctta ccggtaact atcgtcttga gtccaacccg gtaagacacg     6000
acttatcgcc actggcagca gccactggta acaggattag cagagcgagg tatgtaggcg    6060
gtgctacaga gttcttgaag tggtggccta actacggcta cactagaagg acagtatttg    6120
gtatctgcgc tctgctgaag ccagttacct tcggaaaaag agttggtagc tcttgatccg    6180
gcaaacaaac caccgctggt agcggtggtt tttttgtttg caagcagcag attacgcgca    6240
gaaaaaaagg atctcaagaa gatcctttga tcttttctac ggggtctgac gctcagtgga    6300
acgaaaactc acgttaaggg attttggtca tgagattatc aaaaaggatc ttcacctaga    6360
tccttttaaa ttaaaaatga agttttaaat caatctaaag tatatatgag taaacttggt    6420
ctgacagtta ccaatgctta atcagtgagg cacctatctc agcgatctgt ctatttcgtt    6480
```

```
catccatagt tgcctgactc cccgtcgtgt agataactac gatacgggag ggcttaccat    6540
ctggccccag tgctgcaatg ataccgcgag acccacgctc accggctcca gatttatcag    6600
caataaacca gccagccgga agggccgagc gcagaagtgg tcctgcaact ttatccgcct    6660
ccatccagtc tattaattgt tgccgggaag ctagagtaag tagttcgcca gttaatagtt    6720
tgcgcaacgt tgttgccatt gctacaggca tcgtggtgtc acgctcgtcg tttggtatgg    6780
cttcattcag ctccggttcc caacgatcaa ggcgagttac atgatccccc atgttgtgca    6840
aaaaagcggt tagctccttc ggtcctccga tcgttgtcag aagtaagttg gccgcagtgt    6900
tatcactcat ggttatggca gcactgcata attctcttac tgtcatgcca tccgtaagat    6960
gcttttctgt gactggtgag tactcaacca agtcattctg agaatagtgt atgcggcgac    7020
cgagttgctc ttgcccggcg tcaatacggg ataataccgc gccacatagc agaactttaa    7080
aagtgctcat cattggaaaa cgttcttcgg ggcgaaaact ctcaaggatc ttaccgctgt    7140
tgagatccag ttcgatgtaa cccactcgtg cacccaactg atcttcagca tcttttactt    7200
tcaccagcgt ttctgggtga gcaaaaacag gaaggcaaaa tgccgcaaaa aagggaataa    7260
gggcgacacg gaaatgttga atactcatac tcttcctttt tcaatattat tgaagcattt    7320
atcagggtta ttgtctcatg agcggttaat aaccctgggg atccagacat gataagatac    7380
attgatgagt ttggacaaac cacaactaga atgcagtgaa aaaaatgctt tatttgtgaa    7440
atttgtgatg ctattgcttt atttgtaacc attataagct gcaataaaca agttaacaac    7500
aacaattgca ttcattttat gtttcaggtt caggggagg tgtgggaggt tttttaaagc    7560
aagtaaaacc tctacaaatg tggtatggct gattatgatc tctagaact agtggatcag    7620
cgagctctag catttaggtg acactataga ataggccct ctagcgaatt ctcgactcat    7680
tcctttgccc tcggacgagt gctggggcgt cggtttccac tatcggcgag tacttctaca    7740
cagccatcgg tccagacggc cgcgcttctg cgggcgattt gtgtacgccc gacagtcccg    7800
gctccggatc ggacgattgc gtcgcatcga ccctgcgccc aagctgcatc atcgaaattg    7860
ccgtcaacca agctctgata gagttggtca agaccaatgc ggagcatata cgcccggagc    7920
cgcggcgatc ctgcaagctc cggatgcctc cgctcgaagt agcgcgtctg ctgctccata    7980
caagccaacc acggcctcca agaagaagatg ttggcgacct cgtattggga atccccgaac    8040
atcgcctcgc tccagtcaat gaccgctgtt atgcggccat tgtccgtcag acattgttg    8100
gagccgaaat ccgcgtgcac gaggtgccgg acttcggggc agtcctcggc ccaaagcatc    8160
agctcatcga gagcctgcgc gacggacgca ctgacggtgt cgtccatcac agtttgccag    8220
tgatacacat ggggatcagc aatcgcgcat atgaaatcac gccatgtagt gtattgaccg    8280
attccttgcg gtccgaatgg gccgaacccg ctcgtctggc taagatcggc cgcagcgatc    8340
gcatccatga gctccgcgac gggttgcaga acagcgggca gttcggtttc aggcaggtct    8400
tgcaacgtga caccctgtgc acggcggag atgcaatagg tcaggctctc gctgaattcc    8460
ccaatgtcaa gcacttccgg aatcgggagc gcggccgatg caaagtgccg ataaacataa    8520
cgatctttgt agaaaccatc ggcgcagcta tttacccgca ggacatatcc acgccctcct    8580
acatcgaagc tgaaagcacg agattcttcg ccctccgaga ctgcatcag tcggagacg    8640
ctgtcgaact tttcgatcag aaacttcgcg acagacgtcg cggtgagttc aggcttttc    8700
atggatccag atttcgctca agttagtata aaaaagcagg cttcaatcct gcagagaagc    8760
tctggcacga caggtttccc gactggaaag cgggcagtga gcgcaacgca attaatgtga    8820
gttagctcac tcattaggca ccccaggctt tacactttat gcttccggct cgtatgttgt    8880
```

```
gtggaattgt gagcggataa caatttcaca caggaaacag ctatgaccat gattacg

```
<213> ORGANISM: Torque Teno Virus
<220> FEATURE:
<221> NAME/KEY: PEPTIDE
<222> LOCATION: (1)..(21)
<223> OTHER INFORMATION: ttgvt1 peptide sequence (numbering based on the
      corresponding AY823990 sequence) from the ORF1 capsid protein
      corresponding to residues 459-479

<400> SEQUENCE: 23

Asp Phe Gly His His Ser Arg Phe Gly Pro Phe Cys Val Lys Asn Glu
1               5                   10                  15

Pro Leu Glu Phe Gln
            20

<210> SEQ ID NO 24
<211> LENGTH: 26
<212> TYPE: PRT
<213> ORGANISM: Torque Teno Virus
<220> FEATURE:
<221> NAME/KEY: PEPTIDE
<222> LOCATION: (1)..(26)
<223> OTHER INFORMATION: ttgvt1 peptide sequence (numbering based on the
      corresponding AY823990 sequence) from the ORF1 capsid protein
      corresponding to residues 612-637

<400> SEQUENCE: 24

Cys Thr Trp Lys Arg Leu Arg Arg Met Val Arg Glu Gln Leu Asp Arg
1               5                   10                  15

Arg Met Asp His Lys Arg Gln Arg Leu His
            20                  25

<210> SEQ ID NO 25
<211> LENGTH: 637
<212> TYPE: PRT
<213> ORGANISM: Torque Teno Virus
<220> FEATURE:
<221> NAME/KEY: PEPTIDE
<222> LOCATION: (1)..(637)
<223> OTHER INFORMATION: amino acid sequence of TTV strain AY823990 ORF1

<400> SEQUENCE: 25

Met Ala Pro Thr Arg Arg Trp Arg Arg Arg Phe Gly Arg Arg Arg Arg
1               5                   10                  15

Arg Tyr Arg Lys Arg Arg Tyr Gly Trp Arg Arg Arg Tyr Tyr Arg Tyr
            20                  25                  30

Arg Pro Arg Asp Tyr Arg Arg Arg Trp Leu Val Arg Arg Arg Arg Arg
            35                  40                  45

Ser Val Tyr Arg Arg Gly Gly Arg Arg Ala Arg Pro Tyr Arg Leu Phe
        50                  55                  60

Asn Pro Lys Val Met Arg Arg Val Val Ile Arg Gly Trp Trp Pro Ile
65                  70                  75                  80

Leu Gln Cys Leu Lys Gly Gln Glu Ala Leu Arg Tyr Arg Pro Leu Gln
                85                  90                  95

Trp Asp Thr Glu Arg Gln Trp Arg Val Arg Ser Asp Phe Glu Asp Gln
            100                 105                 110

Tyr Gly Tyr Leu Val Gln Tyr Gly Gly Trp Gly Ser Gly Asp Val
        115                 120                 125

Thr Leu Glu Gly Leu Tyr Gln Glu His Leu Leu Trp Arg Asn Ser Trp
    130                 135                 140

Ser Lys Gly Asn Asp Gly Met Asp Leu Val Arg Tyr Phe Gly Cys Val
145                 150                 155                 160
```

```
Val Tyr Leu Tyr Pro Leu Lys Asp Gln Asp Tyr Trp Phe Trp Trp Asp
                165                 170                 175
Thr Asp Phe Lys Glu Leu Tyr Ala Glu Asn Ile Lys Glu Tyr Ser Gln
                180                 185                 190
Pro Ser Val Met Met Met Ala Lys Arg Thr Arg Ile Val Ile Ala Arg
                195                 200                 205
Glu Arg Ala Pro His Arg Arg Lys Val Arg Lys Ile Phe Ile Pro Pro
            210                 215                 220
Pro Ser Arg Asp Thr Thr Gln Trp Gln Phe Gln Thr Asp Phe Cys Asn
225                 230                 235                 240
Arg Lys Leu Phe Thr Trp Ala Ala Gly Leu Ile Asp Met Gln Lys Pro
                245                 250                 255
Phe Asp Ala Asn Gly Ala Phe Arg Asn Ala Trp Trp Leu Glu Gln Arg
                260                 265                 270
Asn Asp Gln Gly Glu Met Lys Tyr Ile Glu Leu Trp Gly Arg Val Pro
            275                 280                 285
Pro Gln Gly Asp Ser Glu Leu Pro Lys Lys Lys Glu Phe Ser Thr Gly
        290                 295                 300
Thr Asp Asn Pro Asn Tyr Asn Val Gln Asp Asn Glu Glu Lys Asn Ile
305                 310                 315                 320
Tyr Pro Ile Ile Ile Tyr Val Asp Gln Lys Asp Gln Lys Pro Arg Lys
                325                 330                 335
Lys Tyr Cys Val Cys Tyr Asn Lys Thr Leu Asn Arg Trp Arg Leu Gly
                340                 345                 350
Gln Ala Ser Thr Leu Lys Ile Gly Asn Leu Lys Gly Leu Val Leu Arg
            355                 360                 365
Gln Leu Met Asn Gln Glu Met Thr Tyr Ile Trp Lys Glu Gly Glu Tyr
        370                 375                 380
Ser Ala Pro Phe Val Gln Arg Trp Lys Gly Ser Arg Phe Ala Val Ile
385                 390                 395                 400
Asp Ala Arg Lys Ala Asp Gln Glu Asn Pro Lys Val Ser Thr Trp Pro
                405                 410                 415
Ile Glu Gly Thr Trp Asn Thr Gln Asp Thr Val Leu Lys Asp Val Phe
                420                 425                 430
Gly Ile Asn Leu Gln Asn Gln Gln Phe Arg Ala Ala Asp Phe Gly Lys
            435                 440                 445
Leu Thr Leu Pro Lys Ser Pro His Asp Leu Asp Phe Gly His His Ser
450                 455                 460
Arg Phe Gly Pro Phe Cys Val Lys Asn Glu Pro Leu Glu Phe Gln Val
465                 470                 475                 480
Tyr Pro Pro Glu Pro Thr Asn Leu Trp Phe Gln Tyr Arg Phe Phe
                485                 490                 495
Gln Phe Gly Gly Glu Tyr Gln Pro Thr Gly Ile Arg Asp Pro Cys
            500                 505                 510
Val Asp Thr Pro Ala Tyr Pro Val Pro Gln Ser Gly Ser Ile Thr His
            515                 520                 525
Pro Lys Phe Ala Gly Lys Gly Met Leu Thr Glu Thr Asp Arg Trp
        530                 535                 540
Gly Ile Thr Ala Ala Ser Ser Arg Ala Leu Ser Ala Asp Thr Pro Thr
545                 550                 555                 560
```

```
Glu Ala Ala Gln Ser Ala Leu Leu Arg Gly Asp Ser Glu Ala Lys Gly
                565                 570                 575

Glu Glu Thr Glu Glu Thr Ala Ser Ser Ser Ile Thr Ser Ala Glu
        580                 585                 590

Ser Ser Thr Glu Gly Asp Gly Ser Ser Asp Asp Glu Glu Thr Ile Arg
        595                 600                 605

Arg Arg Arg Arg Thr Trp Lys Arg Leu Arg Arg Met Val Arg Glu Gln
610                 615                 620

Leu Asp Arg Arg Met Asp His Lys Arg Gln Arg Leu His
625                 630                 635
```

```
<210> SEQ ID NO 26
<211> LENGTH: 27
<212> TYPE: DNA
<213> ORGANISM: Artificial Sequence
<220> FEATURE:
<223> OTHER INFORMATION: DNA Primer
<220> FEATURE:
<221> NAME/KEY: misc_feature
<222> LOCATION: (1)..(27)
<223> OTHER INFORMATION: artificial primer

<400> SEQUENCE: 26
cgtactcgag tcacagtgtt ttcatcc                                           27

<210> SEQ ID NO 27
<211> LENGTH: 27
<212> TYPE: DNA
<213> ORGANISM: Artificial Sequence
<220> FEATURE:
<223> OTHER INFORMATION: DNA Primer
<220> FEATURE:
<221> NAME/KEY: misc_feature
<222> LOCATION: (1)..(27)
<223> OTHER INFORMATION: artificial primer

<400> SEQUENCE: 27
ctaggtacca tgccttacag acgctat                                           27

<210> SEQ ID NO 28
<211> LENGTH: 27
<212> TYPE: DNA
<213> ORGANISM: Artificial Sequence
<220> FEATURE:
<223> OTHER INFORMATION: DNA Primer
<220> FEATURE:
<221> NAME/KEY: misc_feature
<222> LOCATION: (1)..(27)
<223> OTHER INFORMATION: artificial primer

<400> SEQUENCE: 28
ctaggtacca tgcctttcca ccgctat                                           27

<210> SEQ ID NO 29
<211> LENGTH: 26
<212> TYPE: DNA
<213> ORGANISM: Artificial Sequence
<220> FEATURE:
<223> OTHER INFORMATION: DNA Primer
<220> FEATURE:
<221> NAME/KEY: misc_feature
<222> LOCATION: (1)..(26)
<223> OTHER INFORMATION: artificial primer

<400> SEQUENCE: 29
cgtactcgag ctatagggtc ctgaat                                            26
```